US00RE39197E

(19) United States
(12) Reissued Patent
Link et al.

(10) Patent Number: US RE39,197 E
(45) Date of Reissued Patent: Jul. 18, 2006

(54) CELL ADHESION-INHIBITING ANTIINFLAMMATORY AND IMMUNE-SUPPRESSIVE COMPOUNDS

(75) Inventors: James T. Link, Evanston, IL (US); Gang Liu, Gurnee, IL (US); Zhonghua Pei, Libertyville, IL (US); Tom von Geldern, Richmond, IL (US); Martin Winn, Deerfield, IL (US); Zhili Xin, Lake Bluff, IL (US)

(73) Assignee: Abbott Laboratories, Abbott Park, IL (US)

(21) Appl. No.: 10/356,794

(22) Filed: Aug. 29, 2002

Related U.S. Patent Documents

Reissue of:
(64) Patent No.: 6,110,922
Issued: Aug. 29, 2000
Appl. No.: 09/222,491
Filed: Dec. 29, 1998

(51) Int. Cl.

| | |
|---|---|
| ***A61K 31/505*** | (2006.01) |
| ***A61K 31/405*** | (2006.01) |
| ***C07D 239/70*** | (2006.01) |
| ***C07D 319/14*** | (2006.01) |
| ***C07D 319/00*** | (2006.01) |

(52) U.S. Cl. ..... 514/259; 514/395; 514/415; 514/712; 544/253; 544/282; 548/306.4; 549/362; 549/469; 568/58

(58) Field of Classification Search ..... 514/259, 514/395, 415, 712; 544/253, 282; 548/306.4; 549/362, 469; 568/58
See application file for complete search history.

(56) References Cited

U.S. PATENT DOCUMENTS

| | | | |
|---|---|---|---|
| 4,973,599 | A | 11/1990 | Gilman et al. |
| 5,028,629 | A | 7/1991 | Hite et al. |
| 5,208,253 | A | 5/1993 | Boschelli et al. |
| 5,776,951 | A | 7/1998 | Arrowsmith et al. |
| 5,817,862 | A | 10/1998 | Poetsch et al. |
| 5,883,106 | A | 3/1999 | Stevens et al. |
| 5,883,133 | A | 3/1999 | Schwark et al. |
| 5,912,266 | A | 6/1999 | Perez |
| 6,329,362 | B1 | 12/2001 | Archibald et al. |

FOREIGN PATENT DOCUMENTS

| | | |
|---|---|---|
| CA | 2245586 | 8/1997 |
| DE | 2123383 | 12/1971 |
| EP | 0219756 | 10/1986 |
| EP | 835 867 | 4/1998 |
| EP | 887 340 | 12/1998 |
| GB | 2 117 760 A | 10/1983 |
| JP | 62012757 | 1/1987 |
| JP | 12072766 | 3/2000 |
| WO | WO98/13347 | 2/1998 |
| WO | WO98/39303 | 9/1998 |
| WO | WO98/54207 | 12/1998 |
| WO | WO99/11258 | 3/1999 |
| WO | WO99/20617 | 4/1999 |
| WO | WO99/20618 | 4/1999 |
| WO | WO99/49856 | 10/1999 |
| WO | WO00/15604 | 3/2000 |
| WO | WO00/15645 | 3/2000 |
| WO | WO00/21920 | 4/2000 |
| WO | WO00/48989 | 8/2000 |
| WO | WO01/06984 | 2/2001 |
| WO | WO01/07052 | 2/2001 |
| WO | WO01/27102 | 4/2001 |

OTHER PUBLICATIONS

Springer, T.A., 1994, Traffic Signals for Lymphocyte Recirculation and Leukocyte Emigration: The Multistep Paradigm, CELL, 76: 301–314.*
Lawrence, M.B., Springer, T.A., 1991, Leukocytes' Roll on a Selectin in Physiologic Flow Rate: Distinction from and Prerequisite for Adhesion Through Integrins, CELL, 65:859–873.*
Von Adrian, V., Chambers, J.D., McEnvoy, L.M. Bargatze, R.F., Arfos, K.E., Butcher, E.C., 1991, Two–Step Model of Leukocyte–Endothelial Cell Interactions in Inflammation, Proc. National Acad. Sci USA, 88:7538–7542.*
Ley, K., Gaehtgens, P., Fennie, C., Singer, M.S., Lasky, L.H., Rosen, S.D., 1991, Lectin–Like Cell Adhesion Molecule 1 Mediates Rolling in Mesenteric Venules, in vivo, BLOOD, 77:2553–2555.*
Higuchi, T., Stella, V., Pro–drugs as Novel Delivery Systems, vol. 14 of the A.C.S. Symposium Series, (1993).*
Roche, E.B., Bioreversible Carriers in Drug Design, American Pharmaceutical Association and Pergamon Press, 1987.*
Prescott, E., Methods in Cell Biology, vol. XIV, Academic Press, New York, NY (1976), p. 33 et seq.*
Berge, S.M., et al. J. Pharmaceutical Sciences, 1977, 66:1 et seq.*
Kakimoto, et al., Cell Immunol 142:326–337, 1992.*
Knoerzer, et al., Toxical Pathol 25:13–19, 1997.*
Schimmer, et al., J. Immunol 160: 1455–1477, 1998.*
Oppenheimer–Marks, et al., J. Clin. Invest 101: 1261–1272, 1998.*
Wegner, et al., Science 247:456–459, 1990.*
Bloemen, et al., Am J. Respir Crit Care Med 153:521–529, 1996.*
Wegner, et al., Lung 170: 267–279, 1992.*
Mulligan, et al., J Immunol 154:1350–1363, 1995.*
Nagase, et al., Am J Respir Crit Care Med 154:504–510, 1996.*
Bennet, et al., J Pharmacol Exp Ther, 280:988–1000, 1997.*
Hasagawa, et al., Int Immunol, 6:831–838, 1994.*
Herrold, et al., Cell Immunol, 157:489–500, 1994.*
Tanaka, et al., J. Immunol, 151:5088–5095, 1993.*
Kawasaki, et al., J. Immunol, 150:1074–1083, 1993.*

(Continued)

*Primary Examiner*—Golam M. M. Shameem
(74) *Attorney, Agent, or Firm*—Finnegan, Henderson, Farabow, Garrett & Dunner LLP

(57) ABSTRACT

The present invention relates to novel cinnamide compounds that are useful for treating inflammatory and immune diseases, to pharmaceutical compositions comprising these compounds, and to methods of inhibiting inflammation or suppressing immune response in a mammal.

35 Claims, No Drawings

OTHER PUBLICATIONS

Panes, et al., Gastroenterology, 108:1761–1769, 1995.*
Hallahan, et al., Proc Natl Acad Sci USA, 94:6432–6437, 1997.*
Tamiya, et al., Immunopharmacology, 29(1):53–63, 1995.*
Hartman, et al., Cardiovasc Res, 30(1):47–54, 1995.*
DeMeester, et al., Transplantation, 62(10): 1477–1485, 1996.*
Horgan, et al., Am J Physiol, 261(5):H1578–H1584, 1991.*
Bowes, et al., Exp Neurol, 119(2):215–219, 1993.*
Chopp, et al., Stroke, 25(4):869–875, 1994.*
Clark, et al., Neurosurg, 75(4): 623–627, 1991.*
Gute, et al., Mol Cell Biochem, 179: 169–187, 1998.*
Isobe, et al., Science, 255: 1125–1127, 1992.*
Talento, et al., Transplantation, 55: 418–422, 1993.*
Cosimi, et al., J. Immunol, 144: 4606–4612, 1990.*
Nakao, et al., Muscle Nerve, 18:93–102, 1995.*
Gorczynski, Wojcik, J. Immunol, 152:2011–2019, 1994.*
He, et al., Opthalmol Vis Sci, 35: 3218–3225, 1994.*
Zeng, et al., Transplantation, 58: 681–689, 1994.*
Harning, et al., Transportation, 52: 842–845, 1991.*
Aoudjit, et al., J. Immunol, 161: 2333–2338, 1998.*
Gross, et al., Science 281, 703–706, 1998.*
Ali, H. et al., *Mechanisms of Inflammation and Leukocyte Activation,* Med. Clin. North America (1997) 81:1–28.
Aoudjit, et al., J. Immunol. (1998) 161: 2333–2338.
Bella, J., et al., *The Structure of the Two Amino–terminal Domains of Human ICAM–1 Suggests How it Functions as a Rhinovirus Receptor and As An LFA–1 Integrin Ligand,* Proc. Natl. Acad. Sci., USA (1998) 95:4140–4145.
Bennet, et al., *An ICAM–1 Antisense Oligonucleotide Prevents and Reverses Dextran Sulfate Sodium–Induced Colitis in Mice,* J. Pharmacol. Exp. Ther. (1997) 280:988–1000.
Berge, S.M., et al., *Pharmaceutical Salts,* J. Pharmaceutical Sciences (1977) 66:1 et seq.
Binnerts, M.E., et al., *How LFA–1 Binds to Different Ligands,* Immunol. Today (1999) 20:240–245.
Bloemen, et al., *LFA–1, and not Mac–1, is Crucial for the Development of Hyperreactivity in a Murine Model of Nonallergic Asthma,* Am. J. Respir. Crit. Care Med. (1996) 153:521–529.
Boschelli, D.H., et al., *Inhibition of E–Selectin–, ICAM–1–, and VCAM–1–Mediated Cell Adhesion by Benzo[b] thiophene–, Benzofuran–, Indole–, and Naphthalene–2–Carboxamides: Identification of PD 144795 as an Antiinflammatory Agent,* J. Med. Chem. (1995) 38:4597–4614.
Bowes, et al., *Monoclonal Antibody to the ICAM–1 Adhesion Site Reduces Neurological Damage in a Rabbit Cerebral Embolism Stroke Model,* Exp. Neurol. (1993) 119(2):215–219.
Carlos, T.M., *Leukocyte–Endothelial Adhesion Molecules,* Blood (1994) 84:2068–2101.
Chemical Abstracts (1987) 106:23, Abstract No. 196262.
Chopp, et al., *Postischemic Administration of an Anti–Mac–1 Antibody Reduces Ischemic Cell Damage After Transient Middle Cerebral Artery Occlusion in Rats,* Stroke (1994) 25(4):869–875.
Clark, et al., *Reduction of central nervous system ischemic injury by monoclonal antibody to intercellular adhesion molecule,* Neurosurg. (1991) 75(4): 623–627.
Cosimi, et al., *In Vivo Effects of Monoclonal Antibody to ICAM–1 (CD54) In Nonhuman Primates with Renal Allografts,* J. Immunol. (1990) 144: 4606–4612.
DeMeester, et al., *Attenuation of Rat Lung Isograft Reperfusion Injury with a Combination of Anti–ICAM–1 and Anti–$\beta_2$Integrin Monoclonal Antibodies,* Transplantation (1996) 62(10): 1477–1485.
Edwards, C.P. et al., *Mapping the Intercellular Adhesion Molecule–1 and –2 Binding Site on the Inserted Domain of Leukocyte Function–associated Antigen–1,* J. Biol. Chem. (1998) 273:28937–28944.
Emeigh, J.E., et al., *Small Molecule Antagonists of LFA–1–Mediated Cell Adhesion,* 221st ACS National Meeting, San Diego, CA, USA (2001) MEDI 256.
Fisher, K.L., et al., *Identification of the Binding Site in Intercellular Adhesion Molecule 1 for its Receptor, Leukocyte Function–associated Antigen 1,* Mol. Biol. Cell (1997) 8:501–515.
Franke et al., *Synthetische Juvenihormone,* Helvetica Chimca Acta (1975) 58(32):268–278.
Gadek, T.R., et al.; *Identification and Characterization of Antagonists of the LFA–1/ICAM–1 Protein—Protein Interaction as Novel Immunomodulatory Agents,* 220th ACS National Meeting, Washington, D.C., USA (2000) MEDI 177.
Gahmberg, C.G., *Leukocyte Adhesion: CD11/CD18 Integrins and Intercullular Adhesion Molecules,* Curr. Opin. Cell Biol. (1997) 9:643–650.
Gahmberg, C.G., *Leukocyte Adhesion: Structure and Function of Human Leukocyte $\beta_2$–integrins and Their Cellular Ligands,* Eur. J. Biochem. (1997) 245:215–232.
Gorczynski, Wojcik, *A Role for Nonspecific (Cyclosporin A) or Specific (Monoclonal Antibodies to ICAM–1, LFA–1, and IL–10) Immunomodulation in the Prolongation of Skin Allografts After Antigen–Specific Pretransplant Immunization or Transfusion,* J. Immunol. (1994) 152:2011–2019.
Green, J.M., *T Cell Receptor Stimulation, But Not CD28 Costimulation, Is Dependent on LFA–1–Mediated Events,* Eur. J. Immunology (1994) 24:265–272.
Gross, et al., *Identification of LFA–1 as a Candidate Autoantigen in Treatment–Resistant Lyme Arthritis,* Science (1988) 281, 703–706.
Gute, et al., *Inflammatory responses to ischemic and reperfusion in skeletal muscle,* Mol. Cell Biochem. (1998) 179: 169–187.
Hallahan, et al., *Intercellular adhesion molecule 1 knockout abrogates radiation induced pulmonary inflammation,* Proc. Natl. Acad. Sci. USA (1997) 94:6432–6437.
Halloran, et al., *Cellular Adhesion Molecules in Rat Adjuvant Arthritis,* Arthritis Rheum. (1996) 39:810–819.
Hamilton, G.S., et al., *Fluorenylalkanoic and Benzoic Acids as Novel Inhibitors of Cell Adhesion Processes in Leukocytes,* J. Med. Chem. (1995) 38:1650–1656.
Harning, et al., *Reduction in the Severity of Graft–Versus–Host Disease and Increased Survival in Allogeneic Mice By Treatment With Monoclonal Antibodies to Cell Adhesion Antigens LFA–1α and MALA–2,* Transplantation (1991) 52:842–845.
Hartman, et al., *Protection of ischmemic/reperfused canine myocardium by CL18/6, a monoclonal antibody to adhesion molecule ICAM–1,* Cardiovasc. Res. (1995) 30(1):47–54.
Hasagawa, et al., *Prevention of autoimmune insulin–dependent diabetes in non–obese diabetic mice by anti–LFA–1 and anti–ICAM–1 mAb,* Int. Immunol, (1994) 6:831–838.
He, et al., *Effect of LFA–1 and ICAM–1 Antibody Treatment on Murine Corneal Allograft Survival,* Opthalmol. Vis. Sci., (1994) 35: 3218–3225.

Henricks, P.A., *Pharmacological modulation of cell adhesion molecules,* Eur. J. Pharmacol. (1998) 344:1–13.

Herrold, et al., *Prevention of Autoimmune Diabetes by Treatment with Anti–LFA–1 and anti–ICAM–1 Monoclonal Antibodies,* Cell Immunol. (1994) 157:489–500.

Horgan, et al., *Role of ICAM–1 in Neutrophil–Mediated Lung Vascular injury after occlusion and Reperfusion,* Am J Physiol, 261(5):H1578–H1584, 1991.

Huang, C., *A Binding Interface on the I Domain of Lymphocyte Function–associated Antigen–1 (LFA–1) Requirecd for Specific Interaction with Intercellular Adhesion Molecule 1 (ICAM–1),* J. Biol. Chem. (1995) 270:19008–19016.

Huth, J.R., *NMR and Mutagenesis Evidence for an I Domain Allosteric Site That Regulates Lymphocyte Function–associated Antigen 1 Ligand Binding.* Proc. Natl. Acad. Sci., USA (2000) 97:5231–5236.

Isobe, et al., *Specific Acceptance of Cardiac Allograft After Treatment with Antibodies to ICAM–1 and LFA–1,* Science (1992) 255: 1125–1127.

Kakimoto, et al., *The Effect of Anti–Adhesion Molecule Antibody on the Development of Collagen–Induced Arthritis,* Cell Immunol. (1992) 142:326–337.

Kallen, J., et al., *Structural Basis for LFA–1 Inhibition upon Lovastatin Binding to the CD11a I–Domain,* J. Mol. Biol. (1999) 292–1–9.

Kawasaki, et al., *Antibodies against Intercellular Adhesion Molecule–1 and Lymphocyte Function–Associated Antigen–1 Prevent Glomerular Injury in Rat Experimental Crescentic Glomerulonephritis,* J. Immunol. (1993) 150:1074–1083.

Kelly, T. A., *Cutting Edge: A Small Molecule Antagonist of LFA–1–Mediated Cell Adhesion,* J. Immunol. (1999) 163:5173–5177.

Kishimoto, T. K., *Integrins, ICAMs and Selectins: Role and Regulation of Adhesion Molecules in Neutrophil Recruitment to Inflammatory Sites,* Adv. Pharmacol. (1994) 25:117–169.

Knoerzer, et al., *Clinical and Histological Assessment of Collagen–Induced Arthritis Progression in the Diabetes–Resistant BB/Wor Rat,* Toxicol. Pathol. (1997) 25:13–19.

Landis, R. C., *Involvement of The "I" domain of LFA–1 in Selective Binding to Ligands ICAM–1 and ICAM–3,* J. Cell Biol. (1994) 126:529–537.

Lawrence, M. B., Springer, T.A., *Leukocytes' Roll on a Selectin in Physiologic Flow Rate: Distinction from and Prerequisite for Adhesion Through Integrins,* Cell (1991) 65:859–873.

Ley, K., et al., *Lectin–Like Cell Adhesion Molecule 1 Mediates Rolling in Mesenteric Venules, in vivo,* Blood (1991) 77:2553–2555.

Link, J. T., et al., *Discovery and SAR of Diarylsulfide Cyclopropylamide LFA–1/ICAM–1 Interaction Antagonists,* Bioorg. Med. Chem Lett. (2001) 11:973–976.

Liu, G., *Small Molecule Antagonists of the LFA–1/ICAM–1 Interaction as Potential Therapeutic Agents,* Expert Opin. Ther. Patents (2001) 11(9):1383–1393.

Liu, G., et al., *Discovery of Novel P–arylthio Cinnamides as Antogonists of Leukocyte Function–associated Antigen–1/intracellular Adhesion Molecule–1 Interaction, 1. Identification of an Additional Binding Pocket Based on an Anilino Diaryl Sulfide Lead.* J. Med. Chem. (2000) 43:4025–4040.

Liu, G., et al., *Novel P–arylthio Cinnamides as Antagonists of Leukocyte Function–associated Antigen–1/intracellular Adhesion Molecule–1 Interaction. 2. Mechanism of Inhibition and Structure–based Improvement of Pharmaceutical Properties.* (2001) J. Med. Chem. 44:1202–1210.

Lu, C., et al., *An isolated, Surface–expressed I Domain of the Integrin AIβ2 Is Sufficient for Strong Adhesive Function When Locked in the Open Conformation with a Disulfide Bond.* Proc. Natl. Acad. Sci. USA (2001) 98–2387–2392.

Mulligan, et al., *Compartmentalized Roles for Leukocyctic Adhesion Molecules in Lung Inflammatory Injury,* J. Immunol. (1995) 154:1350–1363.

Nagase, et al., *Intercellular Adhesion Molecule–1 Mediates Acid Aspiration–induced Lung Injury,* Am. J. Respir. Crit. Care Med. (1996) 154:504–510.

Nakano, T., et al., *Adxanthromycins A and B, New Inhibitors of ICAM–1/ILFA–1 Mediated Cell Adhesion Molecule from Streptomyces sp NA–148,* J. Antibos. (Tokyo) (2000) 53:12–18.

Nakao, et al., *Monoclonal Antibodies Against ICAM–1 and LFA–1 Prolong Nerve Allograft Survival,* Muscle Nerve (1995) 18:93–102.

Oppenheimer–Marks, et al., *Interleukin 15 Is Produced by Endothelial Cells and Increases the Transendothelial Migration of T Cells In Vitro and in the SCID Mouse–Human Rheumatoid Arthritis Model In Vivo,* J. Clin. Invest. (1998) 101:1261–1272.

Panes, et al., *Role of Leukocyte–Endothelial Cell Adhesion in Radiation–Induced Microvascular Dysfunction in Rats,* Gastroenterology (1995) 108:1761–1769.

Pei, Z., et al., *Discovery of Potent Antagonists of Leukocyte Function–associated Antigen–1/intercellular Adhesion Molecule–1 Interaction. 3. Amide (C–ring) Structure–activity Relationship and Improvement of Overall Properties of Arylthio–Cinnamides.* J. Med. Chem. (2001) 44:2913–2920.

Prescott, E., *Methods in Cell Biology,* vol. XIV, Academic Press, New York, NY (1976), p. 33 et seq.

Qu, A., et al., *The Role of the Divalent Cation in the Structure of the I Domain from the CD11a/CD18 Integrin,* Structure (1996) 4:931–942.

Roche, E. B., *Bioreversible Carriers in Drug Design,* American Pharmaceutical Association and Pergamon Press, 1987.

Sanfilippo, P.J., *Novel Thiazole Based Heterocycles as Inhibitors of LFA–1/ICAM–1 Mediated Cell Adhesion,* J. Med. Chem. (1995) 38:1057–1059.

Springer, T.A., *Adhesion Receptors of the Immune System,* Nature (1990) 346:425–434.

Springer, T.A., *Traffic Signals for Lymphocyte Recirculation and Leukocyte Emigration: The Multistep Paradigm,* Cell (1994) 76:301–314.

Stanley, P., et al., *The I Domain of Integrin LFA–1 interacts with ICAM–1 Domain 1 at Residue Glu–34 But Not Gln–73,* J. Biol. Chem. (1998) 273:3358–3362.

Schimmer, et al., *Streptococcal Cell Well–Induced Arthritis: Requirements for IL–4, IL–10, IFN–γ, and Monocyte Chemoattractant Protein–1,* J. Immunol. 91998) 160:1455–1477.

Talento, et al., *A Single Administration of LFA–1 Antibody Confers Prolonged Allograft Survival,* Transplantation (1993) 55:418–422.

Tamiya, et al., *Protective effect of monoclonal antibodies against LFA–1 and ICAM–1 on myocardial reperfusion injury following global ischemia in rat hearts,* Immunopharmacology, 29(1):53–63, 1995.

Tanaka, et al., *Inhibition of Inflammatory Liver injury by a Monoclonal Antibody against Lymphocyte Function–Associated Antigen–1,* J. Immunol. (1993) 151:5088–5095.

von Adrian, et al., *Two–Step Model of Leukocyte–Endothelial Cell Interaction in Inflammation: Distinct roles for LECAM–1 and the leukocyte* $\beta_2$*integrins in vivo,* Proc. Natl. Acad. Sci. USA (1991) 88:7538–7542.

Wegner, et al., *Intercellular Adhesion Molecule–1* (*ICAM–1*) *in the Pathogenesis of Asthma,* Science (1990) 247:456–459, 1990.

Wegner, et al., *Intercellular Adhesion Molecule–1 Contributes to Pulmonary Oxygen Toxicity in Mice: Role of Leukocytes Revised,* Lung (1992) 170: 267–279.

Winn, Martin et al., *Discovery of Novel p–Arylthio Cinnamides as Antagolists of Leukocyte Function–Associated Antigen–1/Intercellular Adhesion Molecule–1 Interaction. 4. Structure–Activity Relationship of Substituents on the Benzene Ring of the Cinnamide,* J. Med. Chem. (2001) 44:4393.

Zeng, et al., *Inhibition of Transplant Rejection by Pretreatment of Xenogeneic Pancreative Islet Cells with Anti–ICAM–1 Antibodies,* Transplantation (1994)58: 681–689.

Zhu, G., et al., *Diels–Alder Reactions of Hexafluoro–w–butyne with 2–Heterosubstituted Furans: A Facile and General Synthesis of 1,4 Disubstituted 2,3–Di*[*trifluoromethyl*] *benzenes,* Organic Letters (2000) 2(21):3345.

International Search Report for PCT Application No. PCT US 99/31162.

International Search Report for PCT Application No. PCT US 00/08895.

* cited by examiner

CELL ADHESION-INHIBITING ANTIINFLAMMATORY AND IMMUNE-SUPPRESSIVE COMPOUNDS

Matter enclosed in heavy brackets [ ] appears in the original patent but forms no part of this reissue specification; matter printed in italics indicates the additions made by reissue.

TECHNICAL FIELD

The present invention relates to compounds that are useful for treating inflammatory and immune diseases, to pharmaceutical compositions comprising these compounds, and to methods of inhibiting inflammation or suppressing immune response in a mammal.

BACKGROUND OF THE INVENTION

Inflammation results from a cascade of events that includes vasodilation accompanied by increased vascular permeability and exudation of fluid and plasma proteins. This disruption of vascular integrity precedes or coincides with an infiltration of inflammatory cells. Inflammatory mediators generated at the site of the initial lesion serve to recruit inflammatory cells to the site of injury. These mediators (chemokines such as IL-8, MCP1, MIP-1, and RANTES, complement fragments and lipid mediators) have chemotactic activity for leukocytes and attract the inflammatory cells to the inflamed lesion. These chemotactic mediators which cause circulating leukocytes to localize at the site of inflammation require the cells to cross the vascular endothelium at a precise location. This leukocyte recruitment is accomplished by a process called cell adhesion.

Cell adhesion occurs through a coordinately regulated series of steps that allow the leukocytes to first adhere to a specific region of the vascular endothelium and then cross the endothelial barrier to migrate to the inflamed tissue (Springer, T. A., [1994,] "Traffic Signals for Lymphocyte Recirculation and Leukocyte Emigration: The Multistep Paradigm, [Cell]" *Cell* (*1994*) 76:301–314; Lawrence, M. B., and Springer, T. A., [1991,] "Leukocytes['] Roll on a Selectin at Physiologic Flow Rates: Distinction from and Prerequisite for Adhesion Through Integrins, [Cell.]" *Cell* (*1991*) 65:859–873; Von Adrian, U., Chambers, J. D., McEnvoy, L. M., Bargatze, R. F., Arfos, K. E. and Butcher, E. C., [1991,] "Two-Step Model of Leukocyte-Endothelial Cell Interactions in Inflammation, [Proc. Natl. Acad. Sci. USA]" *Proc. Natl. Acad. Sci. USA* (*1991*) 88: 7538–7542; and Ley, K., Gaehtgens, P., Fennie, C., Singer, M. S., Lasky, L. H. and Rosen, S. D., [1991,] "Lectin-Like Cell Adhesion Molecule 1 Mediates Rolling in Mesenteric Venules [in vivo, Blood] *In Vivo," Blood* (*1991*) 77: 2553–2555). These steps are mediated by families of adhesion molecules such as integrins, Ig supergene family members, and selectins which are expressed on the surface of the circulating leukocytes and on the vascular endothelial cells. The first step consists of leukocytes rolling along the vascular endothelial cell lining in the region of inflammation. The rolling step is mediated by an interaction between a leukocyte surface oligosaccharide, such as Sialylated Lewis-X antigen (Slex), and a selectin molecule expressed on the surface of the endothelial cell in the region of inflammation. The selectin molecule is not normally expressed on the surface of endothelial cells but rather is induced by the action of inflammatory mediators such as TNF-α and interleukin-1. Rolling decreases the velocity of the circulating leukocyte*s* in the region of inflammation and allos the cells to more firmly adhere to the endothelial cell. The firm adhesion is accomplished by the interaction of integrin molecules that are present on the surface of the rolling leukocytes and their counter-receptors (the Ig superfamily molecules) on the surface of the endothelial cell. The Ig superfamily molecules or CAMs (Cell Adhesion Molecules) are either not expressed or are expressed at low levels on normal vascular endothelial cells. The [CAM's] *CAMs*, like the selectins, are induced by the action of inflammatory mediators like TNF-alpha and IL-1. The final event in the adhesion process is the extravasation of leukocytes through the endothelial cell barrier and their migration along a chemotactic gradient to the site of inflammation. This transmigration is mediated by the conversion of the leukocyte integrin from a low avidity state to a high avidity state. The adhesion process relies on the induced expression of selectins and [CAM's] *CAMs* on the surface of vascular endothelial cells to mediate the rolling and firm adhesion of leukocytes to the vascular endothelium.

The interaction of the intercellular adhesion molecule ICAM-1 (cd54) on endothelial cells with the integrin LFA-1 on leukocytes plays an important role in endothelial-leukocyte contact. Leukocytes bearing high-affinity LFA-1 adhere to endothelial cells through interaction with ICAM-1, initiating the process of extravasation from the vasculature into the surrounding tissues. Thus, an agent which blocks the ICAM-1/LFA-1 interaction suppresses these early steps in the inflammatory response. Consistent with this background, ICAM-1 knockout mice have numerous abnormalities in their inflammatory responses.

The present [invention] *application* discloses compounds which bind to the interaction-domain [(1-domain)] (*I-domain*) of LFA-1, thus interrupting endothelial cell-leukocyte adhesion by blocking the interaction of LFA-1 with ICAM-1, ICAM-3, and other adhesion molecules. These compounds are useful for the treatment of prophylaxis of diseases in which leukocyte trafficking plays a role, notably acute and chronic inflammatory diseases, autoimmune diseases, tumor metastasis, allograft rejection, and reperfusion injury. The compounds of this invention are diaryl sulfides, which are substituted with a cinnamide moiety. The cinnamide functionality may be placed either ortho- or para- to the linking sulfur atom, although para-substitution is preferable. Appropriate substitution of both aromatic rings is tolerated, and can be used to modulate a variety of biochemical, physicochemical and pharmacokinetic properties. In particular the amide moiety is readily modified; a variety of secondary and tertiary amides are active, and alternatively a heterocyclic ring may be attached at this position. Modifications of this amide functionality are particularly useful in modulating physico-chemical and pharmacokinetic properties.

SUMMARY OF THE INVENTION

In one embodiment of the present invention are disclosed compounds represented by structural Formula I, below, Formula I

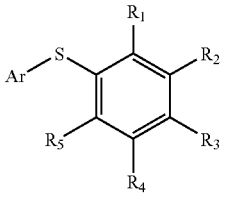

or a pharmaceutically-acceptable salt or *pharmaceutically-acceptable* prodrug [thereof] *of a compound of Formula I*,

[wherein $R_1$, $R_2$, $R_3$, $R_4$, and $R_5$ are independently selected from a. hydrogen,
b. halogen,
c. alkyl,
d. haloalkyl,
e. alkoxy,
f. cyano,
g. nitro,
h. carboxaldehyde, and]

[with the proviso that at least] *where* one *or both* of $R_1$ [or] *and* $R_3$, *which may be the same or different,* is a "cis-cinnamide" or a "trans-cinnamide", defined as

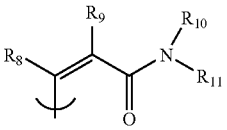

"cis-cinnamide"

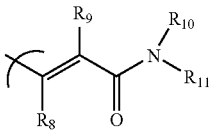

"trans-cinnamide"

[wherein] *where* $R_8$ and $R_9$ are *each* independently selected from a. hydrogen, [and]
b. alkyl,
c. carboxy[ ]alkyl,
d. [alkylaminocarbonyl alkyl] *monoalkylaminocarbonylalkyl*, and
e. dialkylaminocarbonyl[ ]alkyl, and $R_{10}$ and $R_{11}$ are *each* independently selected from a. hydrogen,
b. alkyl,
c. cycloalkyl,
d. alkoxycarbonylalkyl,
e. hydroxyalkyl, and
f. heterocyclylalkyl, or [where $NR_{10}R_{11}$ is] *$R_{10}$ and $R_{11}$ are taken together with the N to form an unsubstituted* heterocyclyl *group,* or *a* substituted heterocyclyl *group, where the substituted heterocyclyl group is substituted by one or more than one substituent*, where *the* substituents are *each* independently selected from 1) alkyl,
2) alkoxy,
3) alkoxyalkyl,
4) cycloalkyl,
5) aryl,
6) heterocyclyl,
7) heterocyclylcarbonyl,
8) heterocyclylalkylaminocarbonyl,
9) hydroxy,
10) hydroxyalkyl,
11) hydroxyalkoxyalkyl,
12) carboxy,
13) carboxycarbonyl,
14) carboxaldehyde,
15) alkoxycarbonyl,
16) arylalkoxycarbonyl,
17) aminoalkanoyl,
18) carboxamido,
19) alkoxycarbonylalkyl,
20) carboxamidoalkyl,
21) alkanoyl,
22) hydroxyalkanoyl,
23) alkanoyloxy,
24) alkanoylamino,
25) alkanoyloxyalkyl, and
26) alkylsulfonyl,

*$R_1$, if it is not "cis-cinnamide" or "trans-cinnamide", as defined above, $R_3$, if it is not "cis-cinnamide" or "trans-cinnamide", as defined above, $R_2$, $R_4$, and $R_5$, are each independently selected from*

*a. hydrogen,*
*b. halogen,*
*c. alkyl,*
*d. haloalkyl,*
*e. alkoxy,*
*f. cyano,*
*g. nitro, and*
*h. carboxaldehyde,* and [wherein] Ar is *an unsubstituted aryl group, an unsubstituted heteroaryl group,* a substituted aryl *group,* or *a* substituted heteroaryl group, *where the substituted aryl group and the substituted heteroaryl group are substituted by one or more than one substituent,* where [substitutions] *the substituents* are *each* independently selected from

[a. hydrogen,]
[b.] *a.* halogen,
[c.] *b.* alkyl,
[d.] *c.* aryl,
[e.] *d.* haloalkyl,
[f.] *e.* hydroxy,
[g.] *f.* alkoxy,
[h.] *g.* alkoxycarbonyl,
[i.] *h.* alkoxyalkoxy,
[j.] *i.* hydroxyalkyl,
[k.] *j.* aminoalkyl,
[l.] *k.* alkyl(alkoxycarbonylalkyl)aminoalkyl,
[m.] *l. unsubstituted* heterocyclylalkyl,
[n.] *m.* substituted heterocyclylalkyl,
[o.] *n.* carboxaldehyde,
[p.] *o.* carboxaldehyde hydrazone,
[q.] *p.* carboxamide,
[r.] *q.* alkoxycarbonyl[ ]alkyl,
[s.] *r.* hydroxycarbonylalkyl[ ](carboxyalkyl),
[t.] *s.* cyano,
[u.] *t.* amino,
[v.] *u.* heterocyclylalkylamino, and
[w.] *v.* "trans-cinnamide"[.],

*subject to the proviso that when $R_3$ is a "cis-cinnamide" or a "trans-cinnamide," as defined above, one or more than one of the following conditions is fulfilled:*

*(A) Ar is an unsubstituted heteroaryl group, a substituted heteroaryl group, or a substituted aryl group;*

(*B*) *one or more than one of* $R_1$, $R_2$, $R_4$, *and* $R_5$, *as defined above, are other than hydrogen; and*

(*C*) $R_{10}$ *and* $R_{11}$ *are taken together with N to form a substituted or unsubstituted heterocyclyl group, as defined above.*

In another embodiment of the invention are disclosed compounds represented by structural Formula I, above, when prepared by synthetic processes or by metabolic processes. Preparation of the compounds of the present invention by metabolic processes include those occurring in the human or animal body (in vivo) or by processes occurring in vitro.

In another embodiment of the invention are disclosed methods of treatment or prophylaxis in which the inhibition of inflammation or suppression of immune response is desired, comprising administering an effective amount of a compound having Formula I.

In yet another embodiment of the invention are disclosed pharmaceutical compositions containing compounds of Formula I.

DETAILED DESCRIPTION OF THE INVENTION

Definition of Terms

The term "alkanoyl" as used herein refers to an alkyl group attached to the parent molecular group through a carbonyl group.

The term "alkanoylamino" as used herein refers to an alkanoyl group attached to the parent molecular group though an amino group.

The term "alkanoyloxy" as used herein refers to an alkanoyl group attached to the parent molecular group through an oxygen radical.

The term "alkanoyloxyalkyl" as used herein refers to an alkanoyloxy group attached to the parent molecular group through an alkyl group.

The term "alkoxy" as used herein refers to an alkyl group attached to the parent molecular group through an oxygen atom.

The term "alkoxyalkoxy" as used herein refers to an alkoxy group attached to the parent molecular group through an alkoxy group.

The term "alkoxyalkyl" as used herein refers to an alkoxy group attached to the parent molecular group through an alkyl group.

The term "alkoxycarbonyl" as used herein refers to an alkoxy group attached to the parent molecular group through a carbonyl group.

The term "alkoxycarbonylalkyl" as used herein refers to an alkoxycarbonyl group attached to the parent molecular group through an alkyl group.

The term "alkyl" as used herein refers to a saturated straight or branched chain *radical* group of 1–10 carbon atoms derived from an alkane by the removal of one hydrogen atom.

The term "alkyl(alkoxycarbonylalkyl)amino" as used herein refers to an amino group substituted with one alkyl group and one alkoxycarbonylalkyl group.

The term "alkyl(alkoxycarbonylalkyl)aminoalkyl" as used herein refers to an alkyl(alkoxycarbonylalkyl)amino group attached to the parent molecular group through an alkyl group.

The term "alkylene" as used herein refers to a divalent group of 1–10 carbon atoms derived from a straight or branched chain alkane by the removal of two hydrogen atoms.

The term "alkylsulfonyl" as used herein refers to an alkyl radical attached to the parent molecular group through an —$SO_2$— group.

The term "amino" as used herein refers to a radical of the form —$NR_{18}R_{19}$, or to to a radical of the form —$NR_{18}$—, where $R_{18}$ and $R_{19}$ are independently selected from hydrogen, alkyl or cycloalkyl.

The term "aminoalkanoyl" as used herein refers to to an amino group attached to the parent molecular group through an alkanoyl group.

The term "aminoalkyl" as used herein refers to an amino group attached to the parent molecular group through an alkyl group.

The term "aryl" as used herein refers to a mono- or bicyclic carbocyclic ring system having one or two aromatic rings. The aryl group can also be fused to a cyclohexane, cyclohexene, cyclopentane or cyclopentene ring. The aryl groups of this invention can be optionally substituted with alkyl, halogen, hydroxy, or alkoxy substituents.

The term "arylalkoxy" as used herein refers to an aryl group attached to the parent molecular group through an alkoxy group.

The term "arylalkoxycarbonyl" as used herein refers to an arylalkoxy group attached to the parent molecular group through a carbonyl group.

The term "carboxaldehyde" as used herein refers to the radical —CHO.

The term "carboxaldehyde hydrazone" as used herein refers to the radical —CH═N—$NR_{20}R_{21}$, where $R_{20}$ and $R_{21}$ are independently selected from hydrogen, alkyl or cycloalkyl.

The terms "carboxamide" or "carboxamido" as used herein refer to an amino group attached to the parent molecular group through a carbonyl group.

The term "carboxamidoalkyl" as used herein refers to a carboxamido group attached to the parent molecular group through an alkyl group.

The term "carboxy" as used herein refers to the radical —COOH.

The term "carboxycarbonyl" as used herein refers to a carboxy group attached to the parent molecular group through a carbonyl group.

The term "cyano" as used herein refers to the radical —CN.

The term "cycloalkyl" as used herein refers to a monovalent saturated cyclic or bicyclic hydrocarbon group of 3–12 carbons derived from a cycloalkane by the removal of a single hydrogen atom. Cycloalkyl groups may be optionally substituted with alkyl, alkoxy, halo, or hydroxy substituents.

The terms "halo" or "halogen" as used herein refers to F, Cl, Br, or I.

The term "haloalkyl" as used herein refers to an alkyl group substituted with one or more halogen atoms.

The terms "heterocycle" or "heterocyclyl" represent a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" or "heterocyclic" as used herein additionally refers to bicyclic, tricyclic and tetracyclic groups in which any of the above heterocyclic rings is fused to one or two rings independently selected from an aryl ring, a cyclohexane ring, a cyclohexane ring, a cyclopentane ring, a cyclopenetene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadizolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl,triazolyl, and the like.

Heterocyclics also include bridged bicyclic groups where a monocyclic heterocyclic group is bridged by an alkylene group such as

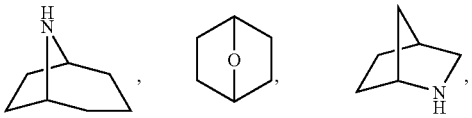

and the like.

Heterocyclics also include compounds of the formula

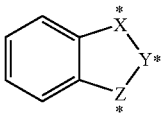

where X* and Z* are independently selected from —$CH_2$—, —$CH_2NH$—, —$CH_2O$—, —NH— and —O—, with the proviso that at least one of X* and Z* is not —$CH_2$—, and Y* is selected from —C(O)— and —$(C(R'')_2)_v$—, where R" is hydrogen or alkyl of one to four carbons, and v is 1–3. These heterocycles include 1,3-benzodioxolyl, 1,4-benzodioxanyl, 1,3-benzimidazol-2-one and the like. The heterocycle groups of this invention can be optionally substituted with alkyl, halogen, hydroxy or alkoxy substituents.

The term "heterocyclylalkyl" as used herein refers to an heterocyclic group attached to the parent molecular group through an alkyl group.

The term "heterocyclylalkylamino" as used herein refers to an heterocyclylalkyl group attached to the parent molecular group through an amino group.

The term "heterocyclylalkylaminocarbonyl" as used herein refers to a heterocyclylalkylamino group attached to the parent molecular group through a carbonyl group.

The term "heterocyclylcarbonyl" as used herein refers to a heterocyclyl group attached to the parent molecular group through a carbonyl group.

The term "hydroxyalkanoyl" as used herein refers to an hydroxy radical attached to the parent molecular group through an alkanoyl group.

The term "hydroxyalkoxy" as used herein refers to an hydroxy radical attached to the parent molecular group through an alkoxy group.

The term "hydroxyalkoxyalkyl" as used herein refers to an hydroxyalkoxy group attached to the parent molecular group through an alkyl group.

The term "hydroxyalkyl" as used herein refers to an hydroxy radical attached to the parent molecular group through an alkyl group.

The term "perfluoroalkyl" as used herein refers to an alkyl group in which all of the hydrogen atoms have been replaced by fluoride atoms.

The term "phenyl" as used herein refers to a monocyclic carbocyclic ring system having one aromatic ring. The phenyl group can also be fused to a cyclohexane or cyclopentane ring. The phenyl groups of this invention can be optionally substituted with alkyl, halogen, hydroxy or alkoxy substituents.

The term "pharmaceutically-acceptable prodrugs" as used herein represents those prodrugs of the compounds of the present invention which are, within the scope of sound medical judgment, suitable for use in contact with the tissues of humans and lower animals [with] *without* undue toxicity, irritation, allergic response, and the like, commensurate with a reasonable benefit/risk ratio, and effective for their intended use, as well as the zwitterionic forms, where possible, of the compounds of the invention.

The term "prodrug", as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "thioalkoxy" as used herein refers to an alkyl group attached to the parent molecular group through a sulfur atom.

Compounds of the present invention can exist as stereoisomers wherein asymmetric or chiral centers are present. These compounds are designated by the symbols "R" or "S," depending on the configuration of substituents around the chiral carbon atom. The present invention contemplates various stereoisomers and mixtures thereof. Stereoisomers include enantiomers and diastereomers, and mixtures of enantiomers or diastereomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a carbocyclic ring. Substituents around a carbon-carbon double bond are designated as being in the Z or E configuration wherein the term "Z" represents substituents on the same side of the carbon-carbon double bond and the term "E" represents substituents on opposite sides of the carbon-carbon double bond. The arrangement of substituents around a carbocyclic ring are designated as cis or trans wherein the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated cis/trans.

As is apparent from the foregoing descriptions, the compounds of Formula I are useful in a variety of forms, i.e., with various substitutions as identified. Examples of particularly desirable compounds are quite diverse, and many are mentioned herein. Included are compounds in which $R_1$ is a "cis-cinnamide" or a "trans-cinnamide", and $R_3$ is hydrogen; or where $R_3$ is a "cis-cinnamide" or a "trans-cinnamide", and $R_1$ is hydrogen, or $R_1$, $R_2$, and $R_4$ are each independently hydrogen or alkyl, and $R_5$ is halogen, haloalkyl or nitro. Further preferred compounds include those as above wherein $R_{10}$ and $R_{11}$ are each in dependently hydrogen, alkyl, cycloalkyl, alkoxycarbonylaalkyl, hydroxyalkyl, or heterocyclylalkyl, or where $NR_{10}R_{11}$, is heterocyclyl or substituted heterocyclyl, and where Ar is aryl, substituted aryl, heteroaryl, or substituted heteroaryl.

Compounds of the present invention include, but are not limited to:

(2,4-Dichlorophenyl)[2-(E-((6-hydroxyhexylamino) carbonyl)ethenyl)phenyl]sulfide;

(2,4-Dichlorophenyl)[2-E-((3-(1-imidazolyl)propylamino) carbonyl)ethenyl)phenyl]sulfide;

(2,4-Dichlorophenyl)[2-chloro-4-(E-((2-hydroxyethylamino)carbonyl)ethenyl)phenyl]sulfide;

(2,4-Dichlorophenyl)[2-chloro-4-(E-((6-hydroxyhexylamino)carbonyl)ethenyl)phenyl]sulfide;

(2,4-Dichlorophenyl)[2-chloro-4-(E-((bis-(2-hydroxyethyl) amino)carbonyl)ethenyl)phenyl]sulfide;

[(2,4-Dichlorophenyl)[2-chloro-4-(E-((3-(1-pyrrolidin-2-only)propylamino)carbonyl)ethenyl)phenyl]sulfide;]

*(2,4-Dichlorophenyl)[2-chloro-4-(E-((3-(2-oxopyrrolidin-1-yl)propylamino)carbonyl)ethenyl)phenyl]sulfide;*

(2,4-Dichlorophenyl)[2-chloro-4-(E-((1-morpholinyl) carbonyl)ethenyl)phenyl]sulfide;

(2,4-Dichlorophenyl)[2-chloro-4-(E-((4-methylpiperazin-1-yl)carbonyl)ethenyl)phenyl]sulfide;

(2,4-Dichlorophenyl)[2-chloro-4-(E-((4-acetylpiperazin-1-yl)carbonyl)ethenyl)phenyl]sulfide;

(2,4-Dichlorophenyl)[2-chloro-4-(E-((4-(2-pyridyl) piperazin-1-yl)carbonyl)ethenyl)phenyl]sulfide;

(2-(Hydroxymethyl)phenyl)[2-chloro-4-(E-((1-morpholinyl)carbonyl)ethenyl)phenyl]sulfide;

(2-Bromophenyl)[2-chloro-4-(E-((1-morpholinyl)carbonyl) ethenyl)phenyl]sulfide;

(2,4-Dichlorophenyl)[2-chloro-4-(E-((4-(2-hydroxyethyl) piperazin-1-yl)carbonyl)ethenyl)phenyl]sulfide;

(2,4-Dichlorophenyl)[2-chloro-4-(E-((4-(2-hydroxyethoxyethyl)piperazin-1-yl)carbonyl)ethenyl) phenyl]sulfide;

(2-Bromophenyl)[2-chloro-4-(E-((3-(hydroxymethyl) piperidin-1-yl)carbonyl)ethenyl)phenyl]sulfide;

(2-Bromophenyl)[2-chloro-4-(E-((2-(hydroxymethyl) piperidin-1-yl)carbonyl)ethenyl)phenyl]sulfide;

(2-Bromophenyl)[2-chloro-4-(E-((3-acetamidopyrrolidin-1-yl)carbonyl)ethenyl)phenyl]sulfide;

(2-Bromophenyl)[2-chloro-4-(E-((4-(hydroxypiperidin-1-yl)carbonyl)ethenyl)phenyl]sulfide;

(2-Bromophenyl)[2-chloro-4-(E-((piperidin-1-yl)carbonyl) ethenyl)phenyl]sulfide;

(2,4-Dichlorophenyl)[2-chloro-4-(E-((3-carboxypiperidin-1-yl)carbonyl)ethenyl)phenyl]sulfide;

(2,4-Dichlorophenyl)[2-chloro-4-(E-((4-carboxypiperidin-1-yl)carbonyl)ethenyl)phenyl]sulfide;

(2-Bromophenyl)[2-chloro-4-(E-((4-acetylhomopiperazin-1-yl)carbonyl)ethenyl)phenyl]sulfide;

(2-Bromophenyl)[2-chloro-4-(E-((thiomorpholin-1-yl) carbonyl)ethenyl)phenyl]sulfide;

[(2-Bromophenyl)[2-chloro-4-(E-((4-(1-benzimidazol-2-only)piperidin-1-yl)carbonyl)ethenyl)phenyl]sulfide;]

*(2-Bromophenyl)2-chloro-4-(E-((4-(2-oxo-2,3-dihydro-1H-benzimidazol-1-yl)piperidin-1-yl)carbonyl)ethenyl) phenyl]sulfide;*

(2-Bromophenyl)[2-chloro-4-(E-((2-tetrahydroisoquinolinyl)carbonyl)ethenyl)phenyl]sulfide;

(2-Methylphenyl)[2-trifluoromethyl-4-(E-((4-acetylpiperazin-1-yl)carbonyl)ethenyl)phenyl]sulfide;

(2-Methylphenyl)[2-trifluoromethyl-4-(E-((1-morpholinyl) carbonyl)ethenyl)phenyl]sulfide;

[(2-Methyliphenyl)[2-trifluoromethyl-4-(E-((2-(-morpholinyl)ethylamino)carbonyl)ethenyl)phenyl] sulfide;]

*(2-Methylphenyl)[2-trifluoromethyl-4-(E-((2-(1-morpholinyl)ethylamino)carbonyl)ethenyl)phenyl] sulfide;*

(2-Methylphenyl)[2-trifluoromethyl-4-(E-((4-phenylpiperazin-1-yl)carbonyl)ethenyl)phenyl]sulfide;

[(2-Methylphenyl)[2-trifluoromethyl-4-(E-((3-(1-pyrrolidin-2-only)propylamino)carbonyl)ethenyl)phenyl] sulfide;]

*(2-Methylphenyl)[2-trifluoromethyl-4-(E-((3-(2-oxopyrrolidin-1-yl)propylamino)carbonyl)ethenyl) phenyl]sulfide;*

(2-Methylphenyl)[2-trifluoromethyl-4-(E-((cyclopropylamino)carbonyl)ethenyl)phenyl]sulfide;

(2,4-Dichlorophenyl)[2-nitro-4-(E-((4-acetylpiperazin-1-yl) carbonyl)ethenyl)phenyl]sulfide;

[(2,4-Dichlorophenyl)[2-nitro-4-(E-((3-(1-pyrrolidin-2-only)propylamino)carbonyl)ethenyl)phenyl]sulfide;]

*(2,4-Dichlorophenyl)2-nitro-4-(E-((3-(2-oxopyrrolidin-1-yl)propylamino)carbonyl)ethenyl)phenyl]sulfide;*

(2,3-Dichlorophenyl)[2-nitro-4-(E-((4-acetylpiperazin-1-yl) carbonyl)ethenyl)phenyl]sulfide;

(4-Bromophenyl)[2-nitro-4-(E-((4-acetylpiperazin-1-yl) carbonyl)ethenyl)phenyl]sulfide;

(4-Methylphenyl)[2-chloro-4-(E-((4-acetylpiperazin-1-yl) carbonyl)ethenyl)phenyl]sulfide;

(2,4-Dichlorophenyl)[2-nitro-4-(E-((4-(tert-butoxycarbonyl)piperazin-1-yl)carbonyl)ethenyl)phenyl] sulfide;

(2,4-Dichlorophenyl)[2-nitro-4-(E-((4-(2-furoylcarbonyl) piperazin-1-yl)carbonyl)ethenyl)phenyl]sulfide;

(2,4-Dichlorophenyl)[2-nitro-4-(E-((4-(methanesulfonyl) piperazin-1-yl)carbonyl)ethenyl)phenyl]sulfide;

(2,4-Dichlorophenyl)[2-nitro-4-(E-((4-(diethylaminocarbonylmethyl)piperazin-1-yl)carbonyl) ethenyl)phenyl]sulfide;

(2,4-Dichlorophenyl)[2-nitro-4-(E-((4-(diethylaminocarbonyl)piperazin-1-yl)carbonyl)ethenyl) phenyl]sulfide;

(2,4-Dichlorophenyl)[2-nitro-4-(E-((4-tert-butoxycarbonylmethyl)piperazin-1-yl)carbonyl)ethenyl) phenyl]sulfide;

(2,4-Dichlorophenyl)[2-nitro-4-(E-((4-(carboxycarbonyl) piperazin-1-yl)carbonyl)ethenyl)phenyl]sulfide;

(2,4-Dichlorophenyl)[2-nitro-4-(E-((4-(carboxymethyl) piperazin-1-yl)carbonyl)ethenyl)phenyl]sulfide;

(2-Methylphenyl)[2-nitro-4-(E-((4-acetylpiperazin-1-yl) carbonyl)ethenyl)phenyl]sulfide;

(2-Chlorophenyl)[2-nitro-4-(E-((4-acetylpiperazin-1-yl) carbonyl)ethenyl)phenyl]sulfide;

(2-Aminophenyl)[2-nitro-4-(E-((4-acetylpiperazin-1-yl) carbonyl)ethenyl)phenyl]sulfide;

(2-Hydroxymethyl)phenyl)[2-nitro-4-(E-((4-acetylpiperazin-1-yl)carbonyl)ethenyl)phenyl]sulfide;

(2-Ethylphenyl)[2-nitro-4-(E-((4-acetylpiperazin-1-yl) carbonyl)ethenyl)phenyl]sulfide;

(2-iso-Propylphenyl)[2-nitro-4-(E-((4-acetylpiperazin-1-yl) carbonyl)ethenyl)phenyl]sulfide;

(2-tert-Butylphenyl)[2-nitro-4-(E-((4-acetylpiperazin-1-yl) carbonyl)ethenyl)phenyl]sulfide;

(2-Chlorophenyl)[2-chloro-4-(E-((4-acetylpiperazin-1-yl) carbonyl))2-propenyl)phenyl]sulfide;

(2-(1-Morpholinylmethyl)phenyl)[2-chloro-4-(E-((1-morpholinyl)carbonyl)ethenyl)phenyl]sulfide;

(2-(4-(1,3-Benzodioxolyl-5-methyl)piperazin-1-ylmethyl)phenyl)[2-chloro-4-(E-((1-morpholinyl)carbonyl)ethenyl)phenyl]sulfide;

(2-(4-(iso-Propylaminocarbonylmethyl)piperazin-1-ylmethyl)phenyl)[2-chloro-4-(E-((1-morpholinyl)carbonyl)ethenyl)phenyl]sulfide;

(2-((N-Ethoxycarbonylmethyl-N-methyl)aminomethyl)phenyl)[2-chloro-4-(E-((1-morpholinyl)carbonyl)ethenyl)phenyl]sulfide;

(2-Formylphenyl)[2-chloro-4-(E-((1-morpholinyl)carbonyl)ethenyl)phenyl]sulfide;

(2-(4-Formylpiperazin-1-ylmethyl)phenyl)[2-chloro-4-(E-((1-morpholinyl)carbonyl)ethenyl)phenyl]sulfide;

(2-(E-((1-Morpholinyl)carbonyl)ethenyl)phenyl)[2-chloro-4-(E-((1-morpholinyl)carbonyl)ethenyl)phenyl]sulfide;

(2-Formylphenyl)[2-nitro-4-(E-((4-acetylpiperazin-1-yl)carbonyl)ethenyl)phenyl]sulfide;

(2-Formylphenyl)[2-chloro-4-(E-((1-morpholinyl)carbonyl)ethenyl)phenyl]sulfide, N,N-dimethyl hydrazone;

(2-((3-(1-Morpholinyl)propyl)-1-amino)phenyl)[2-chloro-4-(E-((1-morpholinyl)carbonyl)ethenyl)phenyl]sulfide;

[(2,4-Dichlorophenyl)[2-bromo-4-(E-((3-(1-pyrrolidin-2-only)propylamino)carbonyl)ethenyl)phenyl]sulfide;]

*(2,4-Dichlorophenyl)[2-bromo-4-(E-((3-(2-oxopyrrolidin-1-yl)propylamino)carbonyl)ethenyl)phenyl]sulfide;*

(2,4-Dichlorophenyl)[2-formyl-4-(E-((1-morpholinyl)carbonyl)ethenyl)phenyl]sulfide; and (2-Chloro-6-formylphenyl)[2-chloro-4-(E-((4-acetylpiperazin-1-yl)carbonyl)ethenyl)phenyl]sulfide.

Pharmaceutical Compositions and Methods of Treatment

The present invention also provides pharmaceutical compositions which comprise compounds of the present invention formulated together with one or more pharmaceutically-acceptable carriers.The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as [preservative] *preservatives*, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like[,]. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and ([l]*i*) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifing and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers sucha s cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology Volume XIV, Academic Press, New York, N.Y. (1976), p. 33 et seq.

The compounds of the present invention may be used in the form of pharmaceutically-acceptable salts derived from inorganic or organic acids. By "pharmaceutically-acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically-acceptable salts are well-known in the art. For example, S. M. Berge, et al. [Describe], *describe* pharmaceutically-acceptable salts in detail in [J. Pharmaceutical Sciences], *J. Pharmaceutical Sciences* (*1977*) [1977,] 66; 1 et seq. The salts may be prepared [in situ] *in situ* during the final isolation and purification of the compounds of the invention or separately by reacting a free base function with a suitable acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. [Water] *Water-soluble,* or oil-soluble, or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared [in situ] *in situ* during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically-acceptable basic addition salts include, but are not limited to, cations based on alkali metals or alkaline earth metals such as lithium, sodium, potassium, calcium, magnesium [and], aluminum [salts] and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically-acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.1 to about 50 mg, more preferably of about 5 to about 20 mg of active compound per kilogram of body weight per day are administered orally or intravenously to a mammalian patient. If desired, the effective daily dose may be divided into multiple doses for purposes of administration, e.g. two to four separate doses per day.

Preparation of Compounds of this Invention

The compounds and processes of the present invention may be better understood in connection with the following synthetic schemes which illustrate the methods by which the compounds of the invention can be prepared.

Scheme 1

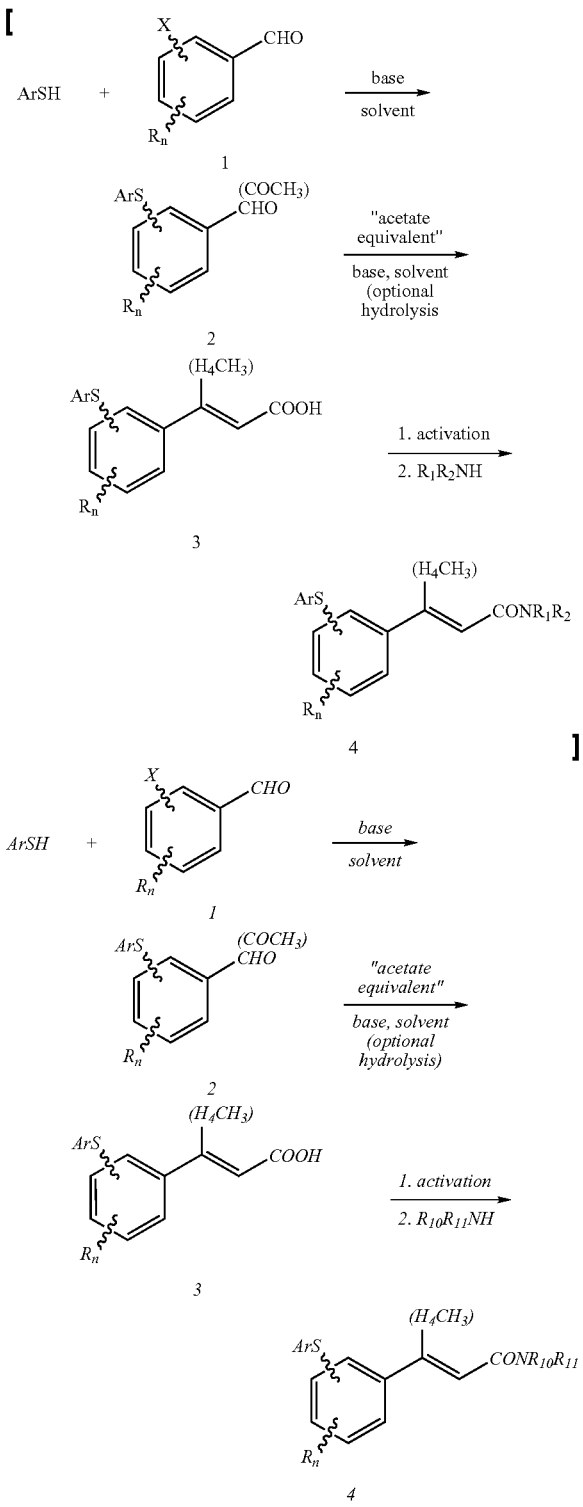

Scheme 1 describes the synthesis of a typical cinnamide-substituted diaryl sulfide 4 through an aldehyde intermediate 2. Aldehyde 2 is prepared by reaction of a thiophenol (for example 2,4-dichlorothiophenol, 2-bromothiophenol, or the like) with halo-substituted benzaldehyde derivative 1 (e.g. 2-chlorobenzaldehyde, 3-chloro,4-fluorobenzaldehyde, or the like) in the presence of base (e.g. sodium carbonate, triethylamine, or the like) and a polar solvent (e.g. dimethylformamide, dimethylsulfoxide, or the like). The aldehyde group is homologated to the corresponding cinnamic acid 3, using an acetate equivalent (for example, malonic acid, triethoxyphosphonoacetate, or the like) in the presence of an appropriate base and solvent. In some cases, it may be necessary to hydrolyze an intermediate ester (for example using sodium hydroxide in alcohol). The acid group is activated (for example using thionyl chloride, or dicyclohexylcarbodiimide and N-hydroxysuccinimide, or the like) and reacted with a primary or secondary amine (for example, 6-aminohexanol, pyrrolidone-3-propylamine, or the like) to provide the desired analog 4. In one variant, a haloacetophenone can replace benzaldehyde 2; the resultant cinnamides 4 are substituted with a methyl group at the 3-position.

Scheme 2

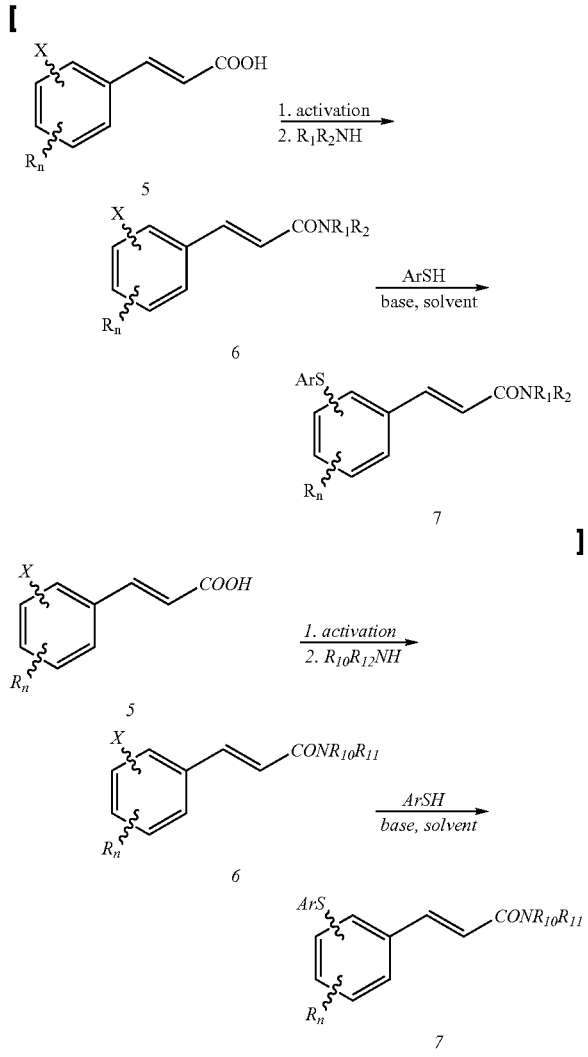

Alternatively, the order of these coupling steps may be reversed (Scheme 2). A substituted halocinnamic acid 5 (e.g. 3-chloro,2-nitrocinnamic acid or the like) may be coupled with a primary or secondary amine (e.g. N-acetylpiperazine or the like) as described above to give the corresponding amide 6. The halo-group can then be displaced with a substituted thiophenol in the presence of base to provide the product 7.

Scheme 3

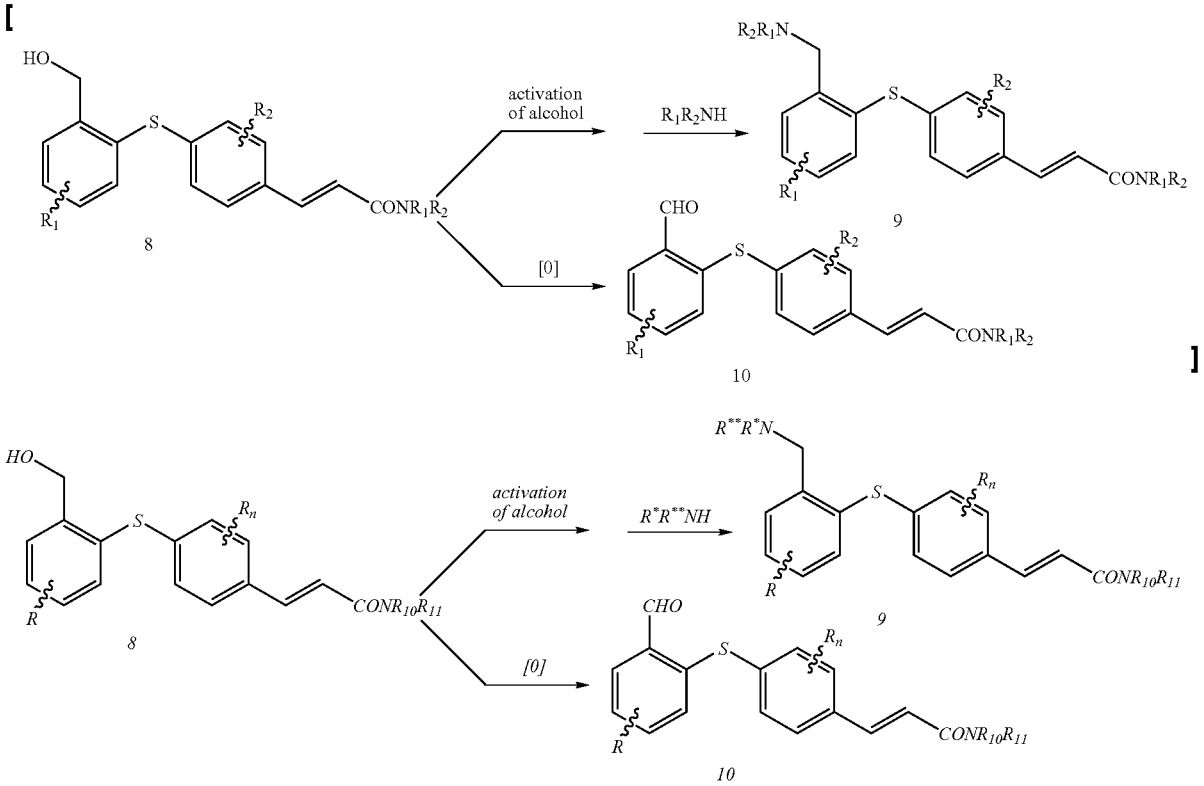

A number of the compounds described herein may be prepared from intermediate benzylic alcohols like 8 (Scheme 3) Activation of the alcohol moiety (for example, using phosphorus tribromide or methanesulfonyl chloride and lithium halide in dimethylformamide) and displacement with a primary or secondary amine (e.g. morpholine, N-formylpiperazine or the like) provides analogs with structures related to 9. Alternatively the alcohol may be oxidized (for example using TPAP or PCC or the like) to give aldehyde 10.

Scheme 4

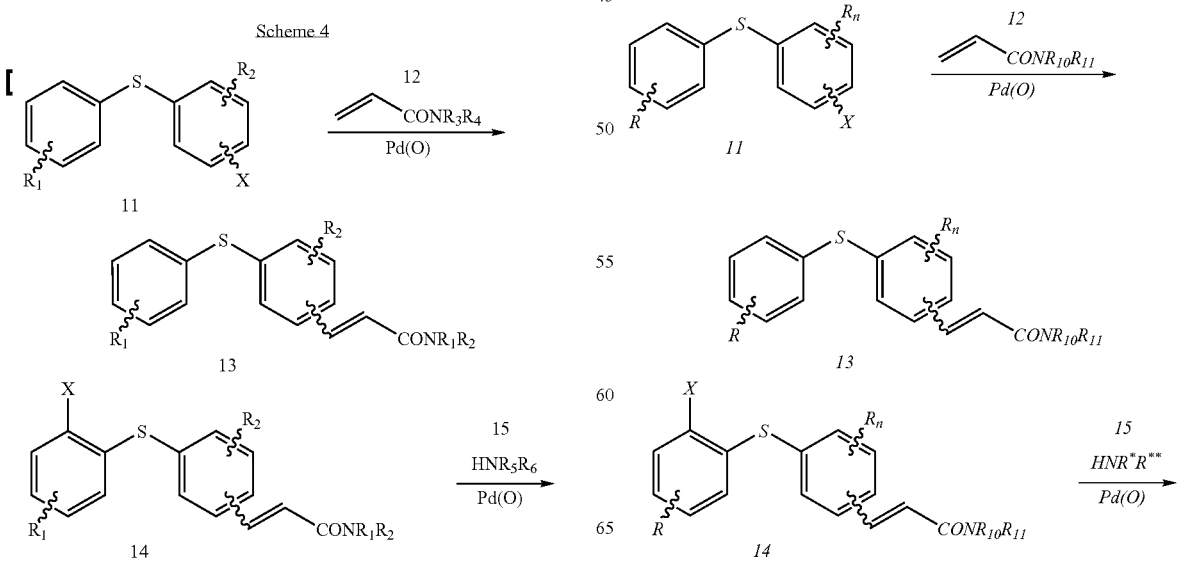

-continued

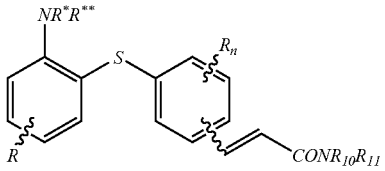

16

Cinnamides like 13 may be prepared from halo-substituted derivatives 11 by palladium-mediated coupling [e.g. using tetrakis (o-tolyl phosphine) palladium (0), $Pd_2(dba)_3$, or the like] with acrylamide derivatives 12 (Scheme 4). In similar manner, anilino-cinnamides like 16 can be prepared by palladium-mediated coupling of amines 15 with halo-cinnamides 14.

Scheme 5

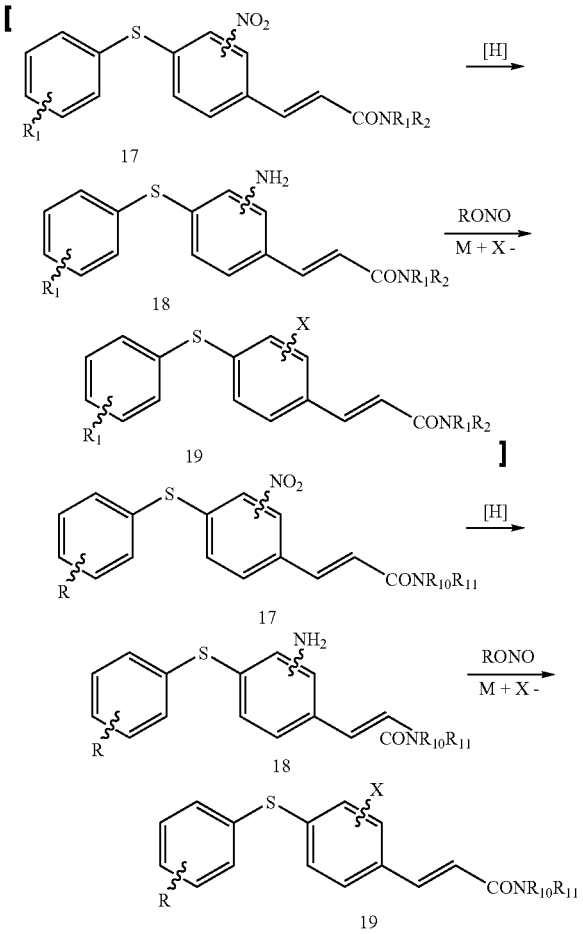

In some cases, functional groups on the aromatic rings can be modified to produce new analogs (Scheme 5). For example, a nitro group in compounds like 17 may be reduced (for example, with tin(II) chloride, or by catalytic hydrogenation, or the like) to the corresponding amine 18. This amine may then itself be converted to a halogen, for example by diazotization using nitrous acid or t-butyl nitrite in the presence of a metal halide salt like cupric bromide, providing analog 19.

Scheme 6

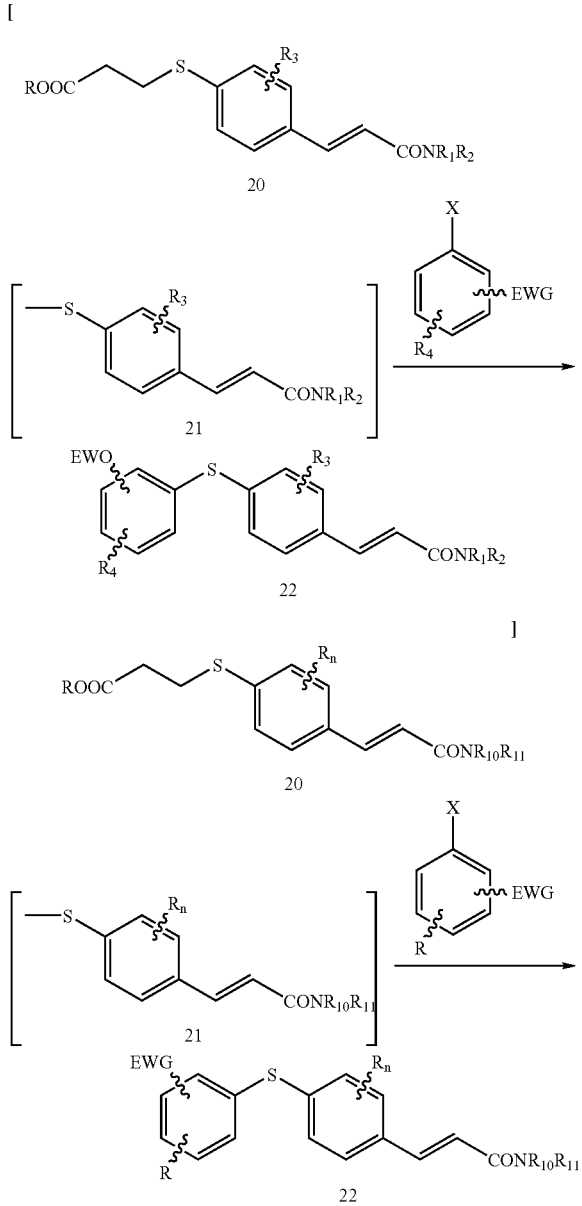

It is also possible to assemble cinnamide-substituted diaryl sulfides in a "reverse" sense (Scheme 6). Thus, for example, compound 20, prepared as described in Scheme 1, may be deprotected by treatment with base (e.g. potassium t-butoxide or the like) to provide thiolate anion 21, which may be reacted with an activated haloarene (e.g. 2,3-dichlorobenzaldehyde, 3-chloro,4-fluorobenzaldehyde or the like) to provide the corresponding product 22.

The compounds and processes of the present invention will be better understood in connection with the following examples which are intended as an illustration of and not a limitation upon the scope of the invention.

EXAMPLE 1

(2,4-Dichlorophenyl)[2-(E-((6-hydroxyhexylamino) carbonyl)ethenyl)phenyl]sulfide

EXAMPLE 1A

2-[(2,4-Dichlorophenyl)thio]benzaldehyde

To a stirred solution of 2,4-dichlorothiophenol (2.0 g, 11.2 mmol) in 25 mL of anhydrous DMF was added potassium carbonate (3.09 g, 22.4 mmol), followed by 2-chlorobenzaldehyde (1.26 mL, 11.3 mmol). The mixture was then heated under nitrogen atmosphere at 70° C. for 5 hours. The reaction mixture was then allowed to cool to room temperature and partitioned between ether and water. The aqueous layer was extracted with ether once and the combined organic layer was washed with water and brine, dried over sodium sulfate and condensed in vacuo. The crude product was purified via silica gel flash chromatography, eluting with 5–10% ether/hexanes, to give 2.62 g (9.25 mmol, 83%) of the desired aldehyde as a colorless oil, which solidified slowly upon standing at room temperature.

EXAMPLE 1B trans-2-[(2,4-Dichlorophenyl)thio]cinnamic acid

A mixture of the aldehyde (1.50 g, 5.3 mmol) from Example 1A, malonic acid (1.21 g, 11.6 mmol), piperidine (78.6 μL, 0.80 mmol) in 8.0 mL of anhydrous pyridine was heated at 110° C. for 2 hours. Gas evolution ceased during this period. Pyridine was then removed under vacuum. Water and 3N aq. HCl were then added with stirring. The desired cinnamic acid was then collected through filtration, washed with cold water and dried in a vacuum oven overnight to give 1.56 g (4.8 mmol, 91%) of white solid.

EXAMPLE 1C (2,4-Dichlorophenyl)[2-(E-((6-hydroxyhexylamino) carbonyl)ethenyl)phenyl]sulfide A suspension of the acid (284 mg, 0.87 mmol) from Example 1B in 5 mL of methylene chloride was stirred with $(COCl)_2$ (84 μL, 0.97 mmol), and one drop of DMF under nitrogen atmosphere for 90 minutes. The solvent was then removed under vacuum. The residue $(COCl)_2$ was removed with benzene (2×) in vacuo. To a separate flask, previously filled with 6-amino-1-hexanol (12 mg, 0.10 mmol), Hunig's base (22.8 μL, 0.13 mmol) and DMAP (1.1 mg, 0.008 mmol) in 2.0 mL of $CH_2Cl_2$, the acid chloride (30 mg, 0.087 mmol) in 1.0 mL of $CH_2Cl_2$ was then dropped in slowly. After 30 minutes, the reaction mixture was poured into 3N HCl and extracted with ethyl aceetate (EtOAc). The organic layer was washed with brine, dried with $Na_2SO_4$, condensed under reduced pressure. The crude product was purified by preparative TLC to give 21.0 mg (90%) of the title compound as a colorless oil. $^1$H NMR ($CDCl_3$, 300 MHz) δ 1.31–1.48 (m, 4H), 1.48–1.70 (m, 4H), 3.37 (q, J=6.7 Hz, 2H), 3.65 (t, J=6.3 Hz, 2H), 5.63 (br s, 1H), 6.36 (d, J=15.9 Hz, 1H), 6.71 (d, J=9.3 Hz, 1H), 7.95 (dd, J=2.4, 8.7 Hz, 1H), 7.31–7.49 (m, 4H), 7.65 (dd, J=2.1, 7.5 Hz, 1H), 7.99 (d, J=15.9 Hz, 1H). MS (DSI/$NH_3$) $(M+NH_4)^+$ at m/z 441, 443, 445.

EXAMPLE 2

(2,4-Dichlorophenyl)[2-(E-((3-(1-imidazolyl) propylamino)carbonyl)ethenyl)phenyl]sulfide The title compound was prepared by the procedures described in Example 1C substituting 6-amino-1-hexanol with 1-(3-aminopropyl)imidazole. White powder; $^1$H NMR ($d^6$-DMSO, 300 MHz) δ 1.88 (p, J=7.7 Hz, 2H), 3.11 (q, J=7.7 Hz, 2H), 3.97 (t, J=7.7 Hz, 2H), 6.63 (d, J=15.9 Hz, 1H), 6.70 (d, J=8.7 Hz, 1H), 6.89 (d, J=0.9 Hz, 1H), 7.17 (d, J=0.9 Hz, 1H), 7.33 (dd, J=2.7, 8.7 Hz, 1H), 7.46–7.65 (m, 4H), 7.72 (d, J=2.7 Hz, 1H), 7.78 (d, J=15.9 Hz, 1H), 7.80 (d, J=8.7 Hz, 1H), 8.24 (t, J=5.9 Hz, 1H). MS (DCI/$NH_3$) $(M+H)^+$ at m/z 448, 450, 452. Analysis calculated for $C_{21}H_{19}N_3O_1Cl_3S_1.0.87H_2O$: C, 56.30; H, 4.67; N, 9.38. Found: C, 56.30; H, 4.56; N, 9.27.

EXAMPLE 3

(2,4-Dichlorophenyl)[2-chloro-4-(E-((2-hydroxyethylamino)carbonyl)ethenyl)phenyl]sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with ethanolamine. Colorless oil; $^1$H NMR ($CDCl_3$, 300 MHz) δ 3.57 (q, J=7.65Hz, 2H), 3.71 (q, J=7.65 Hz, 2H), 6.06 (br s, 1H), 6.40 (d, J=15.3 Hz, 1H), 6.96 (d, J=8.7 Hz, 1H), 7.22–7.30 (m, 4H), 7.49–7.60 (m, 1H), 7.55 (d, J=15.3 Hz, 1H). MS (APCI) $(M+H)^+$ at m/z 402, 404, 406, 408. Analysis calculated for $C_{17}H_{14}N_1O_2Cl_3S_1.0.25H_2O$: C, 50.14; H, 3.59; N, 3.44. Found: C, 50.16; H, 3.62; N, 3.29.

EXAMPLE 4

(2,4-Dichlorophenyl)[2-chloro-4-(E-((6-hydroxyhexylamino)carbonyl)ethenyl)phenyl]sulfide The title compound was prepared by the procedures described in Example 1 substituting 2-chlorobenzaldehyde with [3-chloro-4-fluoro-benzadehyde] *3-chloro-4-fluoro-benzaldehyde*. Colorless oil; $^1$H NMR ($CDCl_3$, 300 MHz) δ 1.42 (m, 4H), 1.58 (m, 4H), 3.40 (q, J=6.7 Hz, 2H), 3.65 (br m, 2H), 5.60 (br t, 1H), 6.35 (d, J=15.3 Hz, 1H), 6.98 (d, J=8.7 Hz, 1H), 7.22–7.30 (m, 4H), 7.49–7.60 (m, 1H), 7.55 (d, J=15.3 Hz, 1H). MS (APCI) $(M+H)^+$ at m/z 458, 460, 462, 464. Analysis calculated for $C_{21}H_{22}N_1O_2Cl_3S_1.0.27H_2O$: C, 54.39; H, 4.90; N, 3.02. Found: C, 54.40; H, 4.85; N, 2.71.

EXAMPLE 5

(2,4-Dichlorophenyl)[2-chloro-4-(E-((bis-(2-hydroxyethyl)amino)carbonyl)ethenyl)phenyl]sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with diethanolamine. Colorless oil; $^1$H NMR ($CDCl_3$, 300 MHz) δ 2.99 (br s, 2H), 3.67 (br m, 4H), 3.88 (t, J=5.1 Hz, 2H), 3.94 (t, J=5.1 Hz, 2H), 6.94 (d, J=1.53 Hz, 1H), 6.97 (d, J=8.7 Hz, 1H), 7.21–7.32 (m, 3H), 7.50–7.54 (m, 1H), 7.58 (d, J=2.4 Hz, 1H), 7.58 (d, J=15.3 Hz, 1H). MS (APCI) $(M+H)^+$ at m/z 446, 448, 450, 452. Analysis calculated for $C_{19}H_{18}N_1O_3Cl_3S_1.1.09H_2O$: C, 48.93; H, 4.36; N, 3.00. Found: C, 48.88; H, 4.00; N, 3.01.

EXAMPLE 6

[(2,4-Dichlorophenyl)[2-chloro-4-(E-((3-(1-pyrrolidin-2-only)propylamino)carbonyl)ethenyl) phenyl]sulfide] *(2,4-Dichlorophenyl)[2-chloro-4-(E-((3-(2-oxopyrrolidin-1-yl)propylamino)carbonyl) ethenyl)phenyl]sulfide*

The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with 1-(3-aminopropyl)-2-pyrrolidinone. Colorless oil; $^1$H NMR ($CDCl_3$, 300 MHz) δ 1.74 (qu, J=6.0 Hz, 2H), 2.09 (qu, J=7.5 Hz, 2H), 2.45 (t, J=8.25 Hz, 2H), 3.33 (q, J=6.0 Hz, 2H), 3.42 (q, J=8.25 Hz, 4H), 6.46 (d, J=15.6 Hz, 1H), 7.02 (d, J=8.7 Hz, 1H), 7.14–7.23 (m, 2H), 7.30 (dd, J=2.4, 8.7 Hz, 1H), 7.51 (d, J=2.4 Hz, 1H). 7.51 (d, J=15.6 Hz, 1H), 7.60 (d, J=2.1 Hz, 1H). MS (DCI/$NH_3$) $(M+H)^+$ at m/z 483, 485, 487, 489. Analysis calculated for $C_{22}H_{21}N_2O_2Cl_3S_1.0.57H_2O$: C, 53.48; H, 4.52; N, 5.67. Found: C, 53.49; H, 4.60; N, 5.65.

EXAMPLE 7

(2,4-Dichlorophenyl)[2-chloro-4-(E-((1-morpholinyl)carbonyl)ethenyl)phenyl]sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with morpholine. White solid; $^1H$ NMR ($CDCl_3$, 300 MHz) δ 3.59–3.80 (m, 8H), 6.83 (d, J=15.6 Hz, 1H), 6.97 (d, J=8.7 Hz, 1H), 7.16–7.32 (m, 3H), 7.49–753 (m, 1H), 7.59 (d, J=2.4 Hz, 1H), 7.59 (d, J=15.6 Hz, 1H). MS (DCI/$NH_3$) $(M+H)^+$ at m/z 428, 430, 432, 434. Analysis calculated for $C_{19}H_{16}N_1O_2Cl_3S_1.0.46H_2O$: C, 52.22; H, 3.90; N, 3.20. Found: C, 52.20; H, 3.76; N, 3.12.

EXAMPLE 8

(2,4-Dichlorophenyl)[2-chloro-4-(E-((4-methylpiperazin-1-yl)carbonyl)ethenyl)phenyl] sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with 1-methylpiperazine. Colorless oil; $^1H$ NMR ($CDCl_3$, 300 MHz) δ 2.37 (s, 3H), 2.51 (br m, 4H), 3.64–3.87 (br m, 4H), 6.85 (d, J=15.6 Hz, 1H), 6.98 (d, J=8.7 Hz, 1H), 7.19–7.25 (m, 2H), 7.27 (dd, J=2.1, 8.7 Hz, 1H), 7.52 (t, J=0.9 Hz, 1H), 7.57 (d, J=15.6 Hz, 1H), 7.60 (d, J=2.1 Hz, 1H). MS (DCI/$NH_3$) $(M+H)^+$ at m/z 441, 443, 445, 447. Analysis calculated for $C_{20}H_{19}N_2O_1Cl_3S_1.0.45H_2O$: C, 53.39; H, 4.46; N, 6.23. Found: C, 53.37; H, 4.46; N, 6.07.

EXAMPLE 9

(2,4-Dichlorophenyl)[2-chloro-4-(E-((4-acetylpiperazin-1-yl)carbonyl)ethenyl)phenyl]sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with 1-acetylpiperazine. White solid; $^1H$ NMR ($CDCl_3$, 300 MHz) δ 2.15 (s, 3H), 3.50–3.58 (m, 2H), 3.58–3.85 (m, 6H), 6.85 (d, J=15.3 Hz, 1H), 6.96 (d, J=8.7 Hz, 1H), 7.24–7.36 (m, 3H), 7.54 (dd, J=2.4 Hz, 1H), 7.61 (d, J=15.3 Hz, 1H), 7.61 (d, J=2.1 Hz, 1H). MS (DCI/$NH_3$) $(M+H)^+$ at m/z 486, 488, 490, 492. Analysis calculated for $C_{21}H_{19}N_2O_2Cl_3S_1.0.85H_2O$: C, 51.99; H, 4.30; N, 5.77. Found: C, 52.03; H, 4.27; N, 5.67.

EXAMPLE 10

(2,4-Dichlorophenyl)[2-chloro-4-(E-((4-(2-pyridyl) piperazin-1-yl)carbonyl)ethenyl)phenyl]sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with 1-(2-pyridyl) piperazine. White solid; $^1H$ NMR ($CDCl_3$, 300 MHz) δ 3.59 (br m, 2H), 3.69 (br m, 2H), 3.78 (br m, 2H), 3.86 (br m, 2H), 6.64–6.72 (m, 2H), 6.90 (d, J=15.6 Hz, 1H), 6.99 (d, J=8.7 Hz, 1H), 7.22–7.25 (m, 2H), 7.31 (dd, J=2.4, 8.7 Hz, 1H), 7.49–7.57 (m, 2H), 7.61 (d, J=15.6 Hz, 1H), 7.62 (d, J=2.4 Hz, 1H), 8.19–8.24 (m, 1H). MS (DCI/$NH_3$) $(M+H)^+$ at m/z 504, 506, 508, 510. Analysis calculated for $C_{24}H_{20}N_3O_1Cl_3S_1$: C, 57.10; H, 3.99; N, 8.32. Found: C, 57.12; H, 4.06; N, 8.29.

EXAMPLE 11

(2-(Hydroxymethyl)phenyl)[2-chloro-4-(E-((1-morpholinyl)carbonyl)ethenyl)phenyl]sulfide The title compound was prepared by the procedures described in Example 1 substituting 2,4-dichlorothiophenol with 2-mercaptobenzyl alcohol, 2-chlorobenzaldehyde with [3-chloro-4-fluoro-benzadehyde] *3-chloro-4-fluoro-benzaldehyde*, and 6-amino-1-hexanol with morpholine. White solid; $^1H$ NMR ($CDCl_3$, 300 MHz) δ 3.50–3.62 (br m, 6H), 3.65–3.74 (br m, 2H), 4.54 (d, J=5.7 Hz, 2H), 5.33 (t, J=5.7 Hz, 1H), 6.62 (d, J=8.7 Hz, 1H), 7.28 (d, J=15.0 Hz, 1H), 7.36 (d, J=7.8 Hz, 1H), 7.42 (d, J=15.0 Hz, 1H), 7.43 (dd, J=1.8, 8.7 Hz, 1H), 7.50 (dd, J=2.1, 8.7 Hz, 1H), 7.55 (dd, J=2.1, 7.8 Hz, 1H), 7.68 (dd, J=1.5, 8.1 Hz, 1H), 8.02 (d, J=2.1 Hz, 1H). MS (DCI/$NH_3$) $(M+H)^+$ at m/z 390, 392. Analysis calculated for $C_{20}H_{20}N_1O_3Cl_1S_1.0.09H_2O$: C, 61.35; H, 5.20; N, 3.58. Found: C, 61.37; H, 5.48; N, 3.81.

EXAMPLE 12

(2-(Bromophenyl)[2-chloro-4-(E-((1-morpholinyl) carbonyl)ethenyl)phenyl]sulfide

The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-4-fluoro-benzaldehyde*, and 6-amino-1-hexanol with morpholine. White solid; $^1H$ NMR ($d^6$-DMSO, 300 MHz) δ 3.50–3.66 (br m, 6H), 3.66–3.79 (br m, 2H), 7.05 (d, J=8.7 Hz, 1H), 7.26 (dd, J=2.1, 8.1 Hz, 1H), 7.33 (dd, J=2.1, 8.1 Hz, 1H), 7.36 (d, J=15.6 Hz, 1H), 7.39 (dd, J=1.8, 12.0 Hz, 1H), 7.45 (dd, J=1.8, 6.3 Hz, 1H), 7.48 (d, J=15.6 Hz, 1H), 7.64 (dd, J=2.1, 8.7 Hz, 1H), 7.80 (dd, J=2.8, 8.7 Hz, 1H), 8.09 (d, J=2.1 Hz, 1H). MS (DCI/$NH_3$) $(M+H)^+$ at m/z 438, 440, 442.

EXAMPLE 13

(2,4-Dichlorophenyl)[2-chloro-4-(E-((2-hydroxyethyl)piperazin-1-yl)carbonyl)ethenyl) phenyl]sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with 1-hydroxyethylpiperazine. Colorless oil; $^1H$ NMR ($CDCl_3$, 300 MHz) δ 2.85–3.20 (br m, 6H), 3.84–4.29 (m, 6H), 6.80 (d, J=15.3 Hz, 1H), 6.94 (d, J=8.7 Hz, 1H), 7.72–7.38 (m, 3H), 7.50–7.56 (m, 1H), 7.56–7.62 (m, 1H), 7.60 (d, J=15.3 Hz, 1H). MS (DCI/$NH_3$) $(M+H)^+$ at m/z 471, 473, 475, 477.

EXAMPLE 14

(2,4-Dichlorophenyl)[2-chloro-4-(E-((2-hydroxyethoxyethyl)piperazin-1-yl)carbonyl) ethenyl)phenyl]sulfide The title compound was prepared by the procedures described in Example 1 substituting 2-chlorobenzaldehyde with 1 [3-chloro-4-fluoro-benzadehyde] *3-chloro-4-fluoro-benzaldehyde*, and 6-amino-1-hexanol with 1-[2-(2-hydroxyethoxy)ethyl]piperazine. Colorless oil; $^1$H NMR ($CDCl_3$, 300 MHz) δ 2.73 (br m, 6H), 3.58–3.68 (m, 2H), 3.68–4.00 (m, 8H), 6.84 (d, J=15.3 Hz, 1H), 6.97 (d, J=8.7 Hz, 1H), 7.20–7.34 (m, 3H), 7.54 (d, J=7.5 Hz, 1H), 7.58 (d, J=15.3 Hz, 1H), 7.58–7.65 (overlapping d, 1H). MS ($DCIINH_3$) $(M+H)^+$ at m/z 515, 517, 519, 521.

EXAMPLE 15

(2-(Bromophenl)[2-chloro-4-(E-((3-hydroxymethyl) piperidin-1-yl)carbonyl)ethenyl)phenyl]sulfide The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-4-fluoro-benzaldehyde*, and 6-amino-1-hexanol with 3-hydroxymethylpiperidine. $^1$H NMR (DMSO-$d_6$, 300 MHz) δ 8.07 (d, J=17.7 Hz, 1H), 7.80 (d, J=7.7 Hz, 1H), 7.63 (br d, J=7.7 Hz, 1H), 7.44 (d, J=7.0 Hz, 1H), 7.40 (br s, 2H), 7.35 (m, 1H), 7.25 (dd 7.7, 1.5, 1H), 7.06 (dd, J=8.1 2.9, 1H), 4.57 (m, 1H), 4.45 (m, 1H), 4.16 (br m, 2H), 1.2–1.8 (m, 8H). HRMS calculated for $C_{21}H_{21}N_1O_2S_1Br_1Cl_1$: 466.0243. Observed: 466.0247.

EXAMPLE 16

(2-(Bromophenyl)[2-chloro-4-(E-((2-hydroxymethyl)piperidin-1-yl)carbonyl)ethenyl) phenyl]sulfide The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-4-fluoro-benzaldehyde*, and 6-amino-1-hexanol with 2-hydroxymethylpiperidine. $^1$H NMR (DMSO-$d_6$, 300 MHz) δ 8.03 (m, 1H), 7.79 (d, J=7.8 Hz, 1H), 7.61 (m, 1H), 7.30–7.45 (m, 4H), 7.23 (m, 1H), 7.07 (m, 1H), 4.79 (m, 2H), 4.61 (m, 2H), 4.10 (m, 1H), 1.50 (m, 6H). HRMS calculated for $C_{21}H_{21}N_1O_2S_1Br_1Cl_1$: 466.0243. Observed: 466.0247.

EXAMPLE 17

(2-(Bromophenl)[2-chloro-4-(E-((3-acetamidopyrrolidin-1-yl)carbonyl)ethenyl)phenyl] sulfide The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-4-fluoro-benzaldehyde*, and 6-amino-1-hexanol with 3-acetamidopyrrolidine. $^1$H NMR (DMSO-$d_6$, 300 MHz) δ 8.14 (m, 1H), 8.07 (dd, J=9.8, 1.7 Hz, 1H), 7.80 (d, J=7.8 Hz, 1H), 7.64 (dd, J=8.1, 1.7 Hz, 1H), 7.25–7.47 (m, 4H), 7.10 (t, J=7.8 Hz, 1H), 7.03 (dd, J=8.1, 1.7 Hz, 1H), 3.45–4.34 (m, 6H), 2.02 (m, 2H), 1.81 (ap d, J=1.4 Hz, 1H), HRMS calculated for $C_{21}H_{20}N_2O_2S_1Br_1Cl_1$: 479.0196. Observed: 479.0183.

EXAMPLE 18

(2-(Bromophenyl)[2-chloro-4-(E-((4-hydroxypiperidin-1-yl)carbonyl)ethenyl)phenyl] sulfide The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-4-fluoro-benzaldehyde*, and 6-amino-1-hexanol with 4-hydroxypiperidine. $^1$H NMR (DMSO-$d_6$, 300 MHz) δ 8.08 (d, J=1.7 Hz, 1H), 7.80 (dd, J=8.0, 1.5 Hz, 1H), 7.63 (dd, J=8.3, 1.9 Hz, 1H), 7.44 (ap dd, J=7.5, 1.4 Hz, 2H), 7.40 (ap d, J=3.7 Hz 2H), 7.34 (dt, J=7.6, 1.8 Hz, 1H), 7.25 (dd, J=7.5, 1.7 Hz 1H), 7.05 (d, J=8.1 Hz, 1H), 4.76 (br s, 1H), 4.01 (m, 2H), 3.72 (m, 1H), 3.12 (m, 1H), 1.75 (m, 2H), 1.32 (m, 2H). HRMS calculated for $C_{20}H_{19}N_1O_2S_1Br_1Cl_1$: 452.0087. Observed: 452.0076.

EXAMPLE 19

(2-(Bromophenyl)[2-chloro-4-(E-((piperidin-1-yl) carbonyl)ethenyl)phenyl]sulfide The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-4-fluoro-benzaldehyde*, and 6-amino-1-hexanol with piperidine. $^1$H NMR (DMSO-$d_6$, 300 MHz) δ 8.08 (d, J=1.7 Hz, 1H), 7.80 (dd, J=8.1, 1.4 Hz, 1H), 7.63 (dd, J=8.1, 1.7 Hz, 1H), 7.44 (ap dd, J=7.6, 1.5 Hz, 1H), 7.39 (ap d, J=4.8 Hz, 2H), 7.34 (dt, J=7.5, 1.6, 1H), 7.24 (dd, J=7.5, 1.7, 1H), 7.05 (d, J=8.1 Hz, 1H), 3.65 (br m, 2H), 3.53 (br m, 2H), 1.62 (br m, 2H), 1.50 (br m, 4H). HRMS calculated for $C_{20}H_{19}N_1O_1S_1Br_1Cl_1$: 436.0130. Observed: 436.0122.

EXAMPLE 20

(2,4-Dichlorophenyl)[2-chloro-4-(E-((3-carboxypiperidin-1-yl)carbonyl)ethenyl)phenyl] sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with nipecotic acid. Colorless oil; $^1$H NMR ($CDCl_3$, 300 MHz) δ 1.44–1.68 (br m, 1H), 1.68–2.00 (br m, 2H), 2.51–2.67 (br m, 1H), 3.13–3.37 (br m, 1H), 3.80–4.12 (br m, 1H), 4.30–5.00 (br m, 3H), 6.86 (d, J=15.3 Hz, 1H), 6.99 (d, J=8.7 Hz, 1H), 7.16–7.24 (m, 2H), 7.29 (d, J=8.7 Hz, 1H), 7.47–7.55 (m, 1H), 7.55 (d, J=15.3 Hz, 1H), 7.60 (br d, 1H). MS (APCI) $(M+H)^+$ at m/z 470, 472, 474, 476.

EXAMPLE 21

(2,4-Dichlorophenyl)[2-chloro-4-(E-((4-carboxypiperidin-1-yl)carbonyl)ethenyl)phenyl] sulfide The title compound was prepared by the procedures described in Example 1 substituting 2-chlorobenzaldehyde with [3-chloro-4-fluoro-benzadehyde] *3-chloro-4-fluoro-benzaldehyde*, and 6-amino-1-hexanol with isonipecotic acid. Colorless oil; $^1$H NMR ($CDCl_3$, 300 MHz) δ 1.68–1.85 (m, 2H), 1.98–2.09 (m, 2H), 2.60–2.72 (m, 1H), 2.90–3.13 (br m, 1H), 3.17–3.38 (br, m, 1H), 3.93–4.12 (br m, 1H), 4.38–4.59 (br m, 1H), 6.86 (d, J=15.3 Hz, 1H), 6.99 (dd, J=8.7 Hz, 1H), 7.20–7.25 (m, 2H), 7.28 (dd, J=1.8,8.7 Hz, 1H), 7.49–7.53 (m, 1H), 7.56 (d, J=15.3 Hz, 1H), 7.60 (d, J=1.8 Hz, 1H). MS (APCI) $(M+H)^+$ at m/z 470, 472, 474, 476.

EXAMPLE 22

(2-Bromophenyl)[2-chloro-4-(E-((4-acetylhomopiperazin-1-yl)carbonyl)ethenyl)phenyl] sulfide The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-3-fluoro-benzaldehyde*, and 6-amino-1-hexanol with 4-acetylhomopiperazine. $^1$H NMR (DMSO-$d_6$, 300 MHz) δ 8.10 (m, 1H), 7.81 (d, J=7.7 Hz, 1H), 7.64 (m, 1H), 7.24–7.51 (m, 5H), 7.05 (m, 1H), 3.39–3.77 (m, 8H), 1.97 (m, 3H), 1.68 (m, 2H). HRMS calculated for $C_{22}H_{22}N_2O_2S_1Br_1Cl_1$: 493.0352. Observed: 493.0352.

EXAMPLE 23

(2-Bromophenyl)[2-chloro-4-(E-((thiomorpholin-1-yl)carbonyl)ethenyl)phenyl]sulfide The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-3-fluoro-benzaldehyde*, and 6-amino-1-hexanol with thiomorpholine. $^1$H NMR (DMSO-$d_6$, 300 MHz) 68.10 (d, J=1.5 Hz, 1H), 7.80 (d, J=8.5 Hz, 1H), 7.64 (dd, J=8.1, 1.5 Hz, 1H), 7.31–7.48 (m, 4H), 7.36 (m, 1H), 7.26 (dd, J=8.1, 1.8 Hz, 1H), 7.05 (d J=8.1 Hz, 1H), 3.96 (m, 2H), 3.82 (m, 2H), 2.62 (m, 4H). HRMS calculated for $C_{19}H_{17}N_1O_1S_2Br_1Cl_1$: 455.9681. Observed: 455.9676.

EXAMPLE 24

[(2-Bromophenyl)[2-chloro-4-(E-((4-(1-benzimidazol-2-only)piperidin-1-yl)carbonyl) ethenyl)phenyl]sulfide] *(2-Bromophenyl)[2-chloro-4-(E-((4-([2-oxo-2,3-dihydro-1H-benzimidazol-1-yl) piperidin-1-yl)carbonyl)ethenyl)phenyl]sulfide*

The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-3-fluoro-benzaldehyde*, and 6-amino-1-hexanol with [4-(1-benzimidazol-2-only)piperidine] *4-(2-oxo-2,3-dihydro-1H-benzimidazol-1-yl)piperidine*. $^1$H NMR (DMSO-$d_6$, 300 MHz) δ 8.14 (d, J=1.5 Hz, 1H), 7.80 (dd, J=7.9, 1.3 Hz, 1H), 7.67 (dd, J=8.1, 1.8 Hz, 1H), 7.48 (ap s, 2H), 7.44 (dt, J=7.5, 1.2, 1H), 7.34 (dt, J=7.6, 1.6, 1H), 7.26 (dd, J=7.7, 1.8 Hz, 1H), 7.22 (m, 1H), 7.06 (d, J=8.1, 1H), 6.97 (ap d, J=2.6, 3H), 4.64 (m, 1H), 4.48 (m, 2H), 2.79 (m, 2H), 2.29 (m, 2H), 1.78 (m, 2H). HRMS calculated for $C_{27}H_{23}N_3O_2SBr_1Cl_1$: 568.0461. Observed: 568.0477.

EXAMPLE 25

[(2-Bromophenyl)[2-chloro-4-(E-((2-tetrahydroisoguinolinyl)carbonyl ethenyl)phenyl] sulfide] *(2-Bromophenyl)[2-chloro-4-(E-((2-tetrahydroisoquinolinyl)carbonyl)ethenyl)phenyl] sulfide*

The title compound was prepared by the procedures described in Example 1 substituting 2,4-dichlorothiophenol with 2-bromothiophenol, 2-chlorobenzaldehyde with [3-chloro-4-fluoro-benzadehyde] *3-chloro-3-fluoro-benzaldehyde*, and 6-amino-1-hexanol with tetrahydroisoquinoline. $^1$H NMR (DMSO-$d_6$, 300 MHz) δ 8.12 (d, J=7.4 Hz, 1H), 7.81 (dd, J=7.7. 1.1 Hz, 1H), 7.67 (dd, J=8.3, 1.3 Hz, 1H), 7.47 (m, 2H), 7.43 (dd, J=7.5, 1.3 Hz, 2H), 7.34 (dt, J=7.6, 1.7 Hz, 1H), 7.27 (d 7.7 Hz, 1H), 7.19 (m, 4H), 7.05 (d, J=8.1 Hz, 1H), 4.92 (s, 1H), 4.72 (s, 1H), 3.95 (t, J=5.9 Hz, 1H), 3.78 (t, J=5.7 Hz, 1H), 2.89 (t, J=5.3 HZ, 1H), 2.83 (t, J=3.7, 1H). HRMS calculated for $C_{24}H_{19}N_1O_2S_1Br_1Cl_1$: 484.0138. Observed: 484.0128.

EXAMPLE 26

(2-Methylphenyl)[2-trifluoromethyl-4-(E-((4-acetylpiperazin-1-yl)carbonyl ethenyl)phenyl]sulfide The title compound was prepared by the procedures described in Example 1 substituting 2,4-dichlorothiophenol with 2-methylthiophenol, 2-chlorobenzaldehyde with [4-fluoro-3-trifluoromethylbenzadehyde] *4-fluoro-3-trifluoromethylbenzaldehyde*, and 6-amino-1-hexanol with 1-acetylpiperazine. $^1$H NMR ($CDCl_3$, 300 MHz) δ 7.79 (s, 1H); 7.63 (d, J=15.4 Hz, 1H); 7.51 (d, J=6.8 Hz, 1H); 7.41–7.33 (m, 3H); 7.28 (m, 1H); 6.83 (d, J=15.4 Hz, 1H); 6.79 (d, J=6.8 Hz, 1H); 3.80–3.60 (m, 6H); 3.57–3.50 (m, 2H); 2.34 (s, 3H); 2.14 (s, 3H). MS (ESI) m/z 919 $(2M+Na)^+$, 897 $(2M+H)^+$, 471 $(M+Na)^+$, 449 $(M+H)^+$.

EXAMPLE 27

(2-Methylphenyl)[2-trifluoromethyl-4-(E-((1-morpholinyl)carbonyl)ethenyl)phenyl]sulfide The title compound was prepared by the procedures described in Example 1 substituting 2,4-dichlorothiophenol with 2-methylthiophenol, 2-chlorobenzaldehyde with [4-fluoro-3-trifluoromethylbenzadehyde] *4-fluoro-3-trifluoromethylbenzaldehyde*, and 6-amino-1-hexanol with morpholine. $^1$H NMR (DMSO-$d_6$, 300 MHz) δ 7.79 (s, 1H); 7.63 (d, J=14.0 Hz, 1H); 7.52 (d, J=7.6 Hz, 1H); 7.40–7.30 (m, 3H); 7.28 (m, 1H); 6.87 (d, J=14.0 Hz, 1H); 6.84 (d, J=7.6 Hz, 1H); 3.73 (br s, 8H); 2.34 (s, 3H). MS (ESI) m/z 837 $(2M+Na)^+$, 815 $(2M+H)^+$, 408 $(M+H)^+$.

EXAMPLE 28

(2-Methylphenyl)[2-trifluoromethyl-4-(E-((2-(1-morpholinyl)ethylamino)carbonyl)ethenyl)phenyl] sulfide The title compound was prepared by the procedures described in Example 1 substituting 2,4-dichlorothiophenol with 2-methylthiophenol, 2-chlorobenzaldehyde with [4-fluoro-3-trifluoromethylbenzadehyde] *4-fluoro-3-trifluoromethylbenzaldehyde*, and 6-amino-1-hexanol with 2-(1-morpholinyl)ethylamine. $^1$H NMR ($CDCl_3$, 300 MHz) δ 7.80 (s, 1H); 7.56 (d, J=15.8 Hz, 1H); 7.50 (d, J=8.1 Hz, 1H); 7.40–7.32 (m, 3H); 7.28 (m, 1H); 6.79 (d, J=15.8 Hz, 1H); 6.40 (d, J=8.1 Hz, 1H); 3.75 (t, J=4.6 Hz, 4H); 3.51 (q, J=5.5 Hz, 2H), 2.57 (t, J=5.8 Hz, 2H); 2.55–2.48 (m, 4H); 2.34 (s, 3H ). MS (ESI) m/z 923 $(2M+Na)^+$, 473 $(M+Na)^+$, 451 $(M+H)^+$.

EXAMPLE 29

(2-Methylphenyl)[2-trifluoromethyl-4-(E-((4-phenylpiperazin-1-yl)carbonyl)ethenyl)phenyl] sulfide The title compound was prepared by the procedures described in Example 1 substituting 2,4-dichlorothiophenol with 2-methylthiophenol, 2-chlorobenzaldehyde with [4-fluoro-3-trifluoromethylbenzadehyde] *4-fluoro-3-trifluoromethylbenzaldehyde*, and 6-amino-1-hexanol with 4-phenylpiperazine. $^1$H NMR ($CDCl_3$, 300 MHz) δ 7.81 (s, 1H); 7.64 (d, J=16.0 Hz, 1H); 7.51 (d, J=8.2 Hz, 1H); 7.40–7.27 (m, 6H); 6.98–6.90 (m, 4H); 6.80 (d, J=8.2 Hz, 1H); 3.88 (br s, 4H); 2.23 (br s, 4H); 2.34 (s, 3H). MS (ESI) m/z 987 $(2M+Na)^+$, 965 $(2M+H)^+$, 505 $(M+Na)^+$, 483 $(M+H)^+$, 451.

EXAMPLE 30

[(2-Methylphenyl)[2-trifluoromethyl-4-(E-((3-(1-pyrrolidin-2-only)propylamino)carbonyl)ethenyl) phenyl]sulfide] *(2-Methylphenyl)[2-trifluoromethyl-4-(E-((3-(2-oxopyrrolidin-1-yl)propylamino) carbonyl)ethenyl)phenyl]sulfide*

The title compound was prepared by the procedures described in Example 1 substituting 2,4-dichlorothiophenol with 2-methylthiophenol, 2-chlorobenzaldehyde with [4-fluoro-3-trifluoromethylbenzadehyde] *4-fluoro-3-trifluoromethylbenzaldehyde*, and 6-amino-1-hexanol with [1-pyrrolidin-2-only)propylamine] *3-(2-oxopyrrolidin-1-yl) propylamine*. $^1$H NMR ($CDCl_3$, 300 MHz) δ 7.78 (s, 1H); 7.53 (d, J=15.6 Hz, 1H); 7.49 (d, J=7.2 Hz, 1H); 7.40–7.33 (m, 3H); 7.14 (m, 1H); 6.80 (d, J=8.2 Hz, 1H); 6.43 (d, J=15.6 Hz, 1H); 3.41 (m, 4H); 3.32 (q, J=6.1 Hz, 2H); 2.43 (t, J=6.6 Hz, 2H); 2.34 (s, 3H), 2.08 (m, 2H), 1.75 (m, 2H). MS (ESI) m/z 947 $(2M+Na)^+$, 925 $(2M+H)^+$, 4.85 $(M+Na)^+$, 463 $(M+H)^+$.

EXAMPLE 31

(2-Methylphenyl)[2-trifluoromethyl-4-(E-((cyclopropylamino)carbonyl)ethenyl)phenyl]sulfide The title compound was prepared by the procedures described in Example 1 substituting 2,4-dichlorothiophenol with 2-methylthiophenol, 2-chlorobenzaldehyde with [4-fluoro-3-trifluoromethylbenzadehyde] *4-fluoro-3-trifluoromethylbenzaldehyde*, and 6-amino-1-hexanol with cyclopropylamine. $^1$H NMR ($CDCl_3$, 300 MHz) δ 7.76 (s, 1H); 7.56 (d, J=15.4 Hz, 1H); 7.50 (d, J=8.4 Hz, 1H); 7.40–7.30 (m, 3H); 7.28 (m, 1H); 6.88 (d, J=8.4 Hz, 1H); 6.30 (d, J=15.4 Hz, 1H); 5.70 (br s, 1H), 2.95 (m, 1H); 2.34 (s, 3H); 0.85 (m, 2H); 0.57 (m, 2H). MS (ESI) m/z 777 $(2M+Na)^+$, 755 $(2M+H)^+$, 400 $(M+Na)^+$, 378 $(M+H)^+$.

EXAMPLE 32

(2,4-Dichlorophenyl)[2-nitro-4-(E-((4-acetylpiperazin-1-yl)carbonyl)ethenyl)phenyl]sulfide

EXAMPLE 32A

1-Chloro-2-nitro-4-(E-((4-acetylpiperazin-1-yl) carbonyl)ethenyl)benzene

To a stirred solution of trans-4-chloro-3-nitrocinnamic acid (1.50 g, 6.59 mmol) and 1-acetylpiperazine (0.89 g, 6.94 mmol) in 20 mL of DMF at room temperature was added EDAC (1.4 g, 7.30 mmol). The mixture was then stirred at room temperature for 2 hours. TLC indicated the complete consumption of the acid. Water was then added to quench the reaction and to precipitate out the product. Cinnamide was then collected through filtration and washed with cold water. The light yellow product was dried in *a* vacuum oven overnight at 40° C[.] to give 2.04 g (6.03 mmol, 91.6%) of the title compound.

EXAMPLE 32B (2,4-Dichlorophenyl)[2-nitro-4-(E-((4-acetylpiperazin-1-yl)carbonyl)ethenyl)phenyl]sulfide To a stirred solution of 4-chloro-3-nitro-cinnamide (275 mg, 0.814 mmol) from Example 32A in 1.0 mL of DMF was added potassium carbonate (169 mg, 1.22 mmol), followed by the dropwise addition of 2,4-dichlorothiophenol (146 mg, 0.815 mmol). The mixture was then stirred at room temperature for 60 minutes. Completion of the reaction was indicated by the TLC. Water was then added to precipitate the product. Filtration, washing with cold water, and drying in a vacuum oven afforded 350 mg (0.728 mmol, 89%) of the [titled] *title* compound as *a* light yellow solid. $^1$H NMR ($d^6$-DMSO, 300 MHz) δ 2.05 (s, 3H), 3.42–3.50 (br m, 4H), 3.50–3.64 (br m, 2H), 3.64–3.79 (br m, 2H), 6.83 (d, J=8.7 Hz, 1H), 7.44 (d, J=15.3 Hz, 1H), 7.55 (d, J=15.3 Hz, 1H), 7.63 (dd, J=2.7, 8.7 Hz, 1H), 7.83 (d, J=8.7 Hz, 1H), 7.93 (d, J=8.7 Hz, 1H), 7.96 (d, J=2.7 Hz, 1H), 8.69 (d, J=1.8 Hz, 1H). MS (DCI/$NH_3$) $(M+H)^+$ at m/z 497, 499, 501. Analysis calculated for $C_{21}H_{19}N_3O_4Cl_2S_1.0.82H_2O$: C, 50.94; H, 4.20; N, 8.49. Found: C, 50.91; H, 4.21; N, 8.69.

EXAMPLE 33

[(2,4-Dichlorophenyl)[2-nitro-4-(E-((3-(1-pyrrolidin-2-only)propylamino)carbonyl)ethenyl) phenyl]sulfide] *(2,4-Dichlorophenyl)[2-nitro-4-(E-((3-(2-oxopyrrolidin-1-yl)propylamino)carbonyl) ethenyl)phenyl]sulfide*

The title compound was prepared by the procedures described in Example 32 substituting 1-acetylpiperazine with 1-(3-aminopropyl)-2-pyrrolidinone. Light-yellow powder; $^1$H NMR ($d^6$-DMSO, 300 MHz) δ 1.64 (p, J=7.1 Hz, 2H), 1.91 (p, J=7.5 Hz, 2H), 2.21 (t, J=8.3 Hz, 2H), 3.15 (q, J=6.3 Hz, 2H), 3.21 (dd, J=9.9, 17.7 Hz, 2H), 3.32 (overlapping t, J=8.4 Hz, 2H), 6.72 (d, J=15.6 Hz, 1H), 6.86 (d, J=8.7 Hz, 1H), 7.46 (d, J=15.6 Hz, 1H), 7.63 (dd, J=2.4, 8.1 Hz, 1H), 7.79 (dd, J=2.4, 8.7 Hz, 1H), 7.84 (d, J=8.7 Hz, 1H), 7.96 (d, J=2.4 Hz, 1H), 8.18 (t, J=6.0 Hz, 1H), 8.46 (d, J=2.1 Hz, 1H). MS (DCI/$NH_3$) $(M+H)^+$ at m/z 494, 496.

EXAMPLE 34

(2,3-Dichlorophenyl)[2-nitro-4-(E-((4-acetylpiperazin-1-yl)carbonyl)ethenyl)phenyl]sulfide The title compound was prepared by the procedures described in Example 32B substituting 2,4-dichlorothiophenol with 2,3-dichlorothiophenol. Light-yellow powder; $^1$H NMR ($d^6$-DMSO, 300 MHz) δ 2.04 (s, 3H), 3.42–3.50 (br m, 4H), 3.50–3.64 (br m, 2H), 3.64–3.79 (br m, 2H), 6.88 (d, J=8.7 Hz, 1H), 7.45 (d, J=15.6 Hz, 1H), 7.55 (t, J=7.65 Hz, 1H), 7.57 (d, J=15.6 Hz, 1H), 7.78 (dd, J=1.8, 8.1 Hz, 1H), 7.87 (dd, J=1.8, 8.1 Hz, 1H), 7.95 (dd, J=2.7, 9.0 Hz, 1H), 8.69 (d, J=1.8 Hz, 1H). MS (DCI/$NH_3$) $(M+H)^+$ at m/z 497, 499, 501.

EXAMPLE 35

(4-Bromophenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 4-bromothiophenol. Light-yellow powder; $^1$H NMR ($d^6$-DMSO, 300 MHz) δ 2.04 (s, 3H), 3.47 (br m, 4H), 3.52 (br m, 1H), 3.60 (br m, 1H), 3.68 (br m, 1H), 3.74 (br m, 1H), 6.90 (d, J=8.7 Hz, 1H), 7.43 (d, J=15.0 Hz, 1H), 7.54 (d, J=15.0 Hz, 1H), 7.58 (d, J=9.0 Hz, 2H), 7.78 (d, J=9.0 Hz, 2H), 7.92 (dd, J=2.1, 9.0 Hz, 1H), 8.65 (d, J=2.1 Hz, 1H). MS (DCI/$NH_3$) $(M+H)^+$ at m/z 507, 509.

EXAMPLE 36

(4-Methylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with p-thiocresol. Light-yellow powder; $^1$H NMR ($d^6$-DMSO, 300 MHz) δ 2.04 (s, 3H), 2.39 (s, 3H), 3.47 (br m, 4H), 3.52 (br m, 1H), 3.60 (br m, 1H), 3.68 (br m, 1H), 6.89 (d, J=8.7 Hz, 1H), 7.20 (d, J=8.1 Hz, 1H), 7.39 (d, J=8.4 Hz, 2H), 7.40 (d, J=15.0 Hz, 1H), 7.53 (d, J=15.0

Hz, 1H), 7.54 (d, J=8.4 Hz, 2H), 7.89 (dd, J=2.1, 8.7 Hz, 1H), 8.64 (d, J=2.1 Hz, 1H). MS (DCI/$NH_3$) $(M+NH_4)^+$ at m/z 443.

EXAMPLE 37

(2,4-Dichlorophenyl)[2-nitro-4-(E-((4-(tert-butoxycarbonyl)piperazin-1-yl)carbonyl)ethenyl) phenyl]sulfide The title compound was prepared by the procedures described in Example 32 substituting 1-acetylpiperazine with tert-butyl piperazine carboxylate. Light-yellow powder; $^1$H NMR ($d^6$-DMSO, 300 MHz) δ 1.42 (s, 9H), 3.36 (overlapping m, 4H), 3.55 (br m, 2H), 3.70 (br m, 2H), 6.83 (d, J=8.7 Hz, 1H), 7.42 (d, J=15.6 Hz, 1H), 7.54 (d, J=15.6 Hz, 1H), 7.63 (dd, J=2.4, 8.4 Hz, 1H), 7.83 (d, J=8.7 Hz, 1H), 7.92 (dd, J=2.4, 8.7 Hz, 1H), 7.96 (d, J=2.7 Hz, 1H), 8.68 (d, J=2.4 Hz, 1H). MS (APCI) $(M+H)^+$ at m/z 538, 540, 542.

EXAMPLE 38

(2,4-Dichlorophenyl)[2-nitro-4-(E-((4-(2-furoylcarbonyl)piperazin-1-yl)carbonyl)ethenyl) phenyl]sulfide

EXAMPLE 38A 2,4-Dichlorophenyl[2-nitro-4-(E-((piperazin-1-yl) carbonyl)ethenyl)phenyl]sulfide Trifluoroacetic Acid Salt The compound (100 mg, 0.186 mmol) from Example 37 was dissolved in 0.5 mL of neat trifluoroacetic acid (TFA). The mixture was stirred at room temperature for 1 hour. The TFA was then removed under vacuum to give the title compound (105 mg) as a yellow solid.

EXAMPLE 38B (2,4-Dichlorophenyl)[2-nitro-4-(E-((4-(2-furoylcarbonyl)piperazin-1-yl)carbonyl)ethenyl) phenyl]sulfide To a stirred solution of piperazine TFA salt (35 mg, 0.067 mmol) from Example 38A in 2.0 mL of $CH_2Cl_2$ was added $Et_3N$ (23 μL, 0.17 mmol), 4-dimethylaminopyridine (DMAP) (1.0 mg, 0.0082 mmol), and furyl chloride (8.0 μL, 0.080 mmol). The mixture was then stirred at room temperature for 30 minutes before the solvent was removed. The crude product was purified with Gilson HPLC system, YMC C-18 column, 75×30 mm I.D., S-5 μM, 120 Å, and a flow rate of 25 mL/min, λ=214, 245 nm; mobile phase A, 0.05 M [$NH_4$Oac] *$NH_4OAc$*, and B, $CH_3CN$; linear gradient 20–100% of B in 20 minutes to give the title compound (24 mg, 67%) as *a* light-yellow powder; $^1$H NMR ($d^6$-DMSO, 300 MHz) δ 3.62–3.87 (br m, 8H), 6.66 (q, J=2.1 Hz, 1H), 6.84 (d, J=8.7 Hz, 1H), 7.04 (d, J=3.3 Hz, 1H), 7.44 (d, J=15.3 Hz, 1H), 7.56 (d, J=15.3 Hz, 1H), 7.63 (dd, J=2.4, 8.1 Hz, 1H), 7.83 (d, J=8.4 Hz, 1H), 7.87 (d, J=2.1 Hz, 1H), 7.92 (dd, J=2.1, 12.0 Hz, 1H), 7.96 (d, J=2.1 Hz, 1H), 8.70 (d, J=2.1 Hz, 1H). MS (APCI) $(M+H)^+$ at m/z 532, 534, 536.

EXAMPLE 39

(2,4-Dichlorophenyl)[2-nitro-4-(E-((4-(methanesulfonyl)piperazin-1-yl)carbonyl)ethenyl) phenyl]sulfide The title compound was prepared by the procedures described in Example 38B substituting furoyl chloride with methanesulfonyl chloride. Light-yellow powder; $^1$H NMR ($d^6$-DMSO, 300 MHz) δ 2.90 (s, 3H), 3.25 (br m, 4H), 3.68 (br m, 2H), 3.83 (br m, 2H), 6.84 (d, J=9.0 Hz, 1H), 7.45 (d, J=15.6 Hz, 1H), 7.56 (d, J=15.6 Hz, 1H), 7.63 (dd, J=2.4, 8.7 Hz, 1H), 7.83 (d, J=9.0 Hz, 1H), 7.93 (dd, J=2.1, 9.0 Hz, 1H), 7.95 (d, J=2.7 Hz, 1H), 8.70 (d, J=2.1 Hz, 1H). MS (ESI) $(M+H)^+$ at m/z 516, 518, 520.

EXAMPLE 40

(2,4-Dichlorophenyl)[2-nitro-4-(E-((4-(diethylaminocarbonylmethyl)piperazin-1-yl) carbonyl)ethenyl)phenyl]sulfide The title compound was prepared by the procedures described in Example 38B substituting furoyl chloride with 2-chloro-N,N-diethylacetamide. Light-yellow powder; $^1$H NMR ($d^6$-DMSO, 300 MHz) δ 1.01 (t, J=7.2 Hz, 3H), 1.13 (t, J=7.2 Hz, 3H), 2.46 (br m, 4H), 3.16 (s, 2H), 3.24 (q, J=7.2 Hz, 2H), 3.37 (q, J=7.2 Hz, 2H), 3.56 (br m, 2H), 3.69 (br m, 2H), 6.83 (d, J=9.0 Hz, 1H), 7.46 (d, J=15.3 Hz, 1H), 7.52 (d, J=15.3 Hz, 1H), 7.62 (dd, J=2.4, 8.7 Hz, 1H), 7.82 (d, J=9.0 Hz, 1H), 7.92 (dd, J=2.1, 9.0 Hz, 1H), 7.95 (d, J=2.7 Hz, 1H), 8.67 (d, J=2.1 Hz, 1H). MS (ESI) $(M+NH_4)^+$ at m/z 573, 575, 577.

EXAMPLE 41

(2,4-Dichlorophenyl)[2-nitro-4-(E-((4-(diethylaminocarbonyl)piperazin-1-yl)carbonyl) ethenyl)phenyl]sulfide The title compound was prepared by the procedures described in Example 38B substituting furoyl chloride with N,N-diethylcarbamyl chloride. Light-yellow powder; $^1$H NMR ($d^6$-DMSO, 300 MHz) δ 1.06 (t, J=6.9 Hz, 6H), 3.12 (br m, 4H), 3.15 (q, J=6.9 Hz, 4H), 3.58 (br m, 2H), 3.72 (br m, 2H), 6.83 (d, J=8.7 Hz, 1H), 7.42 (d, J=15.6 Hz, 1H), 7.53 (d, J=15.6 Hz, 1H), 7.63 (dd, J=2.7, 9.0 Hz, 1H), 7.82 (d, J=8.7 Hz, 1H), 7.92 (dd, J=2.4, 8.7 Hz, 1H), 7.95 (d, J=2.7 Hz, 1H), 8.68 (d, J=2.1 Hz, 1H). MS (APCI) $(M+H)^+$ at m/z 537, 539, 541.

EXAMPLE 42

(2,4-Dichlorophenyl)[2-nitro-4-(E-((4-(tert-butoxycarbonylmethyl)piperazin-1-yl)carbonyl) ethenyl)phenyl]sulfide The title compound was prepared by the procedures described in Example 38B substituting $CH_2CL_2$ with $CH_3CN$ as solvent, and furoyl chloride with tert-butyl bromoacetate. Light-yellow powder; $^1$H NMR ($CDCl_3$, 300 MHz) δ 1.47 (s, 9H), 2.70 (br m, 4H), 3.21 (s, 2H), 3.74 (br m, 2H), 3.82 (br m, 2H), 6.73 (d, J=8.7 Hz, 1H), 6.92 (d, J=15.0 Hz, 1H), 7.39 (dd, J=2.4, 8.7 Hz, 1H), 7.47 (d, J=8.7 Hz, 1H), 7.61 (d, J=15.0 Hz, 1H), 7.62 (d, J=2.4 Hz, 1H), 7.66 (d, J=8.7 Hz, 1H), 8.43 (br d, 1H). MS (APCI) $(M+H)^+$ at m/z 552, 554, 556.

EXAMPLE 43

(2,4-Dichlorophenyl)[2-nitro-4-(E-((4-(carboxycarbonyl)piperazin-1-yl)carbonyl)ethenyl) phenyl]sulfide

EXAMPLE 43A (2,4-Dichlorophenyl)[2-nitro-4-(E-((4-carbethoxycarbonyl)piperazin-1-yl)carbonyl) ethenyl)phenyl]sulfide The title compound was prepared by the procedures described in Example 38B substituting furoyl chloride with ethyl oxalyl chloride.

EXAMPLE 43B (2,4-Dichlorophenyl)[2-nitro-4-(E-((4-(carboxycarbonyl)piperazin-1-yl)carbonyl)ethenyl)phenyl]sulfide To a stirred solution of the ethyl ester (40 mg, 0.074 mmol) from Example 43A in 2 mL of ethanol was added saturated LiOH (0.25 mL). The mixture was then stirred at room temperature for 2 hours. Water (2 mL) was then added to the reaction mixture, which was then acidified to pH=2 with concentrated HCl. The precipitates were collected through filtration, washed with cold water, dried under vacuum to give the [titled] *title* compound (30 mg, 79%) as *a* light yellow solid. $^1$H NMR (d$^6$-DMSO, 300 MHz) δ 3.52 (br m, 4H), 3.62 (br m, 2H), 3.76 (br m, 2H), 6.84 (d, J=9.0 Hz, 1H), 7.46 (d, J=15.3 Hz, 1H), 7.56 (d, J=15.3 Hz, 1H), 7.63 (dd, J=2.7, 8.7 Hz, 1H), 7.83 (d, J=9.0 Hz, 1H), 7.93 (d, J=9.0 Hz, 1H), 7.96 (d, J=2.7 Hz, 1H), 8.70 (br d, 1H). MS (APCI) (M—COO)$^+$ at m/z 466, 468, 470.

EXAMPLE 44

(2,4-Dichlorophenyl)[2-nitro-4-(E-((4-(carboxymethyl)piperazin-1-yl)carbonyl)ethenyl)phenyl]sulfide The title compound was prepared by the procedures described in Example 38A substituting compound from Example 37 with compound from Example 42. Light-yellow powder; $^1$H NMR (d$^6$-DMSO, 300 MHz) δ 3.14 (s, 2H), 3.40 (overlapping br m, 4H), 3.44 (br m, 1H), 3.51 (br m, 1H), 3.57 (br m, 1H), 3.71 (br m, 1H), 6.82 (d, J=8.7 Hz, 1H), 7.42 (d, J=15.6 Hz, 1H), 7.52 (d, J=15.6 Hz, 1H), 7.63 (dd, J=2.4, 8.7 Hz, 1H), 7.83 (d, J=8.7 Hz, 1H), 7.92 (dd, J=2.4, 8.7 Hz, 1H), 7.96 (d, J=2.4 Hz, 1H), 8.68 (d, J=2.4 Hz, 1H). MS (APCI) (M+H)$^+$ at m/z 496, 498, 500.

EXAMPLE 45

(2-Methylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with o-thiocresol. Light-yellow powder; $^1$H NMR (d$^6$-DMSO, 300 MHz) δ 2.03 (s, 3H), 2.29 (s, 3H), 3.47 (br m, 4H), 3.53 (br m, 1H), 3.60 (br m, 1H), 3.67 (br m, 1H), 3.83 (br m, 1H), 6.64 (d, J=8.7 Hz, 1H), 7.40 (d, J=15.0 Hz, 1H), 7.36–7.42 (m, 1H), 7.46–7.57 (m, 3H), 7.63 (d, J=6.9 Hz, 1H), 7.89 (dd, J=2.4, 9.0 Hz, 1H), 8.66 (d, J=2.4 Hz, 1H). MS (APCI) (M+H)$^+$ at m/z 426.

EXAMPLE 46

(2-Chlorophenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-chlorothiophenol. Light-yellow powder; $^1$H NMR (d$^6$-DMSO, 300 MHz) δ 2.04 (s, 3H), 3.47 (br m, 4H), 3.52 (br m, 1H), 3.60 (br m, 1H), 3.68 (br m, 1H), 3.73 (br m, 1H), 6.75 (d, J=9.0 Hz, 1H), 7.43 (d, J=15.3 Hz, 1H), 7.54 (d, J=15.3 Hz, 1H), 7.55 (dd, J=1.8, 8.1 Hz, 1H), 7.64 (t, J=1.8, 8.1 Hz, 1H), 7.76 (d, J=1.8, 8.1 Hz, 1H), 7.82 (d, J=1.8, 8.1 Hz, 1H), 7.93 (dd, J=2.4, 9.0 Hz, 1H), 8.68 (d, J=2.4 Hz, 1H). MS (APCI) (M+H)$^+$ at m/z 446, 448, 450.

EXAMPLE 47

(2-Aminophenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-aminothiophenol. Light-yellow powder; $^1$H NMR (d$^6$-DMSO, 300 MHz) δ 2.04 (s, 3H), 3.47 (br m, 4H), 3.52 (br m, 1H), 3.60 (br m, 1H), 3.68 (br m, 1H), 3.74 (br m, 1H), 5.58 (s, 2H), 6.65 (td, J=1.5, 15.0 Hz, 1H), 6.72 (dd, J=1.5, 8.7 Hz, 1H), 7.00 (dd, J=1.8, 8.7 Hz, 1H), 7.27 (t, J=1.5, 8.6 Hz, 1H), 7.36 (dd, J=1.5, 8.7 Hz, 1H), 7.39 (d, J=15.3 Hz, 1H), 7.53 (d, J=15.3 Hz, 1H), 7.89 (dd, J=1.8, 8.7 Hz, 1H), 8/64 (d, J=1.8 Hz, 1H). MS (APCI) (M+H)$^+$ at m/z 427.

EXAMPLE 48

(2-Hydroxymethylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-mercaptobenzyl alcohol. Light-yellow powder; $^1$H NMR (d$^6$-DMSO, 300 MHz) δ 2.03 (s, 3H), 3.47 (br m, 4H), 3.52 (br m, 1H), 3.60 (br m, 1H), 3.67 (br m, 1H), 3.73 (br m, 1H), 4.53 (d, J=5.7 Hz, 1H), 5.34 (t, J=5.7 Hz, 1H), 6.65 (d, J=8.7 Hz, 1H), 7.40 (d, J=15.3 Hz, 1H), 7.46 (d, J=7.8 Hz, 1H), 7.53 (d, J=15.3 Hz, 1H), 7.59 (d, J=7.5 Hz, 1H), 7.64 (d, J=7.5 Hz, 1H), 7.87 (dd, J=2.1, 8.7 Hz, 1H), 8.65 (d, J=2.1 Hz, 1H). MS (APCI) (M+NH$_4$)$^+$ at m/z 459.

EXAMPLE 49

(2-Ethylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-ethylthiophenol. Light-yellow powder; $^1$H NMR (d$^6$-DMSO, 300 MHz) δ 1.01 (t, J=7.65 Hz, 3H), 2.04 (s, 3H), 2.69 (q, J=7.65 Hz, 2H), 3.47 (br m, 4H), 3.52 (br m, 1H), 3.59 (br m, 1H), 3.67 (br m, 1H), 3.73 (br m, 1H), 6.64 (d, J=8.7 Hz, 1H), 7.38 (dd, J=2.4, 7.5 Hz, 1H), 7.40 (d, J=15.6 Hz, 1H), 7.50–7.61 (m, 3H), 7.53 (d, J=15.6 Hz, 1H), 7.89 (dd, J=2.4, 8.7 Hz, 1H), 8.64 (d, J=2.4 Hz, 1H). MS (APCI) (M+Cl)$^-$ at m/z 474, 476.

EXAMPLE 50

(2-iso-Propylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-isopropylthiophenol. Light-yellow powder; $^1$H NMR (d$^6$-DMSO, 300 MHz) δ 1.05 (d, J=6.9 Hz, 6H), 2.04 (s, 3H), 3.47 (br m, 4H), 3.52 (br m, 1H), 3.60 (br m, 1H), 3.67 (br m, 1H), 3.72 (br m, 1H), 6.64 (d, J=8.4 Hz, 1H), 7.34–7.41 (m, 2H), 7.39 (d, J=15.3 Hz, 1H), 7.52 (d, J=15.3 Hz, 1H), 7.56–7.73 (m, 2H), 7.90 (dd, J=2.1, 8.7 Hz, 1H), 8.64 (d, J=2.1 Hz, 1H). MS (APCI) (M+NH$_4$)$^{30}$ at m/z 471. Analysis calculated for $C_{24}H_{27}N_3O_4S_1$.0.21$H_2O$: C, 63.03; H, 5.96; N, 9.13. Found: C, 63.03; H, 6.04; N, 9.19.

EXAMPLE 51

(2-tert-Butylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-tert-butylthiophenol. Light-yellow powder; $^1$H NMR (d$^6$-DMSO, 300 MHz) δ 1.46 (s, 9H), 2.04 (s, 3H), 3.47 (br m, 4H), 3.52 (br m, 1H), 3.60 (br m, 1H), 3.67 (br m, 1H), 3.73 (br m, 1H), 6.68 (d, J=8.7 Hz, 1H), 7.35 (t, J=7.5 Hz, 1H), 7.39 (d, J=15.3 Hz, 1H), 7.45–7.57 (m, 2H), 7.50 (d, J=15.3 Hz, 1H), 7.65 (d, J=8.1 Hz, 1H), 7.88 (dd, J=2.4, 8.7 Hz, 1H), 8.64 (d, J=2.4 Hz, 1H). MS (APCI) $(M+NH_4)^+$ at m/z 485.

EXAMPLE 52

(2-Chlorophenyl)[2-chloro-4-(E-((4-acetylpiperazin-1-yl)carbonyl))2-propenyl)phenyl]sulfide

EXAMPLE 52A

3'-Chloro-4'-[(2-chlorophenyl)thio]acetophenone

The title compound was prepared by the procedures described in Example 1A substituting 2,4-dichlorothiophenol with 2-chlorothiophenol, and 2-chlorobenzaldehyde with 4'-fluoro-3'-chloroacetophenone.

EXAMPLE 52B (2-Chlorophenyl)[2-chloro-4-(E-(1-ethoxycarbonyl) 2-propenyl)phenyl]sulfide To a stirred suspension of NaH (60% in mineral oil, 121 mg, 3.03 mmol) in 20 mL of anhydrous THF under nitrogen atmosphere was added triethyl phosphonoacetate dropwise. After 20 minutes, the acetophenone (600 mg, 2.02 mmol) from Example 52A in THF (5 mL) was added in one portion. The resulting clear solution was then stirred at room temperature for 7 hours. Reaction was then stopped, most of the solvent was evaporated, and the residue was partitioned between EtOAc (2×20 mL) and water. The combined organic layer was washed with water and brine, dried over $Na_2SO_4$, concentrated in vacuo. The crude product was purified using silica gel flash column chromatography eluting with 5–10% $Et_2O$ in hexanes to give the (E)-isomer of the cinnamate (500 mg, 68%) as a white solid.

EXAMPLE 52C (2-Chlorophenyl)[2-chloro-4-(E-(1-carboxy)2-propenyl)phenyl]sulfide

A mixture of the cinnamate (500 mg, 1.37 mmol) from Example 52B in 5 mL of EtOH/THF (4:1) was stirred with sat. LiOH solution (0.50 mL) at 50° C[.] for 2 hours. The mixture was then acidified with 3N HCl and extracted with $CH_2Cl_2$ (3×10 mL). The combined organic layer was dried over $MgSO_4$, concentrated under reduced pressure to give the [titled] *title* compound (450 mg, 97%) as a white solid.

EXAMPLE 52D (2-Chlorophenyl)[2-chloro-4-(E-((4-acetylpiperazin-1-yl)carbonyl))2-propenyl)phenyl]sulfide The title compound was prepared using the cinnamic acid from Example 52C by the procedures described in Example 1C substituting 6-amino-1-hexanol with 1-acetylpiperazine. White solid; $^1H$ NMR ($CDCl_3$, 300 MHz) δ 2.10–2.20 (m, 3H), 2.25 (s, 3H), 3.40–3.80 (m, 8H), 6.28 (s, 1H), 7.00 (d, J=8.7 Hz, 1H), 7.19–7.36 (m, 4H), 7.46–7.56 (m, 2H). MS (APCI) $(M+NH_4)^+$ at m/z 466, 468, 470.

EXAMPLE 53

(2-(1-Morpholinylmethyl)phenyl)[2-chloro-4-(E-((1-morpholinyl)carbonyl)ethenyl)phenyl]sulfide

EXAMPLE 53A (2-(1-Bromomethyl)phenyl)[2-chloro-4-(E-((1-morpholinyl)carbonyl)ethenyl)phenyl]sulfide To a stirred solution of benzyl alcohol (195 mg, 0.32 mmol) from Example 11 in 2.0 mL of anhydrous DMF was added LiBr (48 mg, 0.35 mmol). The mixture was then cooled in an ice-water bath, and $PBr_3$ (60 μL, 0.40 mmol) was dropped in slowly. The ice bath was then removed and the mixture was stirred at room temperature for 1 hour. Water was then added, the mixture was then partitioned between EtOAc and aqueous $NaHCO_3$. The aqueous layer was extracted with EtOAc once. The combined organic layer was washed with water and brine, dried over $Na_2SO_4$, concentrated on a rotavap. The crude bromide (230 mg) was used directly for the alkylation without purification.

EXAMPLE 53B (2-(1-Morpholinylmethyl)phenyl)[2-chloro-4-(E-((1-morpholinyl)carbonyl)ethenyl)phenyl]sulfide To a stirred solution of morpholine (10 μL, 0.11 mmol) in 0.5 mL of $CH_3CN$ was added Hunig base (23.7 μL, 0.14 mmol), followed by the bromide (40 mg, 0.091 mmol). The mixture was then stirred at room temperature for 2 hours. Solvent was then removed and the crude product was purified with Gilson Preparative HPLC as described in Example 38B to give the [titled] *title* compound as a white solid. $^1H$ NMR ($d^6$-DMSO, 300 MHz) δ 2.33 (br t, 4H), 3.45 (br t, 4H), 3.50–3.65 (m, 6H), 3.56 (s, 2H), 3.65–3.80 (br m, 2H), 6.74 (d, J=8.7 Hz, 1H), 7.30 (d, J=15.3 Hz, 1H), 7.35–7.41 (m, 2H), 7.43 (d, J=15.3 Hz, 1H), 7.46 (td, J=2.4, 8.1 Hz, 1H), 7.52 (dd, J=2.1, 8.7 Hz, 1H), 7.56 (d, J=8.1 Hz, 1H), 8.02 (d, J=2.1 Hz, 1H). MS $(DCI/NH_3)$ $(M+H)^+$ at m/z 459, 461.

EXAMPLE 54

(2-(4-(1,3-Benzodioxolyl-5-methyl)piperazin-1-ylmethyl)phenyl)[2-chloro-4-(E-((1-morpholinyl) carbonyl)ethenyl)phenyl]sulfide The title compound was prepared by the procedures described in Example 53B substituting morpholine with 1-piperonylpiperazine. White solid; $^1H$ NMR ($d^6$-DMSO, 300 MHz) δ 2.13–2.40 (br m, 8H), 3.28 (s, 2H), 3.49–3.64 (br m, 6H), 3.54 (s, 2H), 3.70 (br m, 2H), 5.97 (s, 2H), 6.69 (dd, J=1.8, 8.1 Hz, 1H), 6.74 (d, J=8.7 Hz, 1H), 6.79 (d, J=1.8 Hz, 1H), 6.81 (d, J=8.1 Hz, 1H), 7.39 (d, J=15.3 Hz, 1H), 7.33–7.38 (m, 2H), 7.38–7.50 (m, 2H), 7.43 (d, J=15.3 Hz, 1H), 7.53 (d, J=8.4 Hz, 1H), 8.00 (d, J=2.1 Hz, 1H). MS $(DCI/NH_3)$ $(M+H)^+$ at m/z 592, 594.

EXAMPLE 55

(2-(4-(iso-Propylaminocarbonylmethyl)piperazin-1-ylmethyl)phenyl)[2-chloro-4-(E-((1-morpholinyl) carbonyl)ethenyl)phenyl]sulfide The title compound was prepared by the procedures described in Example 53B substituting morpholine with N-isopropyl-1-piperazineacetamide. White solid; $^1H$ NMR ($d^6$-DMSO, 300 MHz) δ 1.04 (d, J=6.3 Hz, 6H), 2.20–2.42 (br m, 8H), 2.78 (s, 2H), 3.47–3.64 (br m, 6H), 3.56 (s, 2H), 3.64–3.76 (br m, 2H), 3.85 (qd, J=6.3, 8.1 Hz, 1H), 6.73 (d, J=8.7 Hz, 1H), 7.29 (d, J=15.6 Hz, 1H), 7.31–7.39 (m, 2H), 7.43 (d, J=15.6 Hz, 1H), 7.45 (td, J=2.7, 6.3 Hz, 1H), 7.50 (dd, J=2.1, 8.7 Hz, 1H), 7.55 (d, J=7.8 Hz, 1H), 8.00 (d, J=2.1 Hz, 1H). MS $(DCI/NH_3)$ $(M+H)^+$ at m/z 557, 559.

EXAMPLE 56

(2-((N-Ethoxycarbonylmethyl-N-methyl) aminomethyl)phenyl)[2-chloro-4-(E-((1-morpholinyl)carbonyl)ethenyl)phenyl]sulfide The title compound was prepared by the procedures described in Example 53B substituting morpholine with ethyl sarcosinate hydrochloride. White solid; $^1$H NMR ($d^6$-DMSO, 300 MHz) δ 1.16 (t, J=7.2 Hz, 3H), 2.27 (s, 2H), 3.30 (s, 2H), 3.51–3.66 (br m, 6H), 3.66–3.75 (br m, 2H), 3.78 (s, 2H), 4.05 (q, J=7.2 Hz, 2H), 6.75 (d, J=8.7 Hz, 1H), 7.30 (d, J=15.3 Hz, 1H), 7.33–7.38 (m, 2H), 7.42–7.50 (m, 2H), 7.43 (d, J=15.3 Hz, 1H), 7.53 (dd, J=2.1, 8.7 Hz, 1H), 7.60 (d, J=7.8 Hz, 1H), 8.02 (d, J=2.1 Hz, 1H). MS (DCI/$NH_3$) $(M+H)^+$ at m/z 489, 491.

EXAMPLE 57

(2-Formylphenyl)[2-chloro-4-(E-((1-morpholinyl) carbonyl)ethenyl)phenyl]sulfide

To a stirred solution of the alcohol (368 mg, 0.94 mmol) from Example 11 in 5 mL of anhydrous acetonitrile was added activated 4 Å molecular sieves, TPAP (3.3 mg, 0.0094 mmol), and NMO (110 mg, 1.03 mmol). The mixture was then stirred at room temperature for 3 hours. The reaction mixture was then quenched with dimethyl sulfide (100 μL). The crude product was filtered through celite, washed with acetonitrile, *and* condensed in vacuo. The [titled] *title* compound was purified by silica gel column chromatography to give a white solid (216 mg, 59%). $^1$H NMR ($d^6$-DMSO, 300 MHz) δ 3.60 (br m, 6H), 3.73 (br m, 2H), 7.00 (d, J=8.4 Hz, 1H), 7.40 (d, J=15.3 Hz, 1H), 7.42 (d, J=8.4 Hz, 1H), 7.51 (d, J=15.3 Hz, 1H), 7.52 (td, J=1.8, 8.1 Hz, 1H), 7.61 (td, J=1.8, 8.1 Hz, 1H), 7.71 (dd, J=2.1, 8.4 Hz, 1H), 8.02 (dd, J=2.1, 8.4 Hz, 1H), 8.14 (d, J=2.1 Hz, 1H). MS (DCI/$NH_3$) $(M+H)^+$ at m/z 388, 390.

EXAMPLE 58

(2-(4-Formylpiperazin-1-ylmethyl)phenyl)[2-chloro-4-(E-((1-morpholinyl)carbonyl)ethenyl)phenyl] sulfide The title compound was prepared by the procedures described in Example 53B substituting morpholine with 1-formyl piperazine. White solid; $^1$H NMR ($d^6$-DMSO, 300 MHz) δ 2.20–2.32 (m, 6H), 2.74 (br m, 2H), 3.48 (s, 2H), 3.59 (m, 6H), 3.70 (br m, 2H), 6.74 (d, J=8.7 Hz, 1H), 7.29 (d, J=15.6 Hz, 1H), 7.35–7.41 (m, 2H), 7.42 (d, J=15.6 Hz, 1H), 7.45–7.52 (m, 3H), 7.98 (d, J=2.1, 1H). MS (DCI/$NH_3$) $(M+H)^+$ at m/z 486, 488.

EXAMPLE 59

(2-(E-((1-Morpholinyl)carbonyl)ethenyl)phenyl)[2-chloro-4-(E-((1-morpholinyl)carbonyl)ethenyl) phenyl]sulfide A mixture of bromide (80 mg, 0.18 mmol) from Example 12, acryloylmorpholine (33 mg, 0.23 mmol), $Pd(Oac)_2$ (2.0 mg, 0.009 mmol), $P(o\text{-tolyl})_3$ (17 mg, 0.056 mmol), $Et_3N$ (39 μL, 0.27 mmol), and anhydrous DMF (1.0 mL) in a pressure tube was flushed with nitrogen for 5 minutes before it *was* capped and heated at 110° C[. over night] *overnight*. TLC indicated almost complete consumption of the starting bromide. The reaction mixture was then allowed to cool [down] to room temperature[.] *and* partitioned between EtOAc and water. The aqueous layer was extracted once with EtOAc. The combined organic layer was washed with water and brine, dried over $Na_2SO_4$[.] *and* condensed under reduced pressure. The crude product was purified with Gilson Preparative HPLC as described in Example 38B to give the [titled] *title* compound as a light-brown solid (35 mg, 39%). $^1$H NMR ($d^6$-DMSO, 300 MHz) δ 3.43–3.88 (m, 16H), 6.58 (d, J=8.7 Hz, 1H), 7.30 (d, J=15.3 Hz, 2H), 7.43 (d, J=15.3 Hz, 1H), 7.47–7.64 (m, 4H), 7.86 (d, J=15.3 Hz, 1H), 8.06 (d, J=2.1 Hz, 1H), 8.14 (d, J=7.5 Hz, 1H). MS (DCI/$NH_3$) $(M+NH_4)^+$ m/z 516, 518. Analysis calculated for $C_{26}H_{27}N_2O_4Cl_1S_1.0.46H_2O$: C, 61.56; H, 5.55; N, 5.21. Found: C, 61.56; H, 5.50; N, 5.43.

EXAMPLE 60

(2-Formylphenyl)[2-nitro-4-(E-((4-acetylpiperazin-1-yl)carbonyl)ethenyl)phenyl]sulfide The title compound was prepared by the procedures described in Example 57 substituting compound from Example 11 with compound from Example 48. Yellow solid; $^1$H NMR ($d^6$-DMSO, 300 MHz) δ 2.04 (s, 3H), 3.47 (br m, 4H), 3.52 (br m, 1H), 3.60 (br m, 1H), 3.68 (br m, 1H), 3.74 (br m, 1H), 6.85 (d, J=8.4 Hz, 1H), 7.44 (d, J=15.6 Hz, 1H), 7.55 (d, J=15.6 Hz, 1H), 7.61 (d, J=7.5 Hz, 1H), 7.73 (t, J=7.5 Hz, 1H), 7.80 (td, J=2.4, 7.5 Hz, 1H), 7.92 (dd, J=2.1, 9.0 Hz, 1H), 8.04 (dd, J=2.4, 7.5 Hz, 1H), 8.66 (d, J=2.1 Hz, 1H), 10.29 (s, 1H). MS (APCI) $(M+Cl)^-$ at m/z 474, 476.

EXAMPLE 61

(2-Formylphenyl)[2-chloro-4-(E-((1-morpholinyl) carbonyl)ethenyl)phenyl]sulfide, N,N-dimethyl hydrazone A mixture of the aldehyde (20 mg, 0.052 mmol) from Example 57, 1,1-dimethyl hydrazine (3.9 μL, 0.052 mmol) in 0.5 mL of EtOH with a tiny amount of AcOH was stirred at room temperature [over night] *overnight*. The solvent was then removed and the product was purified by preparative TLC to give the [titled] *title* compound (20 mg, 90%) as a white solid. $^1$H NMR ($CDCl_3$, 300 MHz) δ 2.91 (s, 6H), 3.55–3.82 (br m, 8H), 6.64 (d, J=8.7 Hz, 1H), 6.76 (d, J=15.3 Hz, 1H), 7.05 (dd, J=1.8, 8.7 Hz, 1H), 7.26 (td, J=1.8, 7.8 Hz, 1H), 7.43 (t, J=7.8 Hz, 1H), 7.47–7.57 (m, 2H), 7.54 (m, 2H), 8.04 (dd, J=1.8, 8.7 Hz, 1H). MS (DCI/$NH_3$) $(M+H)^+$ at m/z 430, 432, 434, 436.

EXAMPLE 62

(2-((3-(1-Morpholinyl)propyl)-1-amino)phenyl)[2-chloro-4-(E-((1-morpholinyl)carbonyl)ethenyl) phenyl]sulfide A mixture of bromide (60 mg, 0.14 mmol) from Example 12, aminopropylmorpholine (24 μL, 0.17 mmol), $Pd_2(dba)_3$ (1.2 mg, 0.0013 mmol), BINAP (2.5 mg, 0.004 mmol), NaOt-Bu (19 mg, 0.20 mmol), 18-crown-6 (50 mg, 0.20 mmol), and anhydrous toluene (1 mL) in a pressure tube was flushed with nitrogen for 3 minutes before it was capped and heated at 80° C[. over night] *overnight*. The reaction was then stopped, and allowed to cool [down] to room temperature. The reaction mixture was partitioned between EtOAc and water, and the aqueous layer was extracted once with EtOAc. The combined organic layer was then washed with water and brine, dried over $Na_2SO_4$, *and* condensed under reduced pressure. The crude product was purified with Gilson Preparative HPLC as described in Example 38B to give the [titled] *title* compound as a light-brown oil (30 mg, 44%). $^1$H NMR ($d^6$-DMSO, 300 MHz) δ 1.62 (quintet, J=6.5 Hz, 2H), 2.15–2.26 (m, 8H), 3.17 (q, J=6.5 Hz, 2H), 3.22–3.76 (m, 12H), 3.50 (t, J=6.5 Hz, 2H), 5.72 (t, J=5.7 Hz, 1H), 6.47 (d, J=8.7 Hz, 1H), 6.68 (t, J=7.2 Hz, 1H), 6.81 (d, J=8.4 Hz, 1H), 7.26 (d, J=15.6 Hz, 1H), 7.35–7.42 (m, 2H), 7.43 (d, J=15.6 Hz, 1H), 7.44 (d, J=8.4 Hz, 1H), 7.49 (d, J=8.4 Hz, 1H), 8.00 (d, J=2.1 Hz, 1H). MS (APCI) $(M+H)^+$ at m/z 502, 504.

EXAMPLE 63

[(2,4-Dichlorophenyl)[2-bromo-4-(E-((3-(1-pyrrolidin-2-only)propylamino)carbonyl)ethenyl) phenyl]sulfide] *(2,4-Dichlorophenyl)[2-bromo-4-(E-((3-(2-oxopyrrolidin-1-yl)propylamino)carbonyl) ethenyl)phenyl]sulfide*

EXAMPLE 63A

[(2,4-Dichlorophenyl)[2-amino-4-(E-((3-(1-pyrrolidin-2-only)propylamino)carbonyl ethenyl) phenyl]sulfide] *(2,4-Dichlorophenyl)[2-amino-4-(E-((3-(2-oxopyrrolidin-1-yl)propylamino)carbonyl) ethenyl)phenyl]sulfide*

A mixture of nitro compound (780 mg, 1.58 mmol) from Example 33, $SnCl_2$ (1.50 g, 7.91 mmol) in 25 mL of anhydrous EtOH was refluxed under nitrogen atmosphere for 90 minutes. The reaction was then allowed to cool [down] to room temperature, quenched with sat. $NaHCO_3$, *and* extracted with EtOAc (2×50 mL). The combined organic layer was washed with water and brine, dried over $Na_2SO_4$, *and* condensed in vacuo to give the crude aniline as *a* yellowish brown solid, which was converted to the bromide without purification.

EXAMPLE 63B

[(2,4-Dichlorophenyl)[2-bromo4-(E-((3-(1-pyrrolidin-2-only)propylamino)carbonyl)ethenyl) phenyl]sulfide] *(2,4-Dichlorophenyl)[2-bromo-4-(E-((3-(2-oxopyrrolidin-1-yl)propylamino)carbonyl) ethenyl)phenyl]sulfide*

To a stirred solution of t-butyl nitrite (57 μL, 0.48 mmol), $CrBr_2$ (87 mg, 0.39 mmol) in 2.0 mL of $CH_3CN$ at room temperature was added a solution of aniline from Example 63A (150 mg, 0.323 mmol) in 1.0 mL of $CH_3CN$. The dark green solution was then heated at 65° C[.] under nitrogen atmosphere for 90 minutes. The reaction mixture was then allowed to cool [down] to room temperature, *and* partitioned between EtOAc and 3N HCl. The organic layer was then washed with brine, dried over $Na_2SO_4$, *and* condensed in vacuo. The crude product was then purified with Gilson Preparative HPLC as described in Example 38B to give the [titled] *title* compound as a light-brown solid (50 mg, 29%). Colorless oil; $^1H$ NMR ($d^6$-DMSO, 300 MHz) δ 1.63 (quintet, J=7.2 Hz, 2H), 1.91 (quintet, J=8.4 Hz, 2H), 2.22 (t, J=8.4 Hz, 2H), 3.09–3.47 (m, 6H), 6.67 (d, J=15.3 Hz, 1H), 7.07 (d, J=8.4 Hz, 1H), 7.32 (d, J=8.7 Hz, 1H), 7.38 (d, J=15.3 Hz, 1H), 7.50 (dd, J=2.4, 8.7 Hz, 1H), 7.57 (dd, J=2.1, 8.4 Hz, 1H), 7.86 (d, J=2.4 Hz, 1H), 7.96 (d, J=2.1 Hz, 1H), 8.13 (t, J=6.0 Hz, 1H). MS (ESI) $(M+H)^+$ at m/z 527, 529, 531, 533.

EXAMPLE 64

(2,4-Dichlorophenyl)[2-bromo-4-(E-((1-morpholinyl)carbonyl)ethenyl)phenyl]sulfide

EXAMPLE 64A

[1-Fluoro-2-formyl-4-(E-((1-morpholinyl)carbonyl) ethenyl)benzene

The title compound was prepared by the procedures described in Example 59 substituting the bromide from Example 12 with 2-fluoro-5-bromobenzaldehyde.

EXAMPLE 64B (2,4-Dichlorophenyl)[2-bromo-4-(E-((1-morpholinyl)carbonyl)ethenyl)phenyl]sulfide The title compound was prepared by the procedures described in Example 32 substituting 4-chloro-3-nitrocinnamide with the compound from Example 64A. White solid: $^1H$ NMR ($d^6$-DMSO, 300 MHz) δ 3.60 (br m, 6H), 3.71 (br m, 2H), 6.82 (d, J=8.7 Hz, 1H), 7.35 (d, J=15.6 Hz, 1H), 7.54 (d, J=15.6 Hz, 1H), 7.55 (dd, J=2.4, 8.7 Hz, 1H), 7.61 (d, J=8.7 Hz, 1H), 7.86 (dd, J=2.4, 8.4 Hz, 1H), 7.91 (d, J=2.4 Hz, 1H), 8.41 (d, J=2.1 Hz, 1H), 10.19 (s, 1H). MS $(DCI/NH_3)$ $(M+H)^+$ at m/z 422, 424, 426, 428.

EXAMPLE 65

(2-Chloro-6-formylphenyl)[2-chloro-4-(E-((4-acetylpiperazin-1-yl)carbonyl)ethenyl)phenyl]sulfide

EXAMPLE 65A (2-Carbomethoxyethyl)[2-chloro-4-(E-((4-acetylpiperazin-1-yl)carbonyl)ethenyl)phenyl]sulfide The title compound was prepared by the procedures described in Example 1 substituting 2,4-dichlorothiophenol with methyl 3-mercaptopropionate, and 6-amino-1-hexanol with 1-acetyl piperazine.

EXAMPLE 65B (2-Chloro-6-formylphenyl)[2-chloro-4-(E-((4-acetylpiperazin-1-yl)carbonyl)ethenyl)phenyl]sulfide To a stirred solution of the compound (105 mg, 0.26 mmol) from Example 65A in 2 mL of THF under nitrogen atmosphere at 0° C[.] was added t-BuOK solution (1.0M, 281 μL, 0.29 mmol). Light orange precipitates appeared immediately. After completion of the addition, the reaction mixture was stirred at room temperature for 1 hour before the solvent was removed on a rotavap under reduced pressure.

The yellow thiolate thus obtained was dissolved in 0.5 mL of DMF, and 2,3-dichlorobenzaldehyde was then added. The mixture was then heated at 80° C[.] under nitrogen for 2 hours. Reaction was then stopped and the solvent was removed under vacuum. The crude product was purified with Gilson Preparative HPLC as described in Example 38B to give the [titled] *title* compound as a white solid (25 mg, 21%). $^1H$ NMR ($CDCl_3$, 300 MHz) δ 2.05 (s, 3H), 3.48–3.58 (m, 2H), 3.58–3.84 (m, 6H), 6.53 (d, J=8.7 Hz, 1H), 6.80 (d, J=15.3 Hz, 1H), 7.19 (dd, J=1.8, 8.7 Hz, 1H), 7.51–7.62 (m, 2H), 7.60 (d, J=15.3 Hz, 1H), 7.84 (dd, J=1.8, 8.4 Hz, 1H), 7.99 (dd, J=1.8, 8.4 Hz, 1H). MS (APCI) $(M+NH_4)^+$ at m/z 480, 482, 484.

Compounds that antagonize the interaction between ICAM-1 and LFA-1 can be identified, and their activities quantitated, using both biochemical and cell-based adhesion assays. A primary biochemical assay measures the ability of the compound in question to block the interaction between the integrin LFA-1 and its adhesion partner ICAM-1, as described below:

ICAM-1/LFA-1 Biochemical Interaction Assay

In the biochemical assay, 100 μL of anti-LFA-1 antibody (ICOS Corporation) at a concentration of 5 μg/[ml]*mL* in Dulbecco's phosphate-buffered saaline (D-PBS) is used to coat wells of a 96-well microtiter plate overnight at 4° C. The wells [are] *were* then washed twice with wash buffer (D-PBS w/o $Ca^{++}$ or $Mg^{++}$, 0.05% Tween 20) and blocked by addition of 200 μL of D-PBS, 5% fish skin gelatin. Recombinant LFA-1 (100 μL of 0.7 μg/[ml]*mL*, ICOS Corporation) in D-PBS [is] *was* then added to each well. Incubation [continues] *continued* for 1 hour at room temperature and the wells [are] *were* washed twice with wash buffer. Serial dilutions of compounds being assayed as ICAM-1/LFA-1 antagonists, *were* prepared as 10 mM stock solutions in dimethyl sulfoxide (DMSO), [are] *were* diluted in D-PBS, 2 mM $MgCl_2$, 1% fish skin gelatin and 50 μL of each dilution *was* added to duplicate wells. This [is] *was* followed by *the* addition of 50 μL of 0.8 μg/[ml] *mL* biotinylated recombinant ICAM-1/Ig (ICOS Corporation) to the wells and the plates [are] *were* incubated at room temperature for 1 hour. The wells [are] *were* then washed twice with wash buffer and 100 μL of Europium-labeled Streptavidin (Wallac Oy) diluted 1:100 in Delfia assay buffer (Wallac Oy), [are] *was then* added to the wells. Incubation [proceeds] *proceeded* for 1 hour at room temperature. The wells [are] *were* washed eight times with wash buffer and 100 μL of enhancement solution (Wallac Oy, cat. No. 1244–105) [are] *was* added to each well. Incubation [proceeds] *proceeded* for 5 minutes with constant mixing. Time-resolved fluorimetry measurements [are] *were* made using [the] *a* Victor 1420 Multilabel Counter (Wallac Oy) and the percent inhibition of each candidate compound [is] *was* calculated using the following equation:

$$\%\ \text{inhibition} = 100 \times \left\{ 1 - \frac{\text{average OD w/compound minus background}}{\text{average OD w/o compound minus background}} \right\}$$

where "background" refers to wells that [are] *were* not coated with anti-LFA-1 antibody.

Compounds of the present invention [exhibit] *exhibited* inhibitory activity in the above assay as follows:

| Compound of Example | % inhibition @ 4 μM |
|---|---|
| 1 | 75 |
| 2 | 73 |
| 3 | 75 |
| 4 | 72 |
| 5 | 73 |
| 6 | 85 |
| 7 | 87 |
| 8 | 74 |
| 9 | 93 |
| 10 | 79 |
| 11 | 87 |
| 12 | 90 |
| 13 | 79 |
| 14 | 82 |
| 15 | 88 |
| 16 | 86 |
| 17 | 84 |
| 18 | 86 |
| 19 | 93 |
| 20 | 82 |
| 21 | 80 |
| 22 | 90 |
| 23 | 90 |
| 24 | 80 |
| 25 | 82 |
| 26 | 94 |
| 27 | 94 |
| 28 | 87 |
| 29 | 84 |
| 30 | 93 |
| 31 | 92 |
| 32 | 92 |
| 33 | 91 |
| 34 | 91 |
| 35 | 89 |
| 36 | 90 |

-continued

| Compound of Example | % inhibition @ 4 μM |
|---|---|
| 37 | 91 |
| 38 | 91 |
| 39 | 86 |
| 40 | 90 |
| 41 | 83 |
| 42 | 56 |
| 43 | 82 |
| 44 | 78 |
| 45 | 88 |
| 46 | 87 |
| 47 | 82 |
| 48 | 89 |
| 49 | 93 |
| 50 | 94 |
| 51 | 84 |
| 52 | 86 |
| 53 | 87 |
| 54 | 86 |
| 55 | 82 |
| 56 | 83 |
| 57 | 90 |
| 58 | 80 |
| 59 | 92 |
| 60 | 95 |
| 61 | 88 |
| 62 | 92 |
| 63 | 82 |
| 64 | 81 |
| 65 | 86 |

Biological relevant activity of the compounds in this invention is confirmed using a cell-based adhesion assay, which measures their ability to block the adherence of JY-8 cells (a human EBV-trasformed B cell line expressing LFA-1 on its surface) to immobilized ICAM-1, as follows:

ICAM-1/JT-8 Cell Adhesion Assay

For [measurment] *measurement* of [inhibotory] *inhibitory* activity in the cell-based adhesion assay, 96-well microtiter plates [are] *were* coated with 70 μL of [recombinat] *recombinant* ICAM-1/Ig (ICOS Corporation) at a concentration of 5 μg/mL in D-PBS [w/o] *without* $Ca^{++}$ [or Mg++] *or* $Mg^{++}$ overnight at 4° C. The wells [are] *were* then washed twice with D-PBS and blocked by addition of 200 μL of D-PBS, 5% fish skin gelatin by incubation for 1 hour at room temperature. Fluorescent tagged JY-8 cells (a human EBV-transformed B cell line [expresing] *expressing* LFA-1 on its surface; 50 μL at $2\times10^6$ cells/[ml]*mL* in RPMI 1640/1% fetal [bovene] *bovine* serum) [are] *were* added to the wells. For fluorescent [labelind] *labelling* of JY-8 cells, $5\times10^6$ cells washed once in RPMI 1640 [are] *were* resuspended in 1 mL of RPMI 1640 containing 2 μM Calceiun AM (Molecular Probes), [are] *were* incubated at 37° C[.] for 30 minutes, and washed once with RPMI-1640/1% fetal bovine serum. Dilutions of compounds to be assayed for ICAM-1/LFA-1 antagonistic activity [are] *were* prepared in RPMI-1640/1% fetal bovine serum from 10 mM stock solutions in DMSO and 50 μL [are] *were* added to duplicate wells. Microtiter plates [are] *were* incubated for 45 minutes at room temperature and the wells [are] *were* washed gently once with RPMI-1640/1% fetal bovine serum. Fluorescent intensity [is] *was* measured in a fluorescent plate reader with an excitation wavelength at 485 nM and an emission wavelength at 530 nM. The percent inhibition of a candidate compound at a given concentration [is] *was* calculated using the following equation:

$$\% \text{ inhibition} = 100 \times \left\{1 - \frac{\text{average OD w/compound}}{\text{average OD w/o compound}}\right\}$$

and these concentration/inhibition data [are] *were* used to generate does response curves, from which $IC_{50}$ values [are] *were* derived. Compounds of the present invention [exhibit] *exhibited* blocking activity in the above assay as follows:

| Compound of Example | $IC_{50}$ nM |
|---|---|
| 1 | 2,100 |
| 2 | 13,000 |
| 3 | 2,500 |
| 4 | 680 |
| 5 | 2,900 |
| 6 | 660 |
| 7 | 1,200 |
| 8 | 2,900 |
| 9 | 130 |
| 10 | 1,500 |
| 11 | 260 |
| 12 | 360 |
| 13 | 1,100 |
| 14 | 790 |
| 15 | 140 |
| 16 | 300 |
| 17 | 5,800 |
| 18 | 130 |
| 19 | 450 |
| 20 | 3,300 |
| 21 | 520 |
| 22 | 200 |
| 23 | 600 |
| 24 | 8,000 |
| 25 | 11,000 |
| 26 | 110 |
| 27 | 160 |
| 28 | 370 |
| 29 | 160 |
| 30 | 250 |
| 32 | 190 |
| 32 | 45 |
| 33 | 300 |
| 34 | 70 |
| 35 | 430 |
| 36 | 320 |
| 37 | 140 |
| 38 | 250 |
| 39 | 250 |
| 40 | 280 |
| 41 | 110 |
| 42 | 520 |
| 43 | 100 |
| 44 | 70 |
| 45 | 50 |
| 46 | 60 |
| 47 | 370 |
| 48 | 200 |
| 49 | 20 |
| 50 | 10 |
| 51 | 690 |
| 52 | 420 |
| 53 | 700 |
| 54 | 360 |
| 55 | 100 |
| 56 | 510 |
| 57 | 220 |
| 58 | 1,600 |
| 59 | 200 |
| 60 | 30 |
| 61 | 540 |
| 62 | 340 |

-continued

| Compound of Example | $IC_{50}$ nM |
|---|---|
| 63 | 850 |
| 65 | 1,200 |

Compounds of the present invention have been demonstrated to act via interaction with the integrin LFA-1, specifically by binding to the interaction domain (I-domain), which is known to be critical for the adhesion of LFA-1 to a variety of cell adhesion molecules. As such, it is expected that these compounds should block the interaction of LFA-1 with other CAM's. This has in fact been demonstrated for the case of ICAM-3. Compounds of the present invention may be evaluated for their ability to block the adhesion of JY-8 cells (a human EBV-transformed B cell line expressing LFA-1 on its surface) to immobilized ICAM-3, as follows:

ICAM-3/JY-8 Cell Adhesion Assay

For measurement of inhibitory activity in the cell-based adhesion assay, 96-well microtiter plates [are] *were* coated with 50 μL of recombinant ICAM-3/Ig (ICOS Corporation) at a concentration of 10 μg/mL in D-PBS [w/o] *without* $Ca^{++}$ or $Mg^{++}$ overnight at 4° C. The wells [are] *were* then washed twice with D-PBS, blocked by addition of 100 μL of D-PBS, 1% bovine serum albumin (BSA) by incubation for 1 hour at room temperature, and washed once with RPMI-1640/5% heat-inactivated fetal bovine serum (adhesion buffer). Dilutions of compounds to be assayed for ICAM-3/LFA-1 antagonistic activity [are] *were* prepared in adhesion buffer from 10 mM stock solutions in DMSO and 100 μL [are] *were* added to duplicate wells. JY-8 cells (a human EBV-transformed B cell line expressing LFA-1 on its surface; 100 μL at $0.75 \times 10^6$ cells/[ml] *mL* in adhesion buffer) [are] *were* then added to the wells. Microtiter plates [are] *were* incubated for 30 minutes at room temperature; the adherent cells [are] *were* then fixed with 50 μL of 14% glutaraldehyde/D-PBS and *were* incubated for an additional 90 minutes. The wells [are] *were* washed gently with $dH_2O$; 50 μL of $dH_2O$ [is] *was* added, [following] *followed* by 50 μL of 1% crystal violet. After 5 minutes the plates [are] *were* washed 3[×] *times* with $dH_2O$; 75 μL of $dH_2O$ and 225 μL of 95% EtOH [are] *were* added to each well to extract the crystal violet from the cells. Absorbance [is] *was* measured at 570 nM in an ELISA plate reader. The percent inhibition of a candidate compound [is] *was* calculated using the following equation.

$$\% \text{ inhibition} = 100 \times \left\{1 - \frac{\text{average OD w/compound}}{\text{average OD w/o compound}}\right\}$$

Compounds of the present invention [exhibit] *exhibited* blocking activity in the above assay as follows[.]*:*

| Compound Of Example | % inhibition @ 0.6 μM |
|---|---|
| 9 | 100 |
| 12 | 100 |
| 15 | 100 |
| 16 | 100 |
| 17 | 100 |
| 18 | 100 |
| 26 | 100 |
| 27 | 100 |

-continued

| Compound Of Example | % inhibition @ 0.6 μM |
|---|---|
| 30 | 100 |
| 32 | 100 |
| 34 | 100 |
| 35 | 100 |
| 41 | 100 |
| 45 | 100 |
| 46 | 100 |
| 49 | 100 |
| 50 | 100 |
| 54 | 100 |
| 59 | 100 |
| 60 | 100 |
| 62 | 100 |

The ability of the compounds of this invention to treat arthritis can be demonstrated in a murine collagen-induced arthritis model according to the method of Kakimoto, et al., Cell Immunol 142: 326–337, 1992, in a rat collagen-induced arthritis model according to the method of Knoerzer, et al., Toxicol Pathol 25:13–19, 1997, in a rat adjuvant arthritis model according to the method of Halloran, et al., [Arthitis] *Arthritis* Rheum 39: 810–819, 1996, in a rat streptococcal cell wall-induced arthritis model according to the method of Schimmer, et al., J. Immunol 160: 1466–1477, 1998, or in a SCID-mouse human rheumatoid arthritis model according to the method of Oppenheimer-Marks et al., J Clin. Invest 101: 1261–1272, 1998.

The ability of the compounds of this invention to treat Lyme arthritis can be demonstrated according to the method of Gross et al., Science 281, 703–706, 1998.

The ability of compounds of this invention to treat asthma can be demonstrated in a murine allergic asthma model according to the method of Wegner et al., Science 247:456–459, 1990, or in a murine non-allergic asthma model according to the method of Bloemen et al., Am J Respir Crit Care Med 153:521–529, 1996.

The ability of compounds of this invention to treat inflammatory lung injury can be demonstrated in a murine oxygen-induced lung injury model according to the method of Wegner et al., Lung 170:267–279, 1992, in a murine immune complex-induced lung injury model according to the method of Mulligan et al., J Immunol 154:1350–1363, 1995, or in a murine acid-induced lung injury model according to the method of Nagase, et al., Am J Respir Crit Care Med 154:504–510, 1996.

The ability of compounds of this invention to treat inflammatory bowel disease can be demonstrated in a rabbit chemical-induced colitis model according to the method of Bennet et al., J Pharmacol Exp Ther 280:988–1000, 1997.

The ability of compounds of this invention to treat autoimmune diabetes can be demonstrated in an NOD mouse model according to the method of Hasagawa et al., Int Immunol 6:831–838, 1994, or in a murine streptozotocin-induced diabetes model according to the method of Herrold et al., Cell Immunol 157:489–500, 1994.

The ability of compounds of this invention to treat inflammatory liver injury can be demonstrated in a murine liver injury model according to the method of Tanaka et al., J Immunol 151:5088–5095, 1993.

The ability of compounds of this invention to treat inflammatory glomerular injury can be demonstrated in a rat nephrotoxic serum nephritis model according to the method of Kawasaki, et al., J Immunol 150:1074–1083, 1993.

The ability of compounds of this invention to treat radiation-induced enteritis can be demonstrated in a rat abdominal irradiation model according to the method of Panes et al., Gastroenterology 108:1761–1769, 1995.

The ability of compounds of this invention to treat radiation pneumonitis can be demonstrated in a murine pulmonary irradiation model according to the method of Hallahan et al., Proc Natl Acad Sci USA 94:6432–6437, 1997.

The ability of compounds of this invention to treat reperfusion injury can be demonstrated in the isolated rat heart according to the method of Tamiya et al., Immunopharmacology 29(1): 53–63, 1995, or in the anesthetized dog according to the model of Hartman et al., Cardiovasc Res 30(1): 47–54, 1995.

The ability of compounds of this invention to treat pulmonary reperfusion injury can be demonstrated in a rat lung allograft reperfusion injury model according to the method of DeMeester et al., Transplantation 62(10): 1477–1485, 1996, or in a rabbit pulmonary edema model according to the method of Horgan et al., Am J Physiol 261(5): H1578–H1584, 1991.

The ability of compounds of this invention to treat stroke can be demonstrated in a rabbit cerebral embolism stroke model according the method of Bowes et al., Exp Neurol 119(2): 215–219, 1993, in a rat middle cerebral artery ischemia-reperfusion model according to the method of Chopp et al., Stroke 25(4): 869–875, 1994, or in a rabbit reversible spinal cord ischemia model according to the method of Clark et al., Neurosurg 75(4): 623–627, 1991.

The ability of compounds of this invention to treat peripheral artery occlusion can be demonstrated in a rat skeletal muscle ischemia/reperfusion model according to the method of Gute et al., Mol Cell Biochem 179: 169–187, 1998.

The ability of compounds of this invention to treat graft rejection can be demonstrated in a murine cardiac allograft rejection model according to the method of Isobe et al., Science 255: 1125–1127, 1992, in a murine thyroid gland kidney capsule model according to the method of Talento et al., Transplantation 55: 418–422, 1993, in a cynomolgus monkey renal allograft model according to the method of Cosimi et al., J Immunol 144: 4604–4612, 1990, in a rat nerve allograft model according to the method of Nakao et al., Muscle Nerve 18: 93–102, 1995, in a murine skin allograft model according to the method of Gorczynski and Wojcik, J Immunol 152: 2011–2019, 1994, in a murine corneal allograft model according to the method of He et al., Opthalmol Vis Sci 35: 3218–3225, 1994, or in a xenogeneic pancreatic islet cell transplantation model according to the method of Zeng et al., Transplantation 58:681–689, 1994.

The ability of compounds of this invention to treat graft-vs.-host disease (GVHD) can be demonstrated in a murine lethal GVHD model according to the method of Haming et al., Transplantation 52:842–845, 1991.

The ability of compounds of this invention to treat cancers can be demonstrated in a human lymphoma metastasis model (in mice) according to the method of Aoudjit et al., J Immunol 161:2333–2338, 1998.

What is claimed is:

1. A compound of [the] formula *I:*

I

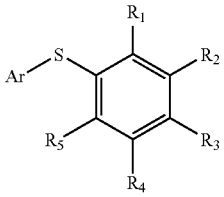

or a pharmaceutically-acceptable salt or *pharmaceutically-acceptable* prodrug [thereof] *of a compound of formula I,* wherein $R_1$, $R_2$, $R_3$, $R_4$, and $R_5$ are independently selected from a. hydrogen, b. halogen, c. alkyl, d. haloalkyl, e. alkoxy, f. cyano, g. nitro, *and* h. carboxaldehyde, 1 [and]

with the proviso that at least one of $R_1$ [or] *and* $R_3$ is a "cis-cinnamide" or a "trans-cinnamide", defined as

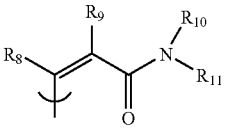

"cis-cinnamide"

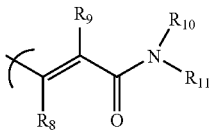

"trans-cinnamide"

wherein $R_8$ and $R_9$ are *each* independently selected from a. hydrogen, and b. alkyl, c. carboxy[ ]alkyl, d. alkylaminocarbonyl[ ]alkyl, and e. dialkylaminocarbonyl[ ]alkyl, and $R_{10}$ and $R_{11}$ are *each* independently selected from a. hydrogen, b. alkyl, c. cycloalkyl, d. alkoxycarbonylalkyl, e. hydroxyalkyl, and f. heterocyclylalkyl, or where [$NR_{10}R_{11}$ is] $R_{10}$ *and* $R_{11}$ *are taken together with the N to form an unsubstituted* heterocyclyl *group,* or *a* substituted heterocyclyl, *where the substituted heterocyclyl group is substituted by one or more than one substituent,* where *the* substituents are *each* independently selected from 1) alkyl, 2) alkoxy, 3) alkoxyalkyl, 4) cycloalkyl, 5) aryl, 6) heterocyclyl, 7) heterocyclylcarbonyl, 8) heterocyclylalkylaminocarbonyl, 9) hydroxy, 10) hydroxyalkyl, 11) hydroxyalkoxyalkyl, 12) carboxy, 13) carboxycarbonyl, 14) carboxaldehyde, 15) alkoxycarbonyl, 16) arylalkoxycarbonyl, 17) aminoalkanoyl, 18) carboxamido, 19) alkoxycarbonylalkyl, 20) carboxamidoalkyl, 21) alkanoyl, 22) hydroxyalkanoyl, 23) alkanoyloxy, 24) alkanoylamino, 25) alkanoyloxyalkyl, and 26) alkylsulfonyl, and wherein Ar is *an unsubstituted aryl group, an unsubstituted heteroaryl group,* a substituted aryl *group,* or *a* substituted heteroaryl group, *where the substituted aryl group and the substituted heteroaryl group are substituted by one or more than one substituent,* where [substitutions] *the substituents* are *each* independently selected from

[a. hydrogen,]

[b] *a.* halogen,

[c] *b.* alkyl,

[d] *c.* aryl,

[e] *d.* haloalkyl,

[f] *e.* hydroxy,

[g] *f.* alkoxy,

[h] *g.* alkoxycarbonyl,

[i] *h.* alkoxyalkoxy,

[j] *i.* hydroxyalkyl,

[k] *j.* aminoalkyl,

[l] *k.* alkyl(alkoxycarbonylalkyl)aminoalkyl,

[m] *l. unsubstituted* heterocyclylalkyl,

[n] *m.* substituted heterocyclylalkyl,

[o] *n.* carboxaldehyde,

[p] *o.* carboxaldehyde hydrazone,

[q] *p.* carboxamide,

[r] *q.* alkoxycarbonyl[ ]alkyl,

[s] *r.* hydroxycarbonylalkyl (carboxyalkyl),

[t] *s.* cyano,

[u] *t.* amino,

[v] *u.* heterocyclylalkylamino, and

[w] *v.* "trans-cinnamide",

[or a pharmaceutically-acceptable salt or prodrug thereof.] *subject to the proviso that when $R_3$ is a "cis-cinnamide" or a "trans-cinnamide," as defined above, one or more than one of the following conditions is fulfilled:*

(*A*) *Ar is an unsubstituted heteroaryl group, a substituted heteroaryl group, or a substituted aryl group wherein when Ar is a pyridyl group, Ar is substituted and Ar is not substituted by only one alkyl group;*

(*B*) *one or more than one of $R_1$, $R_2$, $R_4$, and $R_5$, as defined above, are other than hydrogen; and*

(*C*) *$R_{10}$ and $R_{11}$ are taken together with N to form a substituted or unsubstituted heterocyclyl group, as defined above.*

2. A compound according to claim 1 wherein $R_1$ is a "cis-cinnamide" or a "trans-cinnamide", and $R_3$ is hydrogen.

3. A compound according to claim 1 wherein $R_3$ is a "cis-cinnamide" or a "trans-cinnamide"[, and $R_1$ is hydrogen].

4. A compound according to claim 1 wherein $R_3$ is a "cis-cinnamide" or a "trans-cinnamide", and *one or more than one of* $R_1$, $R_8$, and $R_9$ are *each* hydrogen.

5. A compound according to claim 4 wherein $R_3$ is a "cis-cinnamide".

6. A compound according to claim 4 wherein $R_3$ is a "trans-cinnamide".

7. A compound according to claim 1 wherein $R_3$ is a "cis-cinnamide" or a "trans-cinnamide", and $R_1$, $R_2$, and $R_4$ are each independently hydrogen or alkyl; and $R_5$ is selected from halogen, haloalkyl, and nitro.

8. A compound according to claim 4 wherein Ar is [aryl,] *a* substituted aryl *group*, *an unsubstituted* heteroaryl *group*, or *a* substituted heteroaryl *group*.

9. A compound according to claim 4 wherein *one or both of* $R_{10}$ and $R_{11}$ are each independently selected from hydrogen, alkyl, cycloalkyl, alkoxycarbonylalkyl, hydroxyalkyl, and heterocyclylalkyl.

10. A compound according to claim 4 wherein [$NR_{10}R_{11}$ is] *$R_{10}$ and $R_{11}$ are taken together with N to form an unsubstituted* heterocyclyl *group* or *a* substituted heterocyclyl *group*.

11. A compound according to claim [8] *4* wherein Ar is selected from substituted phenyl, 1,3-benzimidazol-2-one, 1,4-benzodioxane, 1,3-benzodioxole, 1-benzopyr-2-en-4-one, indole, isatin, 1,3-quinazolin-4-one, and quinoline.

12. A compound according to claim 11 wherein $R_3$ is a "trans-cinnamide"[; and Ar is selected from 1,3-benzimidazol-2-one, 1,4-benzodioxane, 1,3-benzodioxole, 1-benzopyr-2-en-4-one, indole, isatin, phenyl, 1,3-quinazolin-4-one, and quinoline].

13. A compound according to claim 12 wherein *one or both of* $R_{10}$ and $R_{11}$ are *each* independently selected from hydrogen, alkyl, cycloalkyl, alkoxycarbonylalkyl, hydroxyalkyl, and heterocyclylalkyl.

14. A compound according to claim 12 wherein [$NR_{10}R_{11}$ is] *$R_{10}$ and $R_{11}$ are taken together with N to form an unsubstituted* heterocyclyl *group* or *a* substituted heterocyclyl [as described above] *group*.

15. A composition comprising a compound [of] *according to* claim 1 [in] *and* a pharmaceutically-acceptable carrier.

16. A method of inhibiting inflammation comprising the administration of a compound of [claim 1] *formula I* to a patient*:*

I

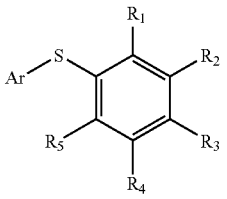

*or a pharmaceutically-acceptable salt or pharmaceutically-acceptable prodrug of a compound of formula I,*

*wherein $R_1$, $R_2$, $R_3$, $R_4$, and $R_5$ are independently selected from*

*a. hydrogen,*

*b. halogen,*

*c. alkyl,*

*d. haloalkyl,*

*e. alkoxy,*

*f. cyano,*

*g. nitro, and*

*h. carboxaldehyde,*

*with the proviso that at least one of $R_1$ and $R_3$ is a "cis-cinnamide" or a "trans-cinnamide", defined as*

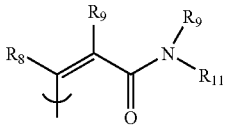

"cis-cinnamide"

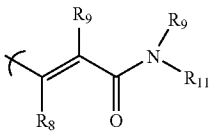

"trans-cinnamide"

*where $R_8$ and $R_9$ are each independently selected from*

*a. hydrogen,*

*b. alkyl,*

*c. carboxyalkyl,*

*d. alkylaminocarbonylalkyl, and*

*e. dialkylaminocarbonylalkyl,*

*$R_{10}$ and $R_{11}$ are each independently selected from*

*a. hydrogen,*

*b. alkyl,*

*c. cycloalkyl,*

*d. alkoxycarbonylalkyl,*

*e. hydroxyalkyl, and*

*f. heterocyclylalkyl,*

*or $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from*

*1) alkyl,*

*2) alkoxy,*

*3) alkoxyalkyl,*

*4) cycloalkyl,*

*5) aryl,*

*6) heterocyclyl,*

*7) heterocyclylcarbonyl,*

*8) heterocyclylalkylaminocarbonyl,*

*9) hydroxy,*

*10) hydroxyalkyl,*

*11) hydroxyalkoxyalkyl,*

*12) carboxy,*

*13) carboxycarbonyl,*

*14) carboxaldehyde,*

*15) alkoxycarbonyl,*

*16) arylalkoxycarbonyl,*

*17) aminoalkanoyl,*

*18) carboxamido,*

*19) alkoxycarbonylalkyl,*

*20) carboxamidoalkyl,*

*21) alkanoyl,*

*22) hydroxyalkanoyl,*

*23) alkanoyloxy,*

*24) alkanoylamino,*

*25) alkanoyloxyalkyl, and*

*26) alkylsulfonyl,*

*and Ar is an unsubstituted aryl group, an unsubstituted heteroaryl group, a substituted aryl group, or a substituted heteroaryl group, where the substituted aryl group and the*

*substituted heteroaryl group are substituted by one or more than one substituent, where the substituents, are each independently selected from*

*a. halogen,*
*b. alkyl,*
*c. aryl,*
*d. haloalkyl,*
*e. hydroxy,*
*f. alkoxy,*
*g. alkoxycarbonyl,*
*h. alkoxyalkoxy,*
*i. hydroxyalkyl,*
*j. aminoalkyl,*
*k. alkyl(alkoxycarbonylalkyl)aminoalkyl,*
*l. unsubstituted heterocyclylalkyl,*
*m. substituted heterocyclylalkyl,*
*n. carboxaldehyde,*
*o. carboxaldehyde hydrazone,*
*p. carboxamide,*
*q. alkoxycarbonylalkyl,*
*r. hydroxycarbonylalkyl(carboxyalkyl),*
*s. cyano,*
*t. amino,*
*u. heterocyclylalkylamino, and*
*v. "trans-cinnamide".*

17. A method of inhibiting inflammation comprising the administration of a composition *comprising a compound* of [claim 15] *formula I* to a patient*:*

I

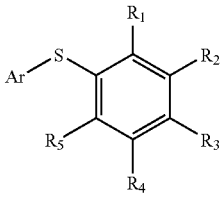

*or a pharmaceutically-acceptable salt or pharmaceutically-acceptable prodrug of a compound of formula I,*

*wherein $R_1$, $R_2$, $R_3$, $R_4$, and $R_5$ are independently selected from*

*a. hydrogen,*
*b. halogen,*
*c. alkyl,*
*d. haloalkyl,*
*e. alkoxy,*
*f. cyano,*
*g. nitro, and*
*h. carboxaldehyde,*

*with the proviso that at least one of $R_1$ and $R_3$ is a "cis-cinnamide" or a "trans-cinnamide", defined as*

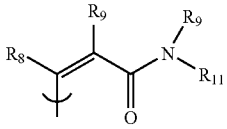

"cis-cinnamide"

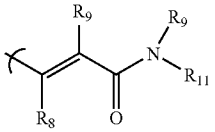

"trans-cinnamide"

*where $R_8$ and $R_9$ are each independently selected from*

*a. hydrogen,*
*b. alkyl,*
*c. carboxyalkyl,*
*d. alkylaminocarbonylalkyl, and*
*e. dialkylaminocarbonylalkyl,*

*$R_{10}$ and $R_{11}$ are each independently selected from*

*a. hydrogen,*
*b. alkyl,*
*c. cycloalkyl,*
*d. alkoxycarbonylalkyl,*
*e. hydroxyalkyl, and*
*f. heterocyclylalkyl,*

*or $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from*

*1) alkyl,*
*2) alkoxy,*
*3) alkoxyalkyl,*
*4) cycloalkyl,*
*5) aryl,*
*6) heterocyclyl,*
*7) heterocyclylcarbonyl,*
*8) heterocyclylalkylaminocarbonyl,*
*9) hydroxy,*
*10) hydroxyalkyl,*
*11) hydroxyalkoxyalkyl,*
*12) carboxy,*
*13) carboxycarbonyl,*
*14) carboxaldehyde,*
*15) alkoxycarbonyl,*
*16) arylalkoxycarbonyl,*
*17) aminoalkanoyl,*
*18) carboxamido,*
*19) alkoxycarbonylalkyl,*
*20) carboxamidoalkyl,*
*21) alkanoyl,*
*22) hydroxyalkanoyl,*
*23) alkanoyloxy,*
*24) alkanoylamino,*
*25) alkanoyloxyalkyl, and*
*26) alkylsulfonyl,*

*and Ar is an unsubstituted aryl group, an unsubstituted heteroaryl group, a substituted aryl group, or a substituted heteroaryl group, where the substituted aryl group and the substituted heteroaryl group are substituted by one or more than one substituent, where the substituents, are each independently selected from*

*a. halogen,*

*b. alkyl,*

*c. aryl,*

*d. haloalkyl,*

*e. hydroxy,*

*f. alkoxy,*

*g. alkoxycarbonyl,*

*h. alkoxyalkoxy,*

*i. hydroxyalkyl,*

*j. aminoalkyl,*

*k. alkyl(alkoxycarbonylalkyl)aminoalkyl,*

*l. unsubstituted heterocyclylalkyl,*

*m. substituted heterocyclylalkyl,*

*n. carboxaldehyde,*

*o. carboxaldehyde hydrazone,*

*p. carboxamide,*

*q. alkoxycarbonylalkyl,*

*r. hydroxycarbonylalkyl(carboxyalkyl),*

*s. cyano,*

*t. amino,*

*u. heterocyclylalkylamino, and*

*v. "trans-cinnamide"*

*and a pharmaceutically-acceptable carrier.*

18. A method of suppressing immune response comprising the administration of a compound of [claim 1] *formula I* to a patient:

I

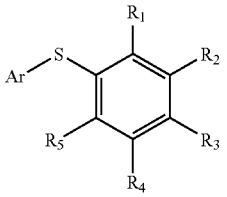

*or a pharmaceutically-acceptable salt or pharmaceutically-acceptable prodrug of a compound of formula I,*

*wherein $R_1$, $R_2$, $R_3$, $R_4$, and $R_5$ are independently selected from*

*a. hydrogen,*

*b. halogen,*

*c. alkyl,*

*d. haloalkyl,*

*e. alkoxy,*

*f. cyano,*

*g. nitro, and*

*h. carboxaldehyde,*

*with the proviso that at least one of $R_1$ and $R_3$ is a "cis-cinnamide" or a "trans-cinnamide", defined as*

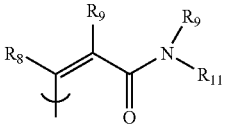

"cis-cinnamide"

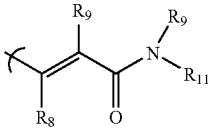

"trans-cinnamide"

*where $R_8$ and $R_9$ are each independently selected from*

*a. hydrogen,*

*b. alkyl,*

*c. carboxyalkyl,*

*d. alkylaminocarbonylalkyl, and*

*e. dialkylaminocarbonylalkyl,*

*$R_{10}$ and $R_{11}$ are each independently selected from*

*a. hydrogen,*

*b. alkyl,*

*c. cycloalkyl,*

*d. alkoxycarbonylalkyl,*

*e. hydroxyalkyl, and*

*f. heterocyclylalkyl,*

*or $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from*

*1) alkyl,*

*2) alkoxy,*

*3) alkoxyalkyl,*

*4) cycloalkyl,*

*5) aryl,*

*6) heterocyclyl,*

*7) heterocyclylcarbonyl,*

*8) heterocyclylalkylaminocarbonyl,*

*9) hydroxy,*

*10) hydroxyalkyl,*

*11) hydroxyalkoxyalkyl,*

*12) carboxy,*

*13) carboxycarbonyl,*

*14) carboxaldehyde,*

*15) alkoxycarbonyl,*

*16) arylalkoxycarbonyl,*

*17) aminoalkanoyl,*

*18) carboxamido,*

*19) alkoxycarbonylalkyl,*

*20) carboxamidoalkyl,*

*21) alkanoyl,*

*22) hydroxyalkanoyl,*

*23) alkanoyloxy,*

*24) alkanoylamino,*

*25) alkanoyloxyalkyl, and*

*26) alkylsulfonyl,*

*and Ar is an unsubstituted aryl group, an unsubstituted heteroaryl group, a substituted aryl group, or a substituted heteroaryl group, where the substituted aryl group and the substituted heteroaryl group are substituted by one or more than one substituent, where the substituents, are each independently selected from*

*a. halogen,*

*b. alkyl,*

*c. aryl,*

*d. haloalkyl,*

*e. hydroxy,*

*f. alkoxy,*

*g. alkoxycarbonyl,*

*h. alkoxyalkoxy,*

*i. hydroxyalkyl,*

*j. aminoalkyl,*

*k. alkyl(alkoxycarbonylalkyl)aminoalkyl,*

*l. unsubstituted heterocyclylalkyl,*

*m. substituted heterocyclylalkyl,*

*n. carboxaldehyde,*

*o. carboxaldehyde hydrazone,*

*p. carboxamide,*

*q. alkoxycarbonylalkyl,*

*r. hydroxycarbonylalkyl(carboxyalkyl),*

*s. cyano,*

*t. amino,*

*u. heterocyclylalkylamino, and*

*v. "trans-cinnamide".*

19. A method of suppressing immune response comprising the administration of a composition *comprising a compound* of [claim 15] *formula I* to a patient:

I

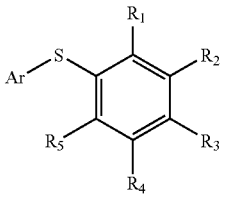

*or a pharmaceutically-acceptable salt or pharmaceutically-acceptable prodrug of a compound of formula I,*

*wherein $R_1$, $R_2$, $R_3$, $R_4$, and $R_5$ are independently selected from*

*a. hydrogen,*

*b. halogen,*

*c. alkyl,*

*d. haloalkyl,*

*e. alkoxy,*

*f. cyano,*

*g. nitro, and*

*h. carboxaldehyde,*

*with the proviso that at least one of $R_1$ and $R_3$ is a "cis-cinnamide" or a "trans-cinnamide", defined as*

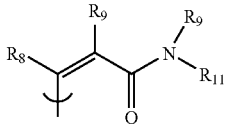

"cis-cinnamide"

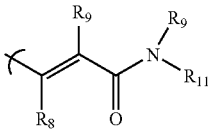

"trans-cinnamide"

*where $R_8$ and $R_9$ are each independently selected from*

*a. hydrogen,*

*b. alkyl,*

*c. carboxyalkyl,*

*d. alkylaminocarbonylalkyl, and*

*e. dialkylaminocarbonylalkyl,*

*$R_{10}$ and $R_{11}$ are each independently selected from*

*a. hydrogen,*

*b. alkyl,*

*c. cycloalkyl,*

*d. alkoxycarbonylalkyl,*

*e. hydroxyalkyl, and*

*f. heterocyclylalkyl,*

*or $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from*

*1) alkyl,*

*2) alkoxy,*

*3) alkoxyalkyl,*

*4) cycloalkyl,*

*5) aryl,*

*6) heterocyclyl,*

*7) heterocyclylcarbonyl,*

*8) heterocyclylalkylaminocarbonyl,*

*9) hydroxy,*

*10) hydroxyalkyl,*

*11) hydroxyalkoxyalkyl,*

*12) carboxy,*

*13) carboxycarbonyl,*

*14) carboxaldehyde,*

*15) alkoxycarbonyl,*

*16) arylalkoxycarbonyl,*

*17) aminoalkanoyl,*

*18) carboxamido,*

*19) alkoxycarbonylalkyl,*

*20) carboxamidoalkyl,*

*21) alkanoyl,*

*22) hydroxyalkanoyl,*

*23) alkanoyloxy,*

*24) alkanoylamino,*

*25) alkanoyloxyalkyl, and*

*26) alkylsulfonyl,*

*and Ar is an unsubstituted aryl group, an unsubstituted heteroaryl group, a substituted aryl group, or a substituted heteroaryl group, where the substituted aryl group and the substituted heteroaryl group are substituted by one or more than one substituent, where the substituents, are each independently selected from*

*a. halogen,*

*b. alkyl,*

*c. aryl,*

*d. haloalkyl,*

*e. hydroxy,*

*f. alkoxy,*

*g. alkoxycarbonyl,*

*h. alkoxyalkoxy,*

*i. hydroxyalkyl,*

*j. aminoalkyl,*

*k. alkyl(alkoxycarbonylalkyl)aminoalkyl,*

*l. unsubstituted heterocyclylalkyl,*

*m. substituted heterocyclylalkyl,*

*n. carboxaldehyde,*

*o. carboxaldehyde hydrazone,*

*p. carboxamide,*

*q. alkoxycarbonylalkyl,*

*r. hydroxycarbonylalkyl(carboxyalkyl),*

*s. cyano,* t. amino, u. heterocyclylalkylamino, and v. "trans-cinnamide"

and a pharmaceutically-acceptable carrier.

20. A compound according to claim 1 selected from:

(2,4-Dichlorophenyl)[2-(E-((6-hydroxyhexylamino)carbonyl)ethenyl)phenyl]sulfide;

(2,4-Dichlorophenyl)[2-(E-((3-(1-imidazolyl)propylamino)carbonyl)ethenyl)phenyl]sulfide;

(2,4-Dichlorophenyl)[2-chloro-4-(E-((2-hydroxyethylamino)carbonyl)ethenyl)phenyl]sulfide;

(2,4-Dichlorophenyl)[2-chloro-4-(E-((6-hydroxyhexylamino)carbonyl)ethenyl)phenyl]sulfide;

(2,4-Dichlorophenyl)[2-chloro-4-(E-((bis-(2-hydroxyethyl)ainino)carbonyl)ethenyl)phenyl]sulfide;

(2,4-Dichlorophenyl)[2-chloro-4-(E-((3-(2-oxopyrrolidin-1-yl)propylamino)carbonyl)ethenyl)phenyl]sulfide;

(2,4-Dichlorophenyl)[2-chloro-4-(E-((1-morpholinyl)carbonyl)ethenyl)phenyl]sulfide;

(2,4-Dichlorophenyl)[2-chloro-4-(E-((4-methylpiperazin-1-yl)carbonyl)ethenyl)phenyl]sulfide;

(2,4-Dichlorophenyl)[2-chloro-4-(E-((4-acetylpiperazin-1-yl)carbonyl)ethenyl)phenyl]sulfide;

(2,4-Dichlorophenyl)[2-chloro-4-(E-((4-(2-pyridyl)piperazin-1-yl)carbonyl)ethenyl)phenyl]sulfide;

(2-(Hydroxymethyl)phenyl) (2-chloro-4-(E-((1-morpholinyl)carbonyl)ethenyl)phenyl]sulfide;

(2-Bromophenyl)[2-chloro-4-(E-((1-morpholinyl)carbonyl)ethenyl)phenyl]sulfide;

(2,4-Dichlorophenyl)[2-chloro-4-(E-((4-(2-hydroxyethyl)piperazin-1-yl)carbonyl)ethenyl)phenyl]sulfide;

(2,4-Dichlorophenyl)[2-chloro-4-(E-((4-(2-hydroxyethoxyethyl)piperazin-1-yl)carbonyl)ethenyl)phenyl]sulfide;

(2-Bromophenyl)[2-chloro-4-(E-((3-(hydroxymethyl)piperidin-1-yl)carbonyl)ethenyl)phenyl]sulfide;

(2-Bromophenyl)[2-chloro-4-(E-((2-(hydroxymethyl)piperidin-1-yl)carbonyl)ethenyl)phenyl]sulfide;

(2-Bromophenyl)[2-chloro-4-(E-((3-acetamidopyrrolidin-1-yl)carbonyl)ethenyl)phenyl]sulfide;

(2-Bromophenyl)[2-chloro-4-(E-((4-(hydroxypiperidin-1-yl)carbonyl)ethenyl)phenyl]sulfide;

(2-Bromophenyl)[2-chloro-4-(E-((piperidin-1-yl)carbonyl)ethenyl)phenyl]sulfide;

(2,4-Dichlorophenyl)[2-chloro-4-(E-((3-carboxypiperidin-1-yl)carbonyl)ethenyl)phenyl]sulfide;

(2,4-Dichlorophenyl)[2-chloro-4-(E-((4-carboxypiperidin-1-yl)carbonyl)ethenyl)phenyl]sulfide;

(2-Bromophenyl)[2-chloro-4-(E-((4-acetylhomopiperazin-1-yl)carbonyl)ethenyl)phenyl]sulfide;

(2-Bromophenyl)[2-chloro-4-(E-((thiomorpholin-1-yl)carbonyl)ethenyl)phenyl]sulfide;

(2-Bromophenyl)[2-chloro-4-(E-((4-(2-oxo,-2,3-dihydro-1H-benzimidazol-1-yl)piperidin-1-yl)carbonyl)ethenyl)phenyl]sulfide;

(2-Bromophenyl)[2-chloro-4-(E-((2-tetrahydroisoquinolinyl)carbonyl)ethenyl)phenyl]sulfide;

(2-Methylphenyl)[2-trifluoromethyl-4-(E-((4-acetylpiperazin-1-yl)carbonyl)ethenyl)phenyl]sulfide;

(2-Methylphenyl)[2-trifluoromethyl-4-(E-((1-morpholinyl)carbonyl)ethenyl)phenyl]sulfide;

(2-Methylphenyl)[2-trifluoromethyl-4-(E-((2-(1-morpholinyl)ethylamino)carbonyl)ethenyl)phenyl]sulfide;

(2-Methylphenyl)[2-trifluoromethyl-4-(E-((4-phenylpiperazin-1-yl)carbonyl)ethenyl)phenyl]sulfide;

(2-Methylphenyl)[2-trifluoromethyl-4-(E-((3-(2-oxopyrrolidin-1-yl)propylamino)carbonyl)ethenyl)phenyl]sulfide;

(2-Methylphenyl)[2-trifluoromethyl-4-(E-((cyclopropylamino)carbonyl)ethenyl)phenyl]sulfide;

(2,4-Dichlorophenyl)[2-nitro-4-(E-((4-acetylpiperazin-1-yl)carbonyl)ethenyl)phenyl]sulfide;

(2,4-Dichlorophenyl)2-nitro-4-(E-((3-(2-oxopyrrolidin-1-yl)propylamino)carbonyl)ethenyl)phenyl]sulfide;

(2,3-Dichlorophenyl)[2-nitro-4-(E-((4-acetylpiperazin-1-yl)carbonyl)ethenyl)phenyl]sulfide;

(4-Bromophenyl)[2-nitro-4-(E-((4-acetylpiperazin-1-yl)carbonyl)ethenyl)phenyl]sulfide;

(4-Methylphenyl)[2-nitro-4-(E-((4-acetylpiperazin-1-yl)carbonyl)ethenyl)phenyl]sulfide;

(2,4-Dichlorophenyl)[2-nitro-4-(E-((4-(tert-butoxycarbonyl)piperazin-1-yl)carbonyl)ethenyl)phenyl]sulfide;

(2,4-Dichlorophenyl)[2-nitro-4-(E-((4-(2-furoylcarbonyl)piperazin-1-yl)carbonyl)ethenyl)phenyl]sulfide;

(2,4-Dichlorophenyl)[2-nitro-4-(E-((4-(methanesulfonyl)piperazin-1-yl)carbonyl)ethenyl)phenyl]sulfide;

(2,4-Dichlorophenyl)[2-nitro-4-(E-((4-(diethylaminocarbonylmethyl)piperazin-1-yl)carbonyl)ethenyl)phenyl]sulfide;

(2,4-Dichlorophenyl)[2-nitro-4-(E-((4-(diethylaminocarbonyl)piperazin-1-yl)carbonyl)ethenyl)phenyl]sulfide;

(2,4-Dichlorophenyl) (2-nitro-4-(E-((4-(carboxycarbonyl)piperazin-1-yl)carbonyl)ethenyl)phenyl]sulfide;

(2,4-Dichlorophenyl)[2-nitro-4-(E-((4-(carboxymethyl)piperazin-1-yl)carbonyl)ethenyl)phenyl]sulfide;

(2-Methylphenyl)[2-nitro-4-(E-((4-acetylpiperazin-1-yl)carbonyl)ethenyl)phenyl]sulfide;

(2-Chlorophenyl)[2-nitro-4-(E-((4-acetylpiperazin-1-yl)carbonyl)ethenyl)phenyl]sulfide;

(2-Aminophenyl)[2-nitro-4-(E-((4-acetylpiperazin-1-yl)carbonyl)ethenyl)phenyl]sulfide;

(2-Hydroxymethylphenyl)[2-nitro-4-(E-((4-acetylpiperazin-1-yl)carbonyl)ethenyl)phenyl]sulfide;

(2-Ethylphenyl)[2-nitro-4-(E-((4-acetylpiperazin-1-yl)carbonyl)ethenyl)phenyl]sulfide;

(2-iso-Propylphenyl)[2-nitro-4-(E-((4-acetylpiperazin-1-yl)carbonyl)ethenyl)phenyl]sulfide;

(2-tert-Butylphenyl)[2-nitro-4-(E-((4-acetylpiperazin-1-yl)carbonyl)ethenyl)phenyl]sulfide;

(2-Chlorophenyl)[2-chloro-4-(E-((4-acetylpiperain-1-yl)carbonyl))2-propenyl)phenyl]sulfide;

(2-(1-Morpholinylmethyl)phenyl)[2-chloro-4-(E-((1-morpholinyl)carbonyl)ethenyl)phenyl]sulfide;

(2-(4-(1,3-Benzodioxolyl-5-methyl)piperazin-1-ylmethyl)phenyl)[2-chloro-4-(E-((1-morpholinyl)carbonyl)ethenyl)phenyl]sulfide;

(2-(4-(iso-Propylaminocarbonylmethyl)piperazin-1-ylmethyl)phenyl)[2-chloro-4-(E-((1-morpholinyl)carbonyl)ethenyl)phenyl]sulfide;

(2-((N-Ethoxycarbonylmethyl-N-methyl)aminomethyl)phenyl)[2-chloro-4-(E-((1-morpholinyl)carbonyl)ethenyl)phenyl]sulfide;

(2-Formylphenyl)[2-chloro-4-(E-((1-morpholinyl)carbonyl)ethenyl)phenyl]sulfide;

(2-(4-Formylpiperazin-1-ylmethyl)phenyl)[2-chloro-4-(E-((1-morpholinyl)carbonyl)ethenyl)phenyl]sulfide;

(2-(E-((1-Morpholinyl)carbonyl)ethenyl)phenyl)[2-chloro-4-(E-((1-morpholinyl)carbonyl)ethenyl)phenyl]sulfide;

(2-Formylphenyl)[2-nitro-4-(E-((4-acetylpiperazin-1-yl)carbonyl)ethenyl)phenyl]sulfide;

(2-Formylphenyl)[2-chloro-4-(E-((1-morpholinyl)carbonyl)ethenyl)phenyl]sulfide, N,N-dimethyl hydrazone;

(2-((3-(1-Morpholinyl)propyl)-1-amino)phenyl)[2-chloro-4-(E-((1-morpholinyl)carbonyl)ethenyl)phenyl]sulfide;

(2,4-Dichlorophenyl)[2-bromo-4-(E-((3-(2-oxopyrrolidin-1-yl)propylamino)carbonyl)ethenyl)phenyl]sulfide;

(2,4-Dichlorophenyl)[2-formyl-4-(E-((1-morpholinyl)carbonyl)ethenyl)phenyl]sulfide; and (2-Chloro-6-formylphenyl)[2-chloro-4-(E-((4-acetylpiperazin-1-yl)carbonyl)ethenyl)phenyl]sulfide.

21. A compound of formula I:

I

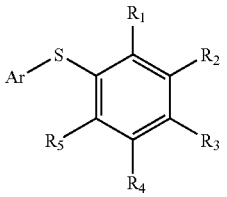

or a pharmaceutically-acceptable salt or pharmaceutically-acceptable prodrug of a compound of formula I, wherein $R_1$, $R_2$, $R_3$, $R_4$, and $R_5$ are independently selected from a. hydrogen, b. halogen, c. alkyl, d. haloalkyl, e. alkoxy, f. cyano, g. nitro, and h. carboxaldehyde, with the proviso that at least one of $R_1$ and $R_3$ is a "cis-cinnamide" or a "trans-cinnamide", defined as

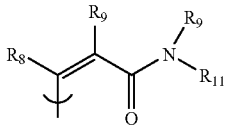

"cis-cinnamide"

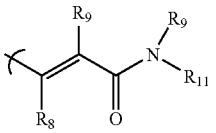

"trans-cinnamide"

where $R_8$ and $R_9$ are each independently selected from a. hydrogen, b. alkyl, c. carboxyalkyl, d. alkylaminocarbonylalkyl, and e. dialkylaminocarbonylalkyl, $R_{10}$ and $R_{11}$ are each independently selected from a. hydrogen, b. alkyl, c. cycloalkyl, d. alkoxycarbonylalkyl, e. hydroxyalkyl, and f. heterocyclylalkyl, or $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from 1) alkyl, 2) alkoxy, 3) alkoxyalkyl, 4) cycloalkyl, 5) aryl, 6) heterocyclyl, 7) heterocyclylcarbonyl, 8) heterocyclylalkylaminocarbonyl, 9) hydroxy, 10) hydroxyalkyl, 11) hydroxyalkoxyalkyl, 12) carboxy, 13) carboxycarbonyl, 14) carboxaldehyde, 15) alkoxycarbonyl, 16) arylalkoxycarbonyl, 17) aminoalkanoyl, 18) carboxamido, 19) alkoxycarbonylalkyl, 20) carboxamidoalkyl, 21) alkanoyl, 22) hydroxyalkanoyl, 23) alkanoyloxy, 24) alkanoylamino, 25) alkanoyloxyalkyl, and 26) alkylsulfonyl, and Ar is an unsubstituted aryl group, an unsubstituted heteroaryl group, a substituted aryl group, or a substituted heteroaryl group, where the substituted aryl group and the substituted heteroaryl group are substituted by one or more than one substituent, where the substituents are each independently selected from a. halogen, b. alkyl, c. aryl, d. haloalkyl, e. hydroxy, f. alkoxy, g. alkoxycarbonyl, h. alkoxyalkoxy, i. hydroxyalkyl, j. aminoalkyl, k. alkyl(alkoxycarbonylalkyl)aminoalkyl, l. unsubstituted heterocyclylalkyl, m. substituted heterocyclylalkyl, n. carboxaldehyde, o. carboxaldehyde hydrazone, p. carboxamide, q. alkoxycarbonylalkyl, r. hydroxycarbonylalkyl(carboxyalkyl), s. cyano, t. amino, u. heterocyclylalkylamino, and v. "trans-cinnamide", subject to the proviso that when $R_3$ is a "cis-cinnamide" or a "trans-cinnamide," as defined above, one or more than one of the following conditions is fulfilled:

(A) $R_1$, as defined above, is other than hydrogen;

(B) $R_8$ and $R_9$ are both hydrogen and Ar is not pyridyl; and (C) $R_{10}$ and $R_{11}$ are taken together with N to form a substituted or unsubstituted heterocyclyl group, as defined above.

22. *A compound of formula I:*

I

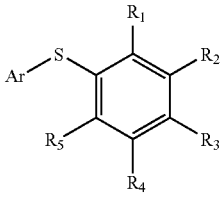

*or a pharmaceutically-acceptable salt or pharmaceutically-acceptable prodrug of a compound of formula I,*

*wherein $R_1$, $R_2$, $R_3$, $R_4$, and $R_5$ are independently selected from*

*a. hydrogen,*

*b. halogen,*

*c. alkyl,*

*d. haloalkyl,*

*e. alkoxy,*

*f. cyano,*

*g. nitro, and*

*h. carboxaldehyde,*

*with the proviso that at least one of $R_1$ and $R_3$ is a "cis-cinnamide" or a "trans-cinnamide", defined as*

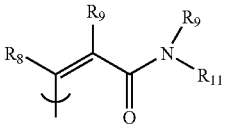

"cis-cinnamide"

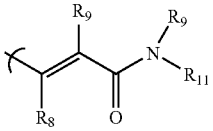

"trans-cinnamide"

*where $R_8$ and $R_9$ are each independently selected from*

*a. hydrogen,*

*b. alkyl,*

*c. carboxyalkyl,*

*d. alkylaminocarbonylalkyl, and*

*e. dialkylaminocarbonylalkyl,*

*$R_{10}$ and $R_{11}$ are each independently selected from*

*a. hydrogen,*

*b. alkyl,*

*c. cycloalkyl,*

*d. alkoxycarbonylalkyl,*

*e. hydroxyalkyl, and*

*f. heterocyclylalkyl,*

*or $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from*

*1) alkyl,*

*2) alkoxy,*

*3) alkoxyalkyl,*

*4) cycloalkyl,*

*5) aryl,*

*6) heterocyclyl,*

*7) heterocyclylcarbonyl,*

*8) heterocyclylalkylaminocarbonyl,*

*9) hydroxy,*

*10) hydroxyalkyl,*

*11) hydroxyalkoxyalkyl,*

*12) carboxy,*

*13) carboxycarbonyl,*

*14) carboxaldehyde,*

*15) alkoxycarbonyl,*

*16) arylalkoxycarbonyl,*

*17) aminoalkanoyl,*

*18) carboxamido,*

*19) alkoxycarbonylalkyl,*

*20) carboxamidoalkyl,*

*21) alkanoyl,*

*22) hydroxyalkanoyl,*

*23) alkanoyloxy,*

*24) alkanoylamino,*

*25) alkanoyloxyalkyl, and*

*26) alkylsulfonyl,*

*and Ar is an unsubstituted aryl group, an unsubstituted heteroaryl group, a substituted aryl group, or a substituted heteroaryl group, where the substituted aryl group and the substituted heteroaryl group are substituted by one or more than one substituent, where the substituents are each independently selected from*

*a. halogen,*

*b. alkyl,*

*c. aryl,*

*d. haloalkyl,*

*e. hydroxy,*

*f. alkoxy,*

*g. alkoxycarbonyl,*

*h. alkoxyalkoxy,*

*i. hydroxyalkyl,*

*j. aminoalkyl,*

*k. alkyl(alkoxycarbonylalkyl)aminoalkyl,*

*l. unsubstituted heterocyclylalkyl,*

*m. substituted heterocyclylalkyl,*

*n. carboxaldehyde,*

*o. carboxaldehyde hydrazone,*

*p. carboxamide,*

*q. alkoxycarbonylalkyl,*

*r. hydroxycarbonylalkyl(carboxyalkyl),*

*s. cyano,*

*t. amino,*

*u. heterocyclylalkylamino, and*

*v. "trans-cinnamide",*

*subject to the proviso that one or more than one of the following conditions is fulfilled:*

*(A) Ar is an unsubstituted heteroaryl group, a substituted heteroaryl group, or a substituted aryl group;*

*(B) two or more than two of $R_1$, $R_2$, $R_3$, $R_4$, and $R_5$, as defined above, are other than hydrogen; and*

*(C) $R_{10}$ and $R_{11}$ are taken together with N to form a substituted or unsubstituted heterocyclyl group, as defined above.*

23. A compound of formula I:

I

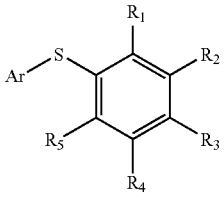

or a pharmaceutically-acceptable salt or pharmaceutically-acceptable prodrug of a compound of formula I, wherein $R_1$, $R_2$, $R_4$, and $R_5$ are independently selected from a. hydrogen,
b. halogen,
c. alkyl,
d. haloalkyl,
e. alkoxy,
f. cyano,
g. nitro, and
h. carboxaldehyde, where $R_3$ is a "cis-cinnamide" or "trans-cinnamide", defined as

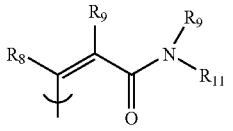

"cis-cinnamide"

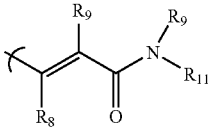

"trans-cinnamide"

where $R_8$ and $R_9$ are each independently selected from a. hydrogen,
b. alkyl,
c. carboxyalkyl,
d. alkylaminocarbonylalkyl, and
e. dialkylaminocarbonylalkyl, $R_{10}$ and $R_{11}$ are each independently selected from a. hydrogen,
b. alkyl,
c. cycloalkyl,
d. alkoxycarbonylalkyl,
e. hydroxyalkyl, and
f. heterocyclylalkyl, or $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from 1) alkyl,
2) alkoxy,
3) alkoxyalkyl,
4) cycloalkyl,
5) aryl,
6) heterocyclyl,
7) heterocyclylcarbonyl,
8) heterocyclylalkylaminocarbonyl,
9) hydroxy,
10) hydroxyalkyl,
11) hydroxyalkoxyalkyl,
12) carboxy,
13) carboxycarbonyl,
14) carboxaldehyde,
15) alkoxycarbonyl,
16) arylalkoxycarbonyl,
17) aminoalkanoyl,
18) carboxamido,
19) alkoxycarbonylalkyl,
20) carboxamidoalkyl,
21) alkanoyl,
22) hydroxyalkanoyl,
23) alkanoyloxy,
24) alkanoylamino,
25) alkanoyloxyalkyl, and
26) alkylsulfonyl, and Ar is an unsubstituted heteroaryl group, a substituted aryl group, or a substituted heteroaryl group, where the substituted aryl group and the substituted heteroaryl group are substituted by one or more than one substituent, where the substituents are each independently selected from a. halogen,
b. alkyl,
c. aryl,
d. haloalkyl,
e. hydroxy,
f. alkoxy,
g. alkoxycarbonyl,
h. alkoxyalkoxy,
i. hydroxyalkyl,
j. aminoalkyl,
k. alkyl(alkoxycarbonylalkyl)aminoalkyl,
l. unsubstituted heterocyclylalkyl,
m. substituted heterocyclylalkyl,
n. carboxaldehyde,
o. carboxaldehyde hydrazone,
p. carboxamide,
q. alkoxycarbonylalkyl,
r. hydroxycarbonylalkyl(carboxyalkyl),
s. cyano,
t. amino,
u. heterocyclylalkylamino, and
v. "trans-cinnamide", wherein when Ar is pyridyl, Ar is substituted by two or more than two substituents.

24. A compound according to claim 23 where one or more than one of $R_1$, $R_2$, $R_4$, and $R_5$ are other than hydrogen.

25. A compound according to claim 23 where $R_{10}$ and $R_{11}$ are taken together with N to form a substituted or unsubstituted heterocyclyl group.

26. A compound of formula I:

I

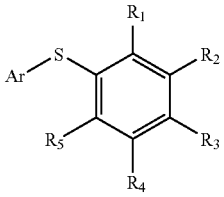

or a pharmaceutically-acceptable salt or pharmaceutically-acceptable prodrug of a compound of formula I, wherein $R_1$, $R_2$, $R_4$, and $R_5$ are independently selected from a. hydrogen, b. halogen, c. alkyl, d. haloalkyl, e. alkoxy, f. cyano, g. nitro, and h. carboxaldehyde, subject to the proviso that one or more than one of $R_1$, $R_2$, $R_4$, and $R_5$ are other than hydrogen, where $R_3$ is a "cis-cinnamide" or "trans-cinnamide", defined as

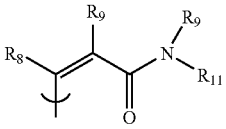

"cis-cinnamide"

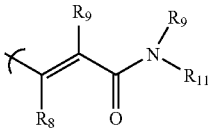

"trans-cinnamide"

where $R_8$ and $R_9$ are each independently selected from a. hydrogen, b. alkyl, c. carboxyalkyl, d. alkylaminocarbonylalkyl, and e. dialkylaminocarbonylalkyl, $R_{10}$ and $R_{11}$ are each independently selected from a. hydrogen, b. alkyl, c. cycloalkyl, d. alkoxycarbonylalkyl, e. hydroxyalkyl, and f. heterocyclylalkyl, or $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from 1) alkyl, 2) alkoxy, 3) alkoxyalkyl, 4) cycloalkyl, 5) aryl, 6) heterocyclyl, 7) heterocyclylcarbonyl, 8) heterocyclylalkylaminocarbonyl, 9) hydroxy, 10) hydroxyalkyl, 11) hydroxyalkoxyalkyl, 12) carboxy, 13) carboxycarbonyl, 14) carboxaldehyde, 15) alkoxycarbonyl, 16) arylalkoxycarbonyl, 17) aminoalkanoyl, 18) carboxamido, 19) alkoxycarbonylalkyl, 20) carboxamidoalkyl, 21) alkanoyl, 22) hydroxyalkanoyl, 23) alkanoyloxy, 24) alkanoylamino, 25) alkanoyloxyalkyl, and 26) alkylsulfonyl, and Ar is an unsubstituted aryl group, an unsubstituted heteroaryl group, a substituted aryl group, or a substituted heteroaryl group, where the substituted aryl group and the substituted heteroaryl group are substituted by one or more than one substituent, where the substituents are each independently selected from a. halogen, b. alkyl, c. aryl, d. haloalkyl, e. hydroxy, f. alkoxy, g. alkoxycarbonyl, h. alkoxyalkoxy, i. hydroxyalkyl, j. aminoalkyl, k. alkyl(alkoxycarbonylalkyl)aminoalkyl, l. unsubstituted heterocyclylalkyl, m. substituted heterocyclylalkyl, n. carboxaldehyde, o. carboxaldehyde hydrazone, p. carboxamide, q. alkoxycarbonylalkyl, r. hydroxycarbonylalkyl(carboxyalkyl), s. cyano, t. amino, u. heterocyclylalkylamino, and v. "trans-cinnamide".

27. A compound according to claim 26 where $R_{10}$ and $R_{11}$ are taken together with N to form a substituted heterocyclyl group or an unsubstituted heterocyclyl group.

28. A compound of formula I:

I

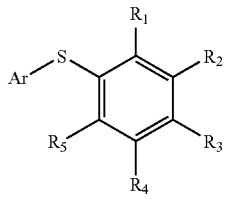

or a pharmaceutically-acceptable salt or pharmaceutically-acceptable prodrug of a compound of formula I, wherein $R_1$, $R_2$, $R_4$, and $R_5$ are each independently selected from a. hydrogen,
b. halogen,
c. alkyl,
d. haloalkyl,
e. alkoxy,
f. cyano,
g. nitro, and
h. carboxaldehyde, where $R_3$ is a "cis-cinnamide" or "trans-cinnamide", defined as

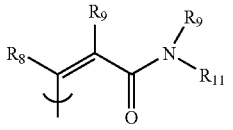

"cis-cinnamide"

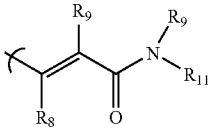

"trans-cinnamide"

where $R_8$ and $R_9$ are each independently selected from a. hydrogen,
b. alkyl,
c. carboxyalkyl,
d. alkylaminocarbonylalkyl, and
e. dialkylaminocarbonylalkyl, $R_{10}$ and $R_{11}$ are taken together with the N to form an unsubstituted heterocyclyl group, or a substituted heterocyclyl group, where the substituted heterocyclyl group is substituted by one or more than one substituent, where the substituents are each independently selected from 1) alkyl,
2) alkoxy,
3) alkoxyalkyl,
4) cycloalkyl,
5) aryl,
6) heterocyclyl,
7) heterocyclylcarbonyl,
8) heterocyclylalkylaminocarbonyl,
9) hydroxy,
10) hydroxyalkyl,
11) hydroxyalkoxyalkyl,
12) carboxy,
13) carboxycarbonyl,
14) carboxaldehyde,
15) alkoxycarbonyl,
16) arylalkoxycarbonyl,
17) aminoalkanoyl,
18) carboxamido,
19) alkoxycarbonylalkyl,
20) carboxamidoalkyl,
21) alkanoyl,
22) hydroxyalkanoyl,
23) alkanoyloxy,
24) alkanoylamino,
25) alkanoyloxyalkyl, and
26) alkylsulfonyl, and Ar is an unsubstituted aryl group, an unsubstituted heteroaryl group, a substituted aryl group, or a substituted heteroaryl group, where the substituted aryl group and the substituted heteroaryl group are substituted by one or more than one substituent, where the substituents are each independently selected from a. halogen,
b. alkyl,
c. aryl,
d. haloalkyl,
e. hydroxy,
f. alkoxy,
g. alkoxycarbonyl,
h. alkoxyalkoxy,
i. hydroxyalkyl,
j. aminoalkyl,
k. alkyl(alkoxycarbonylalkyl)aminoalkyl,
l. unsubstituted heterocyclylalkyl,
m. substituted heterocyclylalkyl,
n. carboxaldehyde,
o. carboxaldehyde hydrazone,
p. carboxamide,
q. alkoxycarbonylalkyl,
r. hydroxycarbonylalkyl(carboxyalkyl),
s. cyano,
t. amino,
u. heterocyclylalkylamino, and
v. "trans-cinnamide".

29. A compound according to claim 1 wherein Ar is an unsubstituted heteroaryl group or a substituted heteroaryl group and wherein the heteroaryl group is selected from benzimidazolyl, benzofuryl, benzothiazolyl, benzothienyl, benzoxazolyl, cinnolinyl, dihydroindolyl, furyl, imidazolyl, indolyl, isoquinolyl, isothiazolyl, isoxazolyl, oxadiazolyl, oxazolyl, pyrazinyl, pyrazolyl, pyridazinyl, pyrimidinyl, pyrimidyl, pyrrolyl, quinolinyl, tetrahydroisoquinolyl, tetrahydroquinolyl, tetrazolyl, thiadiazolyl, thiazolyl, thienyl, and compounds of the formula:

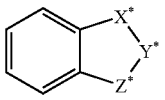

wherein X* and Z* are independently selected from —$CH_2$—, —$CH_2NH$—, —$CH_2O$—, —NH—, and —O— with the proviso that at least one of X* and Z* is not —$CH_2$—, and Y* is selected from —C(O)— and —$(C(R'')_2)_v$— where R' is hydrogen or $C_{1-4}$ alkyl and v is 1–3.

30. A compound according to claim 21, wherein Ar is an unsubstituted heteroaryl group or a substituted heteroaryl

*group and wherein the heteroaryl group is selected from benzimidazolyl, benzofuryl, benzothiazolyl, benzothienyl, benzoxazolyl, cinnolinyl, dihydroindolyl, furyl, imidazolyl, indolyl, isoquinolyl, isothiazolyl, isoxazolyl, oxadiazolyl, oxazolyl, pyrazinyl, pyrazolyl, pyridazinyl, pyrimidinyl, pyrimidyl, pyrrolyl, quinolinyl, tetrahydroisoquinolyl, tetrahydroquinolyl, tetrazolyl, thiadiazolyl, thiazolyl, thienyl, and compounds of the formula:*

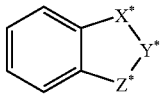

*wherein X* and Z* are independently selected from —$CH_2$—, —$CH_2NH$—, —$CH_2O$—, —NH—, and —O— with the proviso that at least one of X* and Z* is not —$CH_2$—, and Y* is selected from —C(O)— and —$(C(R'')_2)_v$— where R' is hydrogen or $C_{1-4}$ alkyl and v is 1–3.*

*31. A compound according to claim 22 wherein Ar is an unsubstituted heteroaryl group or a substituted heteroaryl group and wherein the heteroaryl group is selected from benzimidazolyl, benzofuryl, benzothiazolyl, benzothienyl, benzoxazolyl, cinnolinyl, dihydroindolyl, furyl, imidazolyl, indolyl, isoquinolyl, isothiazolyl, isoxazolyl, oxadiazolyl, oxazolyl, pyrazinyl, pyrazolyl, pyridazinyl, pyrimidinyl, pyrimidyl, pyrrolyl, quinolinyl, tetrahydroisoquinolyl, tetrahydroquinolyl, tetrazolyl, thiadiazolyl, thiazolyl, thienyl, and compounds of the formula:*

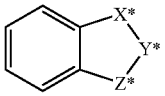

*wherein X* and Z* are independently selected from —$CH_2$—, —$CH_2NH$—, —$CH_2O$—, —NH—, and —O— with the proviso that at least one of X* and Z* is not —$CH_2$—, and Y* is selected from —C(O)— and —$(C(R'')_2)_v$— where R' is hydrogen or $C_{1-4}$ alkyl and v is 1–3.*

*32. A compound according to claim 23 wherein Ar is an unsubstituted heteroaryl group or a substituted heteroaryl group and wherein the heteroaryl group is selected from benzimidazolyl, benzofuryl, benzothiazolyl, benzothienyl, benzoxazolyl, cinnolinyl, dihydroindolyl, furyl, imidazolyl, indolyl, isoquinolyl, isothiazolyl, isoxazolyl, oxadiazolyl, oxazolyl, pyrazinyl, pyrazolyl, pyridazinyl, pyrimidinyl, pyrimidyl, pyrrolyl, quinolinyl, tetrahydroisoquinolyl, tetrahydroquinolyl, tetrazolyl, thiadiazolyl, thiazolyl, thienyl, and compounds of the formula:*

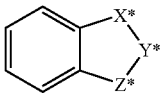

*wherein X* and Z* are independently selected from —$CH_2$—, —$CH_2NH$—, —$CH_2O$—, —NH—, and —O— with the proviso that at least one of X* and Z* is not —$CH_2$—, and Y* is selected from —C(O)— and —$(C(R'')_2)_v$— where R' is hydrogen or $C_{1-4}$ alkyl and v is 1–3.*

*33. A compound according to claim 26 wherein Ar is an unsubstituted heteroaryl group or a substituted heteroaryl group and wherein the heteroaryl group is selected from benzimidazolyl, benzofuryl, benzothiazolyl, benzothienyl, benzoxazolyl, cinnolinyl, dihydroindolyl, furyl, imidazolyl, indolyl, isoquinolyl, isothiazolyl, isoxazolyl, oxadiazolyl, oxazolyl, pyrazinyl, pyrazolyl, pyridazinyl, pyrimidinyl, pyrimidyl, pyrrolyl, quinolinyl, tetrahydroisoquinolyl, tetrahydroquinolyl, tetrazolyl, thiadiazolyl, thiazolyl, thienyl, and compounds of the formula:*

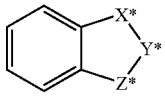

*wherein X* and Z* are independently selected from —$CH_2$—, —$CH_2NH$—, —$CH_2O$—, —NH—, and —O— with the proviso that at least one of X* and Z* is not —$CH_2$—, and Y* is selected from —C(O)— and —$(C(R'')_2)_v$— where R' is hydrogen or $C_{1-4}$ alkyl and v is 1–3.*

*34. A compound according to claim 27 wherein Ar is an unsubstituted heteroaryl group or a substituted heteroaryl group and wherein the heteroaryl group is selected from benzimidazolyl, benzofuryl, benzothiazolyl, benzothienyl, benzoxazolyl, cinnolinyl, dihydroindolyl, furyl, imidazolyl, indolyl, isoquinolyl, isothiazolyl, isoxazolyl, oxadiazolyl, oxazolyl, pyrazinyl, pyrazolyl, pyridazinyl, pyrimidinyl, pyrimidyl, pyrrolyl, quinolinyl, tetrahydroisoquinolyl, tetrahydroquinolyl, tetrazolyl, thiadiazolyl, thiazolyl, thienyl, and compounds of the formula:*

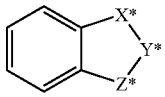

*wherein X* and Z* are independently selected from —$CH_2$—, —$CH_2NH$—, —$CH_2O$—, —NH—, and —O— with the proviso that at least one of X* and Z* is not —$CH_2$—, and Y* is selected from —C(O)— and —$(C(R'')_2)_v$— where R' is hydrogen or $C_{1-4}$ alkyl and v is 1–3.*

*35. A compound according to claim 28 wherein Ar is an unsubstituted heteroaryl group or a substituted heteroaryl group and wherein the heteroaryl group is selected from benzimidazolyl, benzofuryl, benzothiazolyl, benzothienyl, benzoxazolyl, cinnolinyl, dihydroindolyl, furyl, imidazolyl, indolyl, isoquinolyl, isothiazolyl, isoxazolyl, oxadiazolyl, oxazolyl, pyrazinyl, pyrazolyl, pyridazinyl, pyrimidinyl, pyrimidyl, pyrrolyl, quinolinyl, tetrahydroisoquinolyl, tetrahydroquinolyl, tetrazolyl, thiadiazolyl, thiazolyl, thienyl, and compounds of the formula:*

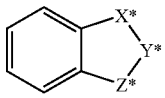

*wherein X* and Z* are independently selected from —$CH_2$—, —$CH_2NH$—, —$CH_2O$—, —NH—, and —O— with the proviso that at least one of X* and Z* is not —$CH_2$—, and Y* is selected from —C(O)— and —$(C(R'')_2)_v$— where R' is hydrogen or $C_{1-4}$ alkyl and v is 1–3.*

* * * * *

UNITED STATES PATENT AND TRADEMARK OFFICE

CERTIFICATE OF CORRECTION

PATENT NO. : RE 39,197 E
APPLICATION NO. : 10/356794
DATED : July 18, 2006
INVENTOR(S) : James T. Link et al.

It is certified that error appears in the above-identified patent and that said Letters Patent is hereby corrected as shown below:

Claim 1, col. 47, line 25, "h. carboxaldehyde, 1 [and]" should read --h. carboxaldehyde, [and]--.

Claim 1, col. 47, lines 40 and 45, delete "and".

Claim 20, col. 57, line 14, "ainino" should read --amino--.

Claim 20, col. 57, line 51, "(2-oxo,-2,3-dihydro" should read --(2-oxo-2,3-dihydro--.

Signed and Sealed this

Seventh Day of November, 2006

JON W. DUDAS
*Director of the United States Patent and Trademark Office*